United States Patent
Jona et al.

(10) Patent No.: US 8,524,730 B2
(45) Date of Patent: *Sep. 3, 2013

(54) SPIROCHROMANONE CARBOXYLIC ACIDS

(75) Inventors: Hideki Jona, Moriya (JP); Yoshihiro Shibata, Koga (JP); Takeru Yamakawa, Yokohama (JP)

(73) Assignee: MSD K.K., Tokyo (JP)

( * ) Notice: Subject to any disclaimer, the term of this patent is extended or adjusted under 35 U.S.C. 154(b) by 263 days.

This patent is subject to a terminal disclaimer.

(21) Appl. No.: 12/997,263

(22) PCT Filed: Jun. 29, 2009

(86) PCT No.: PCT/JP2009/062237
§ 371 (c)(1),
(2), (4) Date: Dec. 10, 2010

(87) PCT Pub. No.: WO2010/002010
PCT Pub. Date: Jan. 7, 2010

(65) Prior Publication Data
US 2011/0077262 A1 Mar. 31, 2011

(30) Foreign Application Priority Data

Jul. 4, 2008 (JP) ................... 2008-175229
Apr. 28, 2009 (JP) ................... 2009-108704

(51) Int. Cl.
*C07D 405/04* (2006.01)
*A61K 31/438* (2006.01)

(52) U.S. Cl.
USPC ........................................... 514/278; 546/17

(58) Field of Classification Search
USPC ........................................ 546/17; 514/278
See application file for complete search history.

(56) References Cited

U.S. PATENT DOCUMENTS

| 7,410,976 B2 | 8/2008 | Yamakawa et al. |
| 2008/0171761 A1 | 7/2008 | Iino et al. |
| 2009/0270435 A1 | 10/2009 | Corbett et al. |
| 2010/0160255 A1 | 6/2010 | Kamata et al. |

FOREIGN PATENT DOCUMENTS

| EP | 1 478 437 B1 | 2/2003 |
| WO | 95/30642 A1 | 11/1995 |
| WO | 03/059871 A1 | 7/2003 |
| WO | 03/059886 A1 | 7/2003 |
| WO | 03/072197 A1 | 9/2003 |
| WO | 03/094912 A1 | 11/2003 |
| WO | 2004/092179 A1 | 10/2004 |
| WO | 2007/011809 A1 | 1/2007 |
| WO | 2007/013691 A1 | 2/2007 |
| WO | 2008/065508 A1 | 6/2008 |
| WO | 2008/070016 A2 | 6/2008 |
| WO | 2008/070016 A3 | 6/2008 |
| WO | 2008/070134 A1 | 6/2008 |
| WO | 2008/088688 A1 | 7/2008 |
| WO | 2008/088692 A2 | 7/2008 |
| WO | 2008/088692 A3 | 7/2008 |
| WO | 2008/102749 A1 | 8/2008 |

OTHER PUBLICATIONS

Machine Translation JP2005162612, equivalent to WO 2003/072197, Sep. 2003.
Machine Translation JP2005170790, equivalent to WO 2008/059871, Jul. 2003.
Machine Translation JP2005320250, equivalent to WO 2003/094912, Nov. 2003.

*Primary Examiner* — Rita Desai
(74) *Attorney, Agent, or Firm* — Janet E. Fair; John C. Todaro

(57) ABSTRACT

The invention relates to a compound of a general formula (I): wherein A represents a linking group; $Ar^1$ represents a group formed from an aromatic ring; $R^1$ and $R^2$ each independently represent a hydrogen atom, a halogen atom, a cyano group, a C2-C6 alkenyl group, a C1-C6 alkoxy group, a halo-C1-C6 alkoxy group, a cyclo-C3-C6 alkyloxy group, a C2-C7 alkanoyl group, a halo-C2-C7 alkanoyl group, a C2-C7 alkoxycarbonyl group, a halo-C2-C7 alkoxycarbonyl group, a cyclo-C3-C6 alkyloxycarbonyl group, an aralkyloxycarbonyl group, a carbamoyl-C1-C6 alkoxy group, a carboxy-C2-C6 alkenyl group, or a group of $-Q^1-N(R^a)-Q^2-R^b$; a C1-C6 alkyl group optionally having substituent(s); an aryl or heterocyclic group optionally having substituent(s); or a C1-C6 alkyl group or a C2-C6 alkenyl group having the aryl or heterocyclic group; T and U each independently represent a nitrogen atom or a methine group; and V represents an oxygen atom, a sulfur atom or an imino group. The compound of the invention is useful as therapeutic agents for various ACC-related diseases.

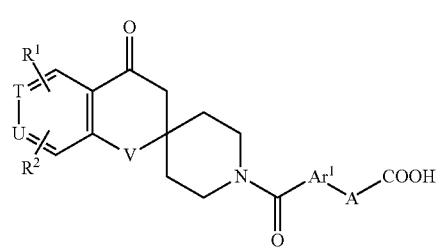

(I)

8 Claims, No Drawings

SPIROCHROMANONE CARBOXYLIC ACIDS

CROSS-REFERENCE TO RELATED APPLICATIONS

This application is a U.S. National Phase application under 35 U.S.C. §371 of PCT Application No. PCT/JP2009/062237, filed Jun. 29, 2009, which published as WO 2010/002010 A1 on Jan. 7, 2010, and claims priority under 35 U.S.C. §365(b) from Japanese patent application No. JP2009-108704, filed Apr. 28, 2009 and JP2008-175229, filed Jul. 4, 2008.

TECHNICAL FIELD

The present invention is useful in the field of medicines. More precisely, novel spirochromanone carboxylic acids of the invention are acetyl CoA carboxylase inhibitors useful as therapeutical agents for various vascular diseases, nervous system diseases, metabolic diseases, genital diseases, digestive system diseases, respiratory diseases, neoplasm and infectious diseases. In addition, they are also useful as herbicides.

BACKGROUND ART

Acetyl CoA carboxylase (hereinafter this may be abbreviated to ACC) is an enzyme that carboxylates acetyl CoA to produce malonyl CoA, and mammals have two isozymes of ACC1 and ACC2 in their own bodies. Malonyl CoA produced by ACC may be a starting material for long-chain fatty acids or neutral fats, and in addition, it may negatively control carnitine palmitoyl transferase-1 (CPT-1) that participates in oxidative decomposition of fatty acids. Of the above isozymes, ACC1 exists in cytoplasm and is considered as a rate-limiting enzyme in biosynthesis of long-chain fatty acids, while, ACC2 exists predominantly on mitochondria and is said to participate principally in oxidation of fatty acids. Accordingly, compounds capable of inhibiting ACC1 and/or ACC2 are expected not only to inhibit synthesis of fatty acids but also to reduce accumulated fats. In fact, it is shown that, as compared with normal mice, ACC2-knocked out mice hardly get fat (see *Proceedings of the National Academy of Sciences of the United States of America*, 100 (18), pp. 10207-10212, 2003).

An excess of accumulated fats may cause, for example, insulin resistance, diabetes, hypertension, hyperlipemia and obesity, and it is known that a plurality of those factors, as combined, lead to an extremely higher risk of arteriosclerosis, and the symptom is referred to as a metabolic syndrome. Further, it is known that hypertriglyceridemia or obesity leads to a higher risk of, for example, pancreatitis, liver dysfunction, cancers such as breast cancer, uterine cancer, ovarian cancer, colon cancer and prostate cancer, emmeniopathy, arthritis, gout, cholecystitis, gastroesophageal reflux, pickwickian syndrome, sleep apnea syndrome. It is well known that diabetes often causes, for example, cardiac angina, heart failure, stroke, claudication, retinopathy, eyesight failure, renal failure, neuropathy, skin ulcer, infectious diseases (see *The Merck Manual of Medical Information*, second home edition, Merck & Co., 2003). Accordingly, ACC inhibitors are useful for the treatment and/or prevention of such disorders.

ACC exists also in plants, parasites, bacteria and fungi, and it is known that it participates in the growth of cells. For example, aryloxyphenoxypropionic acid-type herbicides represented by diclofop, and cyclohexanedione-type herbicides represented by setoxydim excert their activity by inhibiting ACC in plants (see *Biochemical Society of Transaction*, 22(3), p. 616 (1994)), and the aryloxyphenoxypropionic acids also exhibit a growth-inhibiting effect on parasites (see *Journal of Biological Chemistry*, 277 (26), pp. 23208-23215 (2002)). In addition, sorafen and moiramide B known as ACC inhibitors exhibit an antibacterial effect and an antifungal effect (see *Current Genetics*, 25 (2), pp. 95-100 (1994); *Journal of Biological Chemistry*, 279 (25), pp. 26066-26073 (2004)).

Tumor cells generally show an increased synthesis of fatty acids, and it is reported that some fatty acid synthesis inhibitors exhibit a cell growth-inhibiting effect.

Based on the above-mentioned information, ACC inhibitors are expected to be useful for the treatment and/or prevention of disorders such as hyperlipemia, fatty liver, dyslipidemia, hepatic dysfunction, obesity, diabetes, insulin resistance, metabolic syndrome, arteriosclerosis, hypertension, cardiac angina, heart failure, cardiac infarction, stroke, claudication, retinopathy, eyesight failure, renal failure, electrolyte metabolism disorder, neuropathy, skin ulcer, bulimia, pancreatitis, emmeniopathy, arthritis, gout, cholecystitis, gastroesophageal reflux, pickwickian syndrome, sleep apnea syndrome, infectious diseases, neoplasm, and also as herbicides.

Up to the present, for example, those described in a pamphlet of WO 2003/094912, WO 2003/072197, WO 2003/059886, or WO 2003/059871 are known as compounds capable of inhibiting ACC, but the compounds described in these references are totally different from the compounds of the present invention in point of their structures.

On the other hand, various compounds having the same spirochromanone skeleton as that of the compounds of the present invention are disclosed in a pamphlet of WO 95/30642, EP 431973A, WO 2004/092179 or WO 2008/065508. However, these references do neither disclose nor suggest the compounds of the invention.

DISCLOSURE OF INVENTION

The present invention provides compounds of the following general formula (I), and pharmaceutically acceptable salts or esters thereof, which have a strong ACC-inhibiting effect:

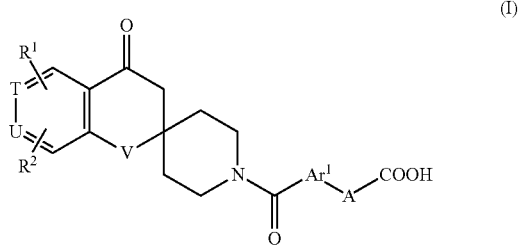

wherein A represents a linking group formed from a carbo- or heterocyclic ring, or formed from a C1-C6 hydrocarbon chain optionally interrupted by an oxygen atom, a sulfur atom or an imino group, in which said linking group optionally has substituent(s) selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a C2-C7 alkanoylamino group, a C1-C6 alkylcarbamoyl group, a cyclo-C3-C6 alkylcarbamoyl group, a (C1-C6 alkoxy-C1-C6 alkyl)carbamoyl group, a C2-C7 alkoxycarbonyl group, a C1-C6 alkylsulfonyl group, a C1-C6 alkylsulfonylamino group and a tetrazolyl group;

$Ar^1$ represents a group formed from an aromatic ring optionally having substituent(s) selected from $R^3$;

$R^1$ and $R^2$ each independently represent a hydrogen atom, a halogen atom, a cyano group, a C2-C6 alkenyl group, a C1-C6 alkoxy group, a halo-C1-C6 alkoxy group, a cyclo-C3-C6 alkyloxy group, a C2-C7 alkanoyl group, a halo-C2-C7 alkanoyl group, a C2-C7 alkoxycarbonyl group, a halo-C2-C7 alkoxycarbonyl group, a cyclo-C3-C6 alkyloxycarbonyl group, an aralkyloxycarbonyl group, a carbamoyl-C1-C6 alkoxy group, a carboxy-C2-C6 alkenyl group, or a group of $-Q^1-N(R^a)-Q^2-R^b$;

a C1-C6 alkyl group optionally having substituent(s) selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group;

an aryl or heterocyclic group optionally having substituent(s) selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of $-CO-N(R^c)R^d$; or a C1-C6 alkyl group or a C2-C6 alkenyl group having the aryl or heterocyclic group;

$R^3$ represents a halogen atom, a nitro group, a cyano group, a hydroxyl group, a carboxyl group, a C2-C6 alkenyl group, a cyclo-C3-C6 alkyl group, or a group of $-N(R^e)R^f$; a phenoxy group, a C1-C6 alkoxy group, a C2-C7 alkoxycarbonyl group, a C1-C6 alkylthio group, a cyclo-C3-C6 alkyloxy group, a cyclo-C3-C6 alkyloxycarbonyl group, a cyclo-C3-C6 alkyl-C1-C6 alkoxy group, a cyclo-C3-C6 alkylthio group or a cyclo-C3-C6 alkyl-C1-C6 alkylthio group, optionally substituted with a halogen atom or a hydroxyl group, wherein the cyclo-C3-C6 alkyl group in the cyclo-C3-C6 alkyloxy group, the cyclo-C3-C6 alkyloxycarbonyl group, the cyclo-C3-C6 alkyl-C1-C6 alkoxy group, the cyclo-C3-C6 alkylthio group or the cyclo-C3-C6 alkyl-C1-C6 alkylthio group may be interrupted by an oxygen atom, a sulfur atom or an imino group;

a C1-C6 alkyl group optionally having substituent(s) selected from a group consisting of a halogen atom, a hydroxyl group, a cyclo-C3-C6 alkyl group and a C1-C6 alkoxy group; or a phenyl group, a 1,2,4-triazolyl group or a tetrazolyl group optionally having substituent(s) selected from a group consisting of a halogen atom, a nitro group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group and a C1-C6 alkylthio group;

$Q^1$ and $Q^2$ each independently represent a single bond, or a group of $-CO-$, $-SO_2-$ or $-C(R^g)(R^h)-$;

$R^a$ and $R^b$ each independently represent a hydrogen atom, a C2-C6 alkenyl group, a C1-C6 alkoxy group, a cyclo-C3-C6 alkyloxy group, a halo-C1-C6 alkoxy group, a cyclo-C3-C6 alkyl group, an aralkyloxy group, a carbamoyl group, a C2-C7 alkoxycarbonyl group, or a group of $-N(R^i)R^j$;

a C1-C6 alkyl group optionally having substituent(s) selected from a group consisting of a halogen atom, a C1-C6 alkoxy group, a carbamoyl group and a C2-C7 alkoxycarbonyl group; or a heteroaromatic group optionally substituted with a C1-C6 alkyl group optionally having substituent(s) selected from a group consisting of a halogen atom, a C1-C6 alkoxy group, a carbamoyl group and a C2-C7 alkoxycarbonyl group;

$R^c$, $R^d$, $R^g$, $R^h$, $R^i$ and $R^j$ each independently represent a hydrogen atom, a C1-C6 alkyl group, or a halo-C1-C6 alkyl group;

$R^e$ and $R^f$ each independently represent a hydrogen atom, a C1-C6 alkyl group, or a halo-C1-C6 alkyl group, or $R^e$ and $R^f$ can be taken together to form a C2-C5 alkylene group optionally interrupted by an oxygen atom, a sulfur atom or an imino group;

T and U each independently represent a nitrogen atom or a methine group; and

V represents an oxygen atom, a sulfur atom or an imino group.

The compounds (I) of the invention have an ACC-inhibiting effect and are useful as therapeutical agents for various ACC-related disorders, for example, vascular diseases such as hypertension, cardiac angina, heart failure, cardiac infarction, stroke, claudication, diabetic nephropathy, diabetic retinopathy, eyesight failure, electrolyte metabolism disorder, arteriosclerosis; nervous system diseases such as bulimia, diabetic neuropathy; metabolic diseases such as metabolic syndrome, obesity, diabetes, insulin resistance, hyperlipemia, hypercholesterolemia, hypertriglyceridemia, dyslipidemia, nonalcoholic fatty liver, hormone secretion failure, gout, and hepatic steatosis; genital diseases such as emmeniopathy, sexual dysfunction; digestive system diseases such as liver dysfunction, pancreatitis, cholecystitis, gastroesophageal reflux; respiratory diseases such as obesity-hypoventilation syndrome (pickwickian syndrome), sleep apnea syndrome; infectious diseases caused by bacteria, fungi or parasites; malignant neoplasm; and inflammatory diseases such as arthritis and skin ulcer. The compounds are also useful as herbicides.

In particular, the compounds (I) of the invention are useful as therapeutical agents, for example, for metabolic syndrome, fatty liver, hyperlipemia, obesity, diabetes, bulimia, malignant neoplasm and infectious diseases.

In addition, the compounds (I) characterized by the terminal carboxyl group via linking group A have improved properties such as decreasing affinity for certain metabolic enzymes, thus the invention provides safe and effective compounds for various ACC-related disorders.

The invention relates to the compounds of formula (I), and their pharmaceutically acceptable salts and esters, and to their production and use.

The meanings of the terms used herein are mentioned below, and the invention is described in more detail hereinunder.

"Halogen atom" includes a fluorine atom, a chlorine atom, a bromine atom, and an iodine atom.

"C1-C6 alkyl group" means a linear or branched alkyl group having from 1 to 6 carbon atoms, and it includes, for example, a methyl group, an ethyl group, a propyl group, an isopropyl group, a butyl group, an isobutyl group, a sec-butyl group, a tert-butyl group, a pentyl group, an isopentyl group, a hexyl group, and an isohexyl group.

"Halo-C1-C6 alkyl group" means the above-mentioned C1-C6 alkyl group which is substituted with the above-mentioned halogen atom(s) of the same type or different types and which has one or two or more, but preferably from 1 to 3 unlimited substitutable positions, and it includes, for example, a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, and an iodomethyl group.

"Hydroxy-C1-C6 alkyl group" means the above-mentioned C1-C6 alkyl group which is substituted with hydroxyl group(s) and which has one or two or more, but preferably one or two unlimited substitutable positions, and it includes, for example, a hydroxymethyl group, a 2-hydroxyethyl group, a 1-hydroxy-1-methylethyl group, a 1,2-dihydroxyethyl group, and a 3-hydroxypropyl group.

"Cyclo-C3-C6 alkyl group" means a cycloalkyl group having from 3 to 6 carbon atoms, and it includes a cyclopropyl group, a cyclobutyl group, a cyclopentyl group, and a cyclohexyl group.

"C2-C6 alkenyl group" means a linear or branched alkenyl group having from 2 to 6 carbon atoms, and it includes, for example, a vinyl group, a 1-propenyl group, a 2-propenyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group, and a 4-pentenyl group.

"C1-C6 alkoxy group" means a linear or branched alkoxy group having from 1 to 6 carbon atoms, and it includes, for example, a methoxy group, an ethoxy group, a propoxy group, an isopropoxy group, a butoxy group, a sec-butoxy group, an isobutoxy group, a tert-butoxy group, a pentyloxy group, an isopentyloxy group, a hexyloxy group, and an isohexyloxy group.

"Halo-C1-C6 alkoxy group" means the above-mentioned C1-C6 alkoxy group which is substituted with the above-mentioned halogen atom(s) of the same type or different types and which has one or two or more, but preferably from 1 to 3 unlimited substitutable positions, and it includes, for example, a fluoromethoxy group, a difluoromethoxy group, a trifluoromethoxy group, a 2-fluoroethoxy group, a 1,2-difluoroethoxy group, a 2,2,2-trifluoroethoxy group, a chloromethoxy group, a 2-chloroethoxy group, a 1,2-dichloroethoxy group, a bromomethoxy group, and an iodomethoxy group.

"C1-C6 alkylthio group" means a linear or branched alkylthio group having from 1 to 6 carbon atoms, and it includes, for example, a methylthio group, an ethylthio group, a propylthio group, an isopropylthio group, a butylthio group, a sec-butylthio group, an isobutylthio group, a tert-butylthio group, a pentylthio group, an isopentylthio group, a hexylthio group, and an isohexylthio group.

"C2-C7 alkanoyl group" means an alkanoyl group having the above-mentioned C1-C6 alkyl group, or that is, an alkanoyl group having from 2 to 7 carbon atoms, and it includes, for example, an acetyl group, a propionyl group, a butyryl group, an isobutyryl group, a valeryl group, an isovaleryl group, and a pivaloyl group.

"Halo-C2-C7 alkanoyl group" means the above-mentioned C2-C7 alkanoyl group which is substituted with the above-mentioned halogen atom(s) of the same type or different types and which has one or two or more, but preferably from 1 to 3 unlimited substitutable positions, and it includes, for example, a chloroacetyl group, a dichloroacetyl group, a fluoroacetyl group, a difluoroacetyl group, a 3-chloropropionyl group, and a 3-fluoropropionyl group.

"C2-C7 alkanoylamino group" means an amino group that is mono-substituted or di-substituted, preferably mono-substituted with the above-mentioned C2-C7 alkanoyl group, and it includes, for example, an acetylamino group, a propionylamino group, a butyrylamino group, an isobutyrylamino group, a valerylamino group, an isovalerylamino group, a pivaloylamino group.

"C1-C6 alkylcarbamoyl group" means a carbamoyl group that is mono-substituted or di-substituted with the above-mentioned C1-C6 alkyl group, and it includes, for example, a methylcarbamoyl group, a dimethylcarbamoyl group, an ethylcarbamoyl group, a diethylcarbamoyl group, an ethyl(methyl)carbamoyl group, a propylcarbamoyl group, an isopropylcarbamoyl group.

"Cyclo-C3-C6 alkylcarbamoyl group" means a carbamoyl group that is mono-substituted or di-substituted, preferably mono-substituted with the above-mentioned cyclo-C3-C6 alkyl group, and it includes, for example, a cyclopropylcarbamoyl group, a cyclobutylcarbamoyl group, a cyclopentylcarbamoyl group, a cyclohexylcarbamoyl group.

"C1-C6 alkoxy-C1-C6 alkyl group" means the above-mentioned C1-C6 alkyl group which is substituted with the above-mentioned C1-C6 alkoxy group(s) of the same type or different types and which has one or two or more, but preferably from 1 or 2 unlimited substitutable positions, and it includes, for example, a methoxymethyl group, an ethoxymethyl group, a 2-mehtoxyethyl group, a 2-ethoxyethyl group, a 1-methoxy-1-methylethyl group, a 1,2-dimethoxyethyl group, a 3-methoxypropyl group.

"(C1-C6 alkoxy-C1-C6 alkyl)carbamoyl group" means a carbamoyl group that is mono-substituted or di-substituted, preferably mono-substituted with the above-mentioned C1-C6 alkoxy-C1-C6 alkyl group, and it includes, for example, a (methoxymethyl)carbamoyl group, an (ethoxymethyl)carbamoyl group, a (2-methoxyethyl)carbamoyl group, a (2-ethoxyethyl)carbamoyl group, a (1-methoxy-1-methylethyl)carbamoyl group, a (1,2-dimethoxyethyl)carbamoyl group, a (3-methoxypropyl)carbamoyl group.

"C2-C7 alkoxycarbonyl group" means an alkoxycarbonyl group having the above-mentioned C1-C6 alkoxy group, or that is, an alkoxycarbonyl group having from 2 to 7 carbon atoms, and it includes, for example, a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, and a pentyloxycarbonyl group.

"Halo-C2-C7 alkoxycarbonyl group" means a haloalkoxycarbonyl group having the above-mentioned halo-C1-C6 alkoxy group, and it includes, for example, a 2,2-difluoroethoxycarbonyl group.

"Carbamoyl-C1-C6 alkoxy group" means the above-mentioned C1-C6 alkoxy group substituted with one or two or more, preferably one carbamoyl group at the substitutable position thereof, and it includes, for example, a carbamoylmethoxy group, a 1-carbamoylethoxy group, a 2-carbamoylethoxy group, a 2-carbamoylpropoxy group, and a 3-carbamoylpropoxy group.

"Carboxy-C2-C6 alkenyl group" means the above-mentioned C2-C6 alkenyl group substituted with one or two or more, preferably one carboxyl group at the substitutable position thereof, and it includes, for example, a 1-carboxyvinyl group, a 2-carboxyvinyl group, a 2-carboxy-1-propenyl group, a 3-carboxy-1-propenyl group, a 3-carboxy-2-propenyl group, a 4-carboxy-3-butenyl group, and a 4-carboxy-2-butenyl group.

"C2-C7 alkanoyloxy group" means an alkanoyloxy group having the above-mentioned C2-C7 alkanoyl group, and it includes, for example, an acetyloxy group, a propionyloxy group, a butyryloxy group, an isobutyryloxy group, a valeryloxy group, an isovaleryloxy group, and a pivaloyloxy group.

"C1-C6 alkylsulfonyl group" means a linear or branched alkylsulfonyl group having from 1 to 6 carbon atoms, and it includes, for example, a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group, and an isohexylsulfonyl group.

"C1-C6 alkylsulfonylamino group" means an amino group that is mono-substituted or di-substituted, preferably mono-substituted with the above-mentioned C1-C6 alkylsulfonyl group, and it includes, for example, a methylsulfonylamino group, an ethylsulfonylamino group, a propylsulfonylamino group, an isopropylsulfonylamino group, a butylsulfonylamino group, a sec-butylsulfonylamino group, an isobutylsulfonylamino group, a tert-butylsulfonylamino group, a pentylsulfonylamino group, an isopentylsulfonylamino group, a hexylsulfonylamino group, an isohexylsulfonylamino group.

"C2-C7 alkanoyloxy-C1-C6 alkyl group" means the above-mentioned C1-C6 alkyl group substituted with one or two or more, preferably one C2-C7 alkanoyloxy group at any substitutable position thereof, and it includes, for example, an acetyloxymethyl group, a propionyloxymethyl group, a butyryloxymethyl group, an isobutyryloxymethyl group, a valeryloxymethyl group, an isovaleryloxymethyl group, and a pivaloyloxymethyl group.

"Carbocyclic ring" means 3 to 10 membered saturated or unsaturated monocyclic or bicyclic carbon ring, which may be an aromatic or non-aromatic ring, and it includes, for example, a cyclopropane ring, a cyclobutane ring, a cyclopentane ring, a cyclohexane ring, a cycloheptane ring, a cyclopropene ring, a cyclobutene ring, a cyclopentene ring, a cyclohexene ring, a cycloheptene ring, a benzene ring, and a naphthalene ring.

"Heterocyclic ring" means a 3- to 7-membered saturated or unsaturated monocyclic heterocyclic ring which has one or two or more, but preferably from 1 to 3 and the same or different hetero atoms selected from a group consisting of oxygen, nitrogen and sulfur atoms, or means a condensed-cyclic heterocyclic ring which is constructed through condensation of the monocyclic heterocyclic ring and a 3- to 7-membered carbocyclic ring or through condensation of those, same or different monocyclic heterocyclic rings, which may be an aromatic or non-aromatic ring, and it includes, for example, a pyrroline ring, a furan ring, a thiophene ring, an imidazole ring, a pyrazole ring, a thiazole ring, an isothiazole ring, an oxazole ring, an isoxazole ring, a triazole ring, a tetrazole ring, an oxadiazole ring, a 1,2,3-thiadiazole ring, a, 1,2,4-thiadiazole ring, a 1,3,4-thiadiazole ring, a pyridine ring, a pyrazine ring, a pyrimidine ring, a pyridazine ring, a 1,2,4-triazine ring, a 1,3,5-triazine ring, an indole ring, a benzofuran ring, a benzothiophene ring, a benzimidazole ring, a benzoxazole ring, a benzisoxazole ring, a benzothiazole ring, a benzisothiazole ring, an indazole ring, a purine ring, a quinoline ring, an isoquinoline ring, a phthalazine ring, a 1,5-naphthyridine ring, a 1,6-naphthyridine ring, a 1,7-naphthyridine ring, a 1,8-naphthridine ring, a 2,6-naphthyridine ring, a 2,7-naphthyridine ring, a quinoxaline ring, a quinazoline ring, a cinnoline ring, a pteridine ring, a 1H-indazole ring, a 2H-indazole ring, a 1H-furo[2,3-c]pyrazole ring, a 1H-thieno[2,3-c]pyrazole ring, an imidazo[1,2-a]pyridine ring, an imidazo[1,5-a]pyridine ring, a 1H-pyrazolo[3,4-b]pyridine ring, a pyrido[3,2-b]pyridine ring, a pyrrolidine ring, a dihydro-1,2,4-triazole ring, a dihydro-1,2,4-oxadiazole ring, a dihydro-1,3,4-oxadiazole ring, a dihydro-1,2,4-thiadiazole ring, a dihydro-1,2,3,5-oxathiadiazole ring, a piperidine ring, a piperazine ring, a morpholine ring, and a thiomorpholine ring.

"Aromatic ring" means a carbocyclic aromatic ring and a heterocyclic aromatic ring, and it includes, for example, those aromatic ring listed in the above-mentioned carbocyclic ring and heterocyclic ring.

"C1-C6 hydrocarbon chain" means a linear or branched saturated or unsaturated aliphatic hydrocarbon chain having from 1 to 6 carbon atoms, and it includes, for example, a C1-C6 alkane chain such as a methane chain, an ethane chain, a propane chain, a butane chain, a pentane chain and a hexane chain, a C2-C6 alkene chain such as an ethene chain, a propene chain, a butene chain, a pentene chain and a hexene chain, and a C2-C6 alkyne chain such as an ethyne chain, a propyne chain, a butyne chain, a pentyne chain and a hexyne chain.

"C1-C6 hydrocarbon chain optionally interrupted by an oxygen atom, a sulfur atom or an imino group" means the above-mentioned hydrocarbon chain which is interrupted or not by one or two or more, but preferably one oxygen atom, sulfur atom or imino group at any position of the hydrocarbon chain thereof capable of being interrupted by it, and this includes, for example, a methane chain, an ethane chain, a propane chain, a butane chain, a pentane chain, a hexane chain, an ethene chain, a propene chain, a butene chain, a pentene chain, a hexene chain, an ethyne chain, a propyne chain, a butyne chain, a pentyne chain, a hexyne chain, a 1-oxaethane chain, a 1-oxapropane chain, a 2-oxapropane chain, a 1-thiaethane chain, a 1-thiapropane chain, a 2-thiapropane chain, a 1-azaethane chain, a 1-azapropane chain, and a 2-azapropane chain.

"Aryl group" includes, for example, a phenyl group, a naphthyl group.

"Aralkyl group" means the above-mentioned C1-C6 alkyl group which is substituted one or two or more, preferably one aryl group at any substitutable position thereof, and it includes, for example, a benzyl group, a 1-phenylethyl group, a phenethyl group, a 1-naphthylmethyl group, and a 2-naphthylmethyl group.

"Aralkyloxy group" means an aralkyloxy group having the above-mentioned aralkyl group, and it includes, for example, a benzyloxy group, a 1-phenylethyloxy group, a phenethyloxy group, a 1-naphthylmethyloxy group, and a 2-naphthylmethyloxy group.

"Aralkyloxycarbonyl group" means an aralkyloxycarbonyl group having the above-mentioned aralkyloxy group, and it includes, for example, a benzyloxycarbonyl group, a 1-phenylethyloxycarbonyl group, a phenethyloxycarbonyl group, a 1-naphthylmethyloxycarbonvl group, and a 2-naphthylmethyloxycarbonyl group.

"Heteroaromatic group" means a 5-membered or 6-membered monocyclic aromatic heterocyclic group which has one or two or more, but preferably from 1 to 3 and the same or different hetero atoms selected from a group consisting of oxygen, nitrogen and sulfur atoms, or means a condensed-cyclic aromatic heterocyclic group which is constructed through condensation of the monocyclic aromatic heterocyclic group and the above-mentioned aryl group or through condensation of those, same or different monocyclic aromatic heterocyclic groups; and it includes, for example, a pyrrolyl group, a furyl group, a thienyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a, 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a 1,5-naphthyridinyl group, a 1,6-naphthyridinyl group, a 1,7-naphthyridinyl group, a 1,8-naphthyridinyl group, a 2,6-naphthyridinyl group, a 2,7-naphthyridinyl group, a quinoxalinyl group, a quinazolinyl group, a cinnolinyl group, and a pteridinyl group.

"Heterocyclic group" means a 3- to 7-membered monocyclic heterocyclic group which has one or two or more, but preferably from 1 to 3 and the same or different hetero atoms selected from a group consisting of oxygen, nitrogen and sulfur atoms, or means a condensed-cyclic heterocyclic group which is constructed through condensation of the monocyclic heterocyclic group and a 3- to 7-membered carbocyclic group or through condensation of those, same or different monocyclic heterocyclic groups; and it includes the above-mentioned heterocyclic aromatic groups. Its examples are, in addition to those listed hereinabove for the above-mentioned heterocyclic aromatic group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a piperidyl group, a piperazinyl group, a morpholinyl group, and a thiomorpholinyl group.

"Cyclo-C3-C6 alkyloxy group" means a cycloalkyloxy group having the above-mentioned cyclo-C3-C6 alkyl group, and it includes a cyclopropyloxy group, a cyclobutyloxy group, a cyclopentyloxy group, and a cyclohexyloxy group.

"Cyclo-C3-C6 alkyloxycarbonyl group" means a cycloalkyloxycarbonyl group having the above-mentioned cyclo-C3-C6 alkyloxy group, and it includes, for example, a cyclopropyloxycarbonyl group, a cyclobutyloxycarbonyl group.

"Cyclo-C3-C6 alkyl-C1-C6 alkoxy group" means the above-mentioned C1-C6 alkoxy group which is substituted with one or two or more, preferably one cyclo-C3-C6 alkyl group at any substitutable position thereof, and it includes, for example, a cyclopropylmethoxy group, a cyclobutylmethoxy group, a cyclopentylmethoxy group, a cyclopropylethoxy group, a cyclobutylethoxy group, and a cyclopropyipropoxy group.

"Cyclo-C3-C6 alkylthio group" means a cycloalkylthio group having the above-mentioned cyclo-C3-C6 alkyl group, and it includes a cyclopropylthio group, a cyclobutylthio group, a cyclopentylthio group, and a cyclohexylthio group.

"Cyclo-C3-C6 alkyl-C1-C6 alkylthio group" means the above-mentioned C1-C6 alkylthio group substituted with one or two or more, preferably one cyclo-C3-C6 alkyl group at any substitutable position thereof, and it includes, for example, a cyclopropylmethylthio group, a cyclobutylmethylthio group, a cyclopentylmethylthio group, a cyclopropylethylthio group, a cyclobutylethylthio group, and a cyclopropylpropylthio group.

"Cyclo-C3-C6 alkyl group optionally interrupted by an oxygen atom, a sulfur atom or an imino group" means that the cyclo-C3-C6 alkyl group is the above-mentioned cyclo-C3-C6 alkyl group, or means that the carbon atom(s) constituting the cyclo-C3-C6 alkyl group is/are replaced with one or two or more, preferably one oxygen atom, sulfur atom or imino group so that the cyclo-C3-C6 alkyl group is interrupted by it. The group includes, for example, those listed hereinabove as the above-mentioned cyclo-C3-C6 alkyl group, and in addition to these, an oxiranyl group, an oxetanyl group, a tetrahydrofuranyl group, a tetrahydro-2H-pyranyl group, a thiiranyl group, a thietanyl group, a tetrahydrothienyl group, a tetrahydro-2H-thiopyranyl group, an aziridinyl group, an azetidinyl group, a pyrrolidinyl group, and a piperidyl group.

"C1-C6 alkylene group" means a linear or branched alkylene group having from 1 to 6 carbon atoms, and it includes, for example, a methylene group, an ethylene group, a trimethylene group, a tetramethylene group, a pentamethylene group, and a hexamethylene group.

"C2-C5 alkylene group optionally interrupted by an oxygen atom, a sulfur atom or an imino group" means an alkylene group having from 2 to 5 carbon atoms, which is interrupted or not by one or two or more, but preferably one oxygen atom, sulfur atom or imino group at any position of the alkylene chain thereof capable of being interrupted by it, and this includes, for example, an ethylene group, a trimethylene group, a tetramethylene group, a pentamethylene group, 2-oxatetramethylene group, a 2-oxapentamethylene group, 3-oxapentamethylene group, a 2-thiatetramethylene group, a 2-thiapentamethylene group, a 3-thiapentamethylene group, a 2-azatetramethylene group, 2-azapentamethylene group, and a 3-azapentamethylene group.

"Pharmaceutically acceptable salts" of the compound of formula (I) mean pharmaceutically acceptable common salts, including, for example, base addition salts of the compound having the terminal carboxyl group on the linking group "A", and/or the compound having other carboxyl group, a hydroxyl group and/or an acidic heterocyclic group such as a tetrazolyl group, if any, with a base added to the carboxyl group, the hydroxyl group or the acidic heterocyclic group of the compound; and acid addition salts of the compound having an amino group or a basic heterocyclic group, with an acid added to the amino group or the basic heterocyclic group of the compound.

The base addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid addition salts include, for example, inorganic acid salts such as hydrochlorides, sulfates, nitrates, phosphates, perchlorates; organic acid salts such as maleates, fumarates, tartrates, citrates, ascorbates, trifluoroacetates, methanesulfonates, isethionates, benzenesulfonates, p-toluenesulfonates.

"Pharmaceutically acceptable esters" of the compound of formula (I) mean those of the compound having the terminal carboxyl group on the linking group "A", and/or other carboxyl group, if any, which are esterified at the carboxyl group of the terminal carboxyl group on the linking group "A" and/or at other carboxyl group of the compound and which are pharmaceutically acceptable common esters, including, for example, esters with a C1-C6 alkyl group such as a methyl group, an ethyl group, a propyl group, an isopropyl group, a butyl group, a sec-butyl group, a tert-butyl group, a pentyl group, an isopentyl group, a neopentyl group, a cyclopropyl group, a cyclobutyl group or cyclopentyl group; esters with an aralkyl group such as a benzyl group or a phenethyl group; esters with a C2-C6 alkenyl group such as an allyl group or a 2-butenyl group; esters with a C1-C6 alkoxy-C1-C6 alkyl group such as a methoxymethyl group, a 2-methoxyethyl group or a 2-ethoxyethyl group; esters with a C2-C7 alkanoyloxy-C1-C6 alkyl group such as an acetoxymethyl group, a pivaloyloxymethyl group or a 1-pivaloyloxyethyl group; esters with a C2-C7 alkoxycarbonyl-C1-C6 alkyl group such as a methoxycarbonylmethyl group or an isopropoxycarbonylmethyl group; esters with a carboxy-C1-C6 alkyl group such as a carboxymethyl group; esters with a C2-C7 alkoxycarbonyloxy-C1-C6 alkyl group such as a 1-(ethoxycarbonyloxy)ethyl group or a 1-(cyclohexyloxycarbonyloxy)ethyl group; esters with a carbamoyloxy-C1-C6 alkyl group such as a carbamoyloxymethyl group; esters with a phthalidyl group; and esters with a (5-substituted-2-oxo-1,3-dioxol-4-yl)methyl group such as a (5-methyl-2-oxo-1,3-dioxol-4-yl)methyl group.

"Therapeutical agent" means a medicine used for the treatment and/or prevention of various disorders.

For more concrete disclosure of the compounds of formula (I) of the invention, the symbols used in formula (I) are described in detail hereinunder with reference to their preferred examples.

"A" represents a linking group formed from a carbo- or heterocyclic ring, or formed from a C1-C6 hydrocarbon chain optionally interrupted by an oxygen atom, a sulfur atom or an imino group, in which said linking group optionally has substituent(s) selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a C2-C7 alkanoylamino group, a C1-C6 alkylcarbamoyl group, a cyclo-C3-C6 alkylcarbamoyl group, a (C1-C6 alkoxy-C1-C6 alkyl)carbamoyl group, a C2-C7 alkoxycarbonyl group, a C1-C6 alkylsulfonyl group, a C1-C6 alkylsulfonylamino group and a tetrazolyl group.

"Linking group formed from a carbo- or heterocyclic ring, or formed from a C1-C6 hydrocarbon chain" means a linking group formed by removing the hydrogen atoms from the carbo- or heterocyclic ring, or the C1-C6 hydrocarbon chain optionally interrupted by an oxygen atom, a sulfur atom or an imino group.

The linking group means at least 2-valent group necessarily bonding to the adjacent carboxyl group and $Ar^1$, and optionally it may have one or two or more substituents selected from selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a C2-C7 alkanoylamino group, a C1-C6 alkylcarbamoyl group, a cyclo-C3-C6 alkylcarbamoyl group, a (C1-C6 alkoxy-C1-C6 alkyl)carbamoyl group, a C2-C7 alkoxycarbonyl group, a C1-C6 alkylsulfonyl group, a C1-C6 alkylsulfonylamino group and a tetrazolyl group, and it may be 3- or 4-valent or more poly-valent group bonding to the substituent. Those substituent(s), $Ar^1$ and carboxyl group may independently bond to any bondable position on the linking group A.

The carbo- or heterocyclic ring itself for the linking group is, for example, preferably a benzene ring, a furan ring, a thiophene ring, a pyrazole ring, a thiazole ring, an oxazole ring, an isoxazole ring, a 1,2,4-triazole ring, a 1,2,4-oxadiazole ring, a 1,3,4-oxadiazole ring, a tetrazole ring, a pyridine ring, a pyrazine ring, a pyrimidine ring, an indole ring, a benzo[b]thiophene ring, a piperidine ring, a piperazine ring, a morpholine ring or a thiomorpholine ring, more preferably a benzene ring, a pyridine ring or a piperidine ring.

The C1-C6 hydrocarbon chain optionally interrupted by an oxygen atom, a sulfur atom or an imino group itself for the linking group is, for example, preferably a C1-C6 alkane chain, a C2-C6 alkene chain and a C2-C6 alkyne chain, which may be interrupted by an oxygen atom, a sulfur atom or an imino group, more specifically a methane chain, an ethane chain, or 1-oxaethane chain.

The halogen atom for the substituent is, for example, preferably a fluorine atom, a chlorine atom.

The C1-C6 alkyl group for the substituent is, for example, preferably a methyl group, an ethyl group.

The halo-C1-C6 alkyl group for the substituent is, for example, preferably a fluoromethyl group, a difluoromethyl group, a trifluoromethyl group.

The hydroxy-C1-C6 alkyl group for the substituent is, for example, preferably a hydroxymethyl group, a 1-hydroxyethyl group, a 2-hydroxyethyl group.

The cyclo-C3-C6 alkyl group for the substituent is, for example, preferably a cyclopropyl group.

The C2-C6 alkenyl group for the substituent is, for example, preferably a 2-propenyl group, an isopropenyl group.

The C1-C6 alkoxy group for the substituent is, for example, preferably a methoxy group, an ethoxy group.

The halo-C1-C6 alkoxy group for the substituent is, for example, preferably a difluoromethoxy group.

The C1-C6 alkylthio group for the substituent is, for example, preferably a methylthio group, an ethylthio group.

The C2-C7 alkanoylamino group for the substituent is, for example, preferably an acetylamino group.

The C1-C6 alkylcarbamoyl group for the substituent is, for example, preferably a methylcarbamoyl group, a diethylcarbamoyl group.

The cyclo-C3-C6 alkylcarbamoyl group for the substituent is, for example, preferably a cyclopropylcarbamoyl group, a cyclopentylcarbamoyl group.

The (C1-C6 alkoxy-C1-C6 alkyl)carbamoyl group for the substituent is, for example, preferably a (methoxymethyl)carbamoyl group.

The C2-C7 alkoxycarbonyl group for the substituent is, for example, preferably a methoxycarbonyl group, an ethoxycarbonyl group.

The C1-C6 alkylsulfonyl group for the substituent is, for example, preferably a methylsulfonyl group, an ethylsulfonyl group.

The C1-C6 alkylsulfonylamino group for the substituent is, for example, preferably a methylsulfonylamino group, an ethylsulfonylamino group.

In one embodiment, the substituent(s) are selected from a group consisting of a halogen atom, a cyano group, a C1-C6 alkyl group, a C1-C6 alkoxy group, a C2-C7 alkanoylamino group, a (C1-C6 alkoxy-C1-C6 alkyl)carbamoyl group, a C2-C7 alkoxycarbonyl group, a C1-C6 alkylsulfonyl group, a C1-C6 alkylsulfonylamino group, and a tetrazolyl group.

In another embodiment, the linking group A does not bond to a group other than a carboxyl group and $Ar^1$.

The linking group is preferably formed from the carbo- or heterocyclic ring optionally substituted with above-mentioned substituent(s).

Examples of the group of formula: -A-COOH are, for example, preferably 2-carboxyphenyl, 3-carboxyphenyl, 4-carboxyphenyl, 5-carboxy-3-pyridyl, 4-carboxy-1-piperidyl, carboxymethyl, or carboxymethoxy, more preferably 3-carboxyphenyl, 4-carboxyphenyl, or 5-carboxy-3-pyridyl.

$Ar^1$ represents a group formed from an aromatic ring optionally having substituent(s) selected from $R^3$.

"Group formed from an aromatic ring" means an atomic group formed by removing the hydrogen atoms from the ring-constituting atoms of the aromatic ring. The group means at least 2-valent group necessarily bonding to the adjacent carbonyl group and the linking group A, and optionally it may have one or two or more substituents selected from R³, and it may be 3- or 4-valent or more poly-valent group bonding to the substituent. One or two or more substituents selected from the adjacent carbonyl group, the linking group A and R³ may independently bond to any bondable position on Ar¹.

The aromatic ring itself for Ar¹ is, for example, preferably a benzene ring, a pyrazole ring, an isoxazole ring, a pyridine ring, an indole ring, a 1H-indazole ring, a 2H-indazole ring, a 1H-furo[2,3-c]pyrazole ring, a 1H-thieno[2,3-c]pyrazole ring, a benzo[b]furan ring, a benzimidazole ring, a benzoxazole ring, a 1,2-benzisoxazole ring, an imidazo[1,2-a]pyridine ring, an imidazo[1,5-a]pyridine ring, a 1H-pyrazolo[3,4-b]pyridine ring, a quinoline ring, an isoquinoline ring, a phthalazine ring, a 1,5-naphthyridine ring, a 1,6-naphthyridine ring, a 1,7-naphthyridine ring, a 1,8-naphthyridine ring, a 2,6-naphthyridine ring, a 2,7-naphthyridine ring, a quinoxaline ring, a quinazoline ring or a cinnoline ring, more preferably a benzene ring, an indole ring, a 1H-indazole ring or a quinoline ring.

Preferred embodiments of A and Ar¹ are that A is a linking group formed from a carbo- or heterocyclic ring selected from a group consisting of a benzene ring, a furan ring, a thiophene ring, a pyrazole ring, a thiazole ring, an oxazole ring, an isoxazole ring, a 1,2,4-triazole ring, a 1,2,4-oxadiazole ring, a 1,3,4-oxadiazole ring, a tetrazole ring, a pyridine ring, a pyrazine ring, a pyrimidine ring, an indole ring, a benzo[b]thiophene ring, a piperidine ring, a piperazine ring, a morpholine ring and a thiomorpholine ring, optionally substituted with above-mentioned substituent(s), and Ar¹ is a group formed from an aromatic ring selected from a group consisting of a benzene ring, a pyrazole ring, an isoxazole ring, a pyridine ring, an indole ring, a 1H-indazole ring, a 2H-indazole ring, a 1H-furo[2,3-c]pyrazole ring, a 1H-thieno[2,3-c]pyrazole ring, a benzo[b]furan ring, a benzimidazole ring, a benzoxazole ring, a 1,2-benzisoxazole ring, an imidazo[1,2-a]pyridine ring, an imidazo[1,5-a]pyridine ring, a 1H-pyrazolo[3,4-b]pyridine ring, a quinoline ring, an isoquinoline ring, a phthalazine ring, a 1,5-naphthyridine ring, a 1,6-naphthyridine ring, a 1,7-naphthyridine ring, a 1,8-naphthyridine ring, a 2,6-naphthyridine ring, a 2,7-naphthyridine ring, a quinoxaline ring, a quinazoline ring and a cinnoline ring, optionally having substituent(s) selected from R³; and A is a linking group formed from a carbo- or heterocyclic ring selected from a group consisting of a benzene ring, a pyridine ring and a piperidine ring, optionally substituted with above-mentioned substituent(s), and Ar¹ is a group formed from an aromatic ring selected from a group consisting of a benzene ring, an indole ring, a 1H-indazole ring and a quinoline ring, optionally having substituent(s) selected from R³.

R³ represents a halogen atom, a nitro group, a cyano group, a hydroxyl group, a carboxyl group, a C2-C6 alkenyl group, a cyclo-C3-C6 alkyl group, or a group of —N(R$^e$)R$^f$; a phenoxy group, a C1-C6 alkoxy group, a C2-C7 alkoxycarbonyl group, a C1-C6 alkylthio group, a cyclo-C3-C6 alkyloxy group, a cyclo-C3-C6 alkyloxycarbonyl group, a cyclo-C3-C6 alkyl-C1-C6 alkoxy group, a cyclo-C3-C6 alkylthio group or a cyclo-C3-C6 alkyl-C1-C6 alkylthio group, optionally substituted with a halogen atom or a hydroxyl group, wherein the cyclo-C3-C6 alkyl group in the cyclo-C3-C6 alkyloxy group, the cyclo-C3-C6 alkyloxycarbonyl group, the cyclo-C3-C6 alkyl-C1-C6 alkoxy group, the cyclo-C3-C6 alkylthio group or the cyclo-C3-C6 alkyl-C1-C6 alkylthio group may be interrupted by an oxygen atom, a sulfur atom or an imino group;

a C1-C6 alkyl group optionally having substituent(s) selected from a group consisting of a halogen atom, a hydroxyl group, a cyclo-C3-C6 alkyl group and a C1-C6 alkoxy group; or a phenyl group, a 1,2,4-triazolyl group or a tetrazolyl group optionally having substituent(s) selected from a group consisting of a halogen atom, a nitro group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group and a C1-C6 alkylthio group. For Ar¹, if desired, one or two or more, the same or different substituents are selected from these groups.

The halogen atom for R³ is, for example, preferably a fluorine atom, a chlorine atom.

The C2-C6 alkenyl group for R³ is, for example, preferably a vinyl group, a 2-propenyl group.

The cyclo-C3-C6 alkyl group for R³ is, for example, preferably a cyclopropyl group.

In the group of —N(R$^e$)R$^f$ for R³, R$^e$ and R$^f$ each independently represent a hydrogen atom, a C1-C6 alkyl group or a halo-C1-C6 alkyl group, or R$^e$ and R$^f$ can be taken together to form a C2-C5 alkylene group optionally interrupted by an oxygen atom, a sulfur atom or an imino group.

The C1-C6 alkyl group for R$^e$ and R$^f$ is, for example, preferably a methyl group an ethyl group.

The halo-C1-C6 alkyl group for R$^e$ and R$^f$ is, for example, preferably a fluoromethyl group, a difluoromethyl group.

The C2-C5 alkylene group optionally interrupted by an oxygen atom, a sulfur atom or an imino group, which is formed by R$^e$ and R$^f$ taken together, is for example, preferably a tetramethylene group, a pentamethylene group, a 3-oxapentamethylene group. The group forms, along with the adjacent nitrogen atom, a 1-pyrrolidinyl group, a piperidino group, a morpholino group.

Preferably, for example, R$^e$ and R$^f$ each are a C1-C6 alkyl group, or taken together to form the above-mentioned C2-C5 alkylene group.

Accordingly, the group of —N(R$^e$)R$^f$ is, for example, more concretely a dimethylamino group, a 1-prrolidinyl group, or a morpholino group.

In "a phenoxy group, a C1-C6 alkoxy group, a C2-C7 alkoxycarbonyl group, a C1-C6 alkylthio group, a cyclo-C3-C6 alkyloxy group, a cyclo-C3-C6 alkyloxycarbonyl group, a cyclo-C3-C6 alkyl-C1-C6 alkoxy group, a cyclo-C3-C6 alkylthio group or a cyclo-C3-C6 alkyl-C1-C6 alkylthio group, optionally substituted with a halogen atom or a hydroxyl group, wherein the cyclo-C3-C6 alkyl group in the cyclo-C3-C6 alkyloxy group, the cyclo-C3-C6 alkyloxycarbonyl group, the cyclo-C3-C6 alkyl-C1-C6 alkoxy group, a cyclo-C3-C6 alkylthio group or the cyclo-C3-C6 alkyl-C1-C6 alkylthio group may be interrupted by an oxygen atom, a sulfur atom or an imino group" for R³, the halogen atom for the substituent is, for example, preferably a fluorine atom, a chlorine atom.

The C1-C6 alkoxy group optionally substituted with a halogen atom or a hydroxyl group for R3 is, for example, preferably a methoxy group, an ethoxy group, a propoxy group, an isopropoxy group, a difluoromethoxy group, a 2,2-difluoroethoxy group, a 2-hydroxyethoxy group, more preferably a methoxy group, an ethoxy group, particularly an ethoxy group.

The C2-C7 alkoxycarbonyl group optionally substituted with a halogen atom or a hydroxyl group for R³ is, for example, preferably a methoxycarbonyl group, an ethoxycarbonyl group, a propoxycarbonyl group, an isopropoxycarbonyl group, a difluoromethoxycarbonyl group, a 2,2-difluoroethoxycarbonyl group, a 2-hydroxyethoxycarbonyl group, more preferably a methoxycarbonyl group, an ethoxycarbonyl group.

The C1-C6 alkylthio group optionally substituted with a halogen atom or a hydroxyl group for $R^3$ is, for example, preferably a methylthio group, an ethylthio group, a difluoromethylthio group, a 2-hydroxyethylthio group.

The cyclo-C3-C6 alkyloxy group optionally substituted with a halogen atom or a hydroxyl group for $R^3$ is, for example, preferably a cyclopropyloxy group, a cyclobutyloxy group, a 3-tetrahydrofuranyloxy group.

The cyclo-C3-C6 alkyloxycarbonyl group optionally substituted with a halogen atom or a hydroxyl group for R3 is, for example, preferably a cyclopropyloxycarbonyl group, a cyclobutyloxycarbonyl group, a 3-tetrahydrofuranyloxycarbonyl group.

The cyclo-C3-C6 alkyl-C1-C6 alkoxy group optionally substituted with a halogen atom or a hydroxyl group for $R^3$ is, for example, preferably a cyclopropylmethoxy group, a 3-tetrahydrofuranylmethoxy group.

The cyclo-C3-C6 alkylthio group optionally substituted with a halogen atom or a hydroxyl group for $R^3$ is, for example, preferably a cyclopropylthio group, a 3-tetrahydrothienylthio group.

The cyclo-C3-C6 alkyl-C1-C6 alkylthio group optionally substituted with a halogen atom or a hydroxyl group for $R^3$ is, for example, preferably a cyclopropylmethylthio group, a 3-tetrahydrothienylmethylthio group.

Of the phenoxy group, the C1-C6 alkoxy group, the C2-C7 alkoxycarbonyl group, the C1-C6 alkylthio group, the cyclo-C3-C6 alkyloxy group, the cyclo-C3-C6 alkyloxycarbonyl group, the cyclo-C3-C6 alkyl-C1-C6 alkoxy group, the cyclo-C3-C6 alkylthio group or the cyclo-C3-C6 alkyl-C1-C6 alkylthio group, optionally substituted with a halogen atom or a hydroxyl group, for $R^3$, for example, preferred is the C1-C6 alkoxy group or the cyclo-C3-C6 alkyloxy group optionally substituted with a halogen atom or a hydroxyl group, more preferred is the C1-C6 alkoxy group optionally substituted with a halogen atom or a hydroxyl group.

"C1-C6 alkyl group optionally having substituent(s) selected from a group consisting of a halogen atom, a hydroxyl group, a cyclo-C3-C6 alkyl group and a C1-C6 alkoxy" for $R^3$ means the above-mentioned, unsubstituted C1-C6 alkyl group, or the above-mentioned C1-C6 alkyl group having the substituent at any substitutable position thereof, in which the substituent is one or two or more, preferably one or two, the same or different groups selected from a halogen atom, a hydroxyl group, a cyclo-C3-C6 alkyl group and a C1-C6 alkoxy group.

The halogen atom for the substituent is, for example, preferably a fluorine atom, a chlorine atom.

The cyclo-C3-C6 alkyl group for the substituent is, for example, preferably a cyclopropyl group.

The C1-C6 alkoxy group for the substituent is, for example, preferably a methoxy group, an ethoxy group.

The C1-C6 alkyl group optionally having the substituent for $R^3$ is, for example, preferably a methyl group, an ethyl group, an isopropyl group, a fluoromethyl group, a difluoromethyl group, a trifluoromethyl group, a 2-fluoroethyl group, a 2,2-difluoroethyl group, a hydroxymethyl group, a 2-hydroxyethyl group, a cyclopropylmethyl group, a methoxymethyl group, more preferably a methyl group.

"A phenyl group, a 1,2,4-triazolyl group, or a tetrazolyl group optionally having substituent(s) selected from a group consisting of a halogen atom, a nitro group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group and a C1-C6 alkylthio group" for $R^3$ means an unsubstituted phenyl, 1,2,4-triazolyl or tetrazolyl group, or a phenyl, 1,2,4-triazolyl or tetrazolyl group having the substituent at the substitutable position thereof, in which the substituent is one or two or more, preferably one or two, the same or different groups selected from a halogen atom, a nitro group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group and a C1-C6 alkylthio group.

The halogen atom for the substituent is, for example, preferably a fluorine atom, a chlorine atom.

The C1-C6 alkyl group for the substituent is, for example, preferably a methyl group, an ethyl group.

The halo-C1-C6 alkyl group for the substituent is, for example, preferably a fluoromethyl group, a difluoromethyl group, a 2,2-difluoroethyl group.

The hydroxy-C1-C6 alkyl group for the substituent is, for example, preferably a hydroxymethyl group, a 2-hydroxyethyl group.

The cyclo-C3-C6 alkyl group for the substituent is, for example, preferably a cyclopropyl group.

The C2-C6 alkenyl group for the substituent is, for example, preferably a vinyl group, a 2-propenyl group, an isopropenyl group.

The C1-C6 alkoxy group for the substituent is, for example, preferably a methoxy group, an ethoxy group, an isopropoxy group.

The halo-C1-C6 alkoxy group for the substituent is, for example, preferably a fluoromethoxy group, a difluoromethoxy group, a 2,2-difluoroethyl group.

The C1-C6 alkylthio group for the substituent is, for example, preferably a methylthio group, an ethylthio group, an isopropylthio group.

The substituent is, for example, preferably a halogen atom, a C1-C6 alkyl group, a C1-C6 alkoxy group.

The optionally-substituted phenyl group includes, for example, a phenyl group, a 2-fluorophenyl group, a 3-fluorophenyl group, a 4-fluorophenyl group, a 2-chlorophenyl group, a 3-chlorophenyl group, a 4-chlorophenyl group, a 4-bromophenyl group, a 4-methylphenyl group, a 4-methoxyphenyl group, a 4-ethoxyphenyl group. Of those, preferred are a phenyl group, a 2-fluorophenyl, group, a 3-fluorophenyl group, a 4-fluorophenyl group, a 4-chlorophenyl group, a 4-methoxyphenyl group.

The optionally-substituted 1,2,4-triazolyl group is, for example, preferably a 1,2,4-triazol-3-yl group.

The optionally-substituted tetrazolyl group is, for example, preferably a 5-tetrazolyl group.

$R^3$ is, for example, preferably a halogen atom, a cyclo-C3-C6 alkyl group or a group of —N($R^e$)$R^f$; or a C1-C6 alkoxy group or a cyclo-C3-C6 alkyl group optionally substituted with a halogen atom or a hydroxyl group; or the above-mentioned, optionally-substituted C1-C6 alkyl group; or a phenyl group, a 1,2,4-triazolyl group or a tetrazolyl group optionally substituted with a halogen atom, a nitro group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group and a C1-C6 alkylthio group, more preferably a cyclo-C3-C6 alkyl group; a C1-C6 alkoxy group optionally substituted with a halogen atom or a hydroxyl group; or the above-mentioned, optionally-substituted C1-C6 alkyl group.

Accordingly, in the compounds of the invention, the group of the following formula:

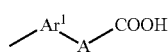

is preferably formed through combination of the above-mentioned preferred groups; for example, it is preferably a 2'-carboxy-2,6-diethoxy-4-biphenylyl group, a 3'-carboxy-2,6-diethoxy-4-biphenylyl group, a 4'-carboxy-2,6-diethoxy-4-biphenylyl group, a 3'-carboxy-4'-fluoro-2,6-diethoxy-4-biphenylyl group, a 4'-carboxy-3'-fluoro-2,6-diethoxy-4-biphenylyl group, a 4-(5-carboxy-3-pyridyl)-3,5-diethoxyphenyl group, a 4-(2-carboxyphenyl)-1-cyclopropylindol-6-yl group, a 4-(3-carboxyphenyl)-1-cyclopropylindol-6-yl group, a 4-(4-carboxyphenyl)-1-cyclopropylindol-6-yl group, a 4-(4-carboxyphenyl)-1-cyclopropyl-3-methylindol-6-yl group, a 4-(4-carboxy-1-piperidyl)-1-cyclopropylindol-6-yl group, a 4-carboxymethoxy-1-cyclopropylindol-6-yl group, a 1-(2-carboxyphenyl)-3-methyl-1H-indazol-5-yl group, a 1-(3-carboxyphenyl)-3-methyl-1H-indazol-5-yl group, a 1-(4-carboxyphenyl)-3-methyl-1H-indazol-5-yl group, a 1-(4-carboxyphenyl)-3-methyl-1H-indazol-5-yl group, a 1-carboxymethyl-3-methyl-1H-indazol-5-yl group, a 1-(2-carboxyphenyl)-3-methyl-1H-indazol-6-yl group, a 1-(3-carboxyphenyl)-3-methyl-1H-indazol-6-yl group, a 1-carboxymethyl-3-methyl-1H-indazol-6-yl group, or a 4-(4-carboxyphenyl)-8-cyclopropyl-2-quinolyl group, more preferably 2'-carboxy-2,6-diethoxy-4-biphenylyl group, a 3'-carboxy-2,6-diethoxy-4-biphenylyl group, a 4'-carboxy-2,6-diethoxy-4-biphenylyl group, a 3'-carboxy-4'-fluoro-2,6-diethoxy-4-biphenylyl group, a 4'-carboxy-3'-fluoro-2,6-diethoxy-4-biphenylyl group, a 4-(5-carboxy-3-pyridyl)-3,5-diethoxyphenyl group, a 4-(2-carboxyphenyl)-1-cyclopropylindol-6-yl group, a 4-(3-carboxyphenyl)-1-cyclopropylindol-6-yl group, a 4-(4-carboxyphenyl)-1-cyclopropylindol-6-yl group, a 4-(4-carboxyphenyl)-1-cyclopropyl-3-methylindol-6-yl group, a 1-(3-carboxyphenyl)-3-methyl-1H-indazol-5-yl group, a 1-(4-carboxyphenyl)-3-methyl-1H-indazol-5-yl group, a 1-(4-carboxyphenyl)-3-methyl-1H-indazol-5-yl group, a 1-(3-carboxyphenyl)-3-methyl-1H-indazol-6-yl group, or a 4-(4-carboxyphenyl)-8-cyclopropyl-2-quinolyl group.

$R^1$ and $R^2$ each independently represent a hydrogen atom, a halogen atom, a cyano group, a C2-C6 alkenyl group, a C1-C6 alkoxy group, a halo-C1-C6 alkoxy group, a cyclo-C3-C6 alkyloxy group, a C2-C7 alkanoyl group, a halo-C2-C7 alkanoyl group, a C2-C7 alkoxycarbonyl group, a halo-C2-C7 alkoxycarbonyl group, a cyclo-C3-C6 alkyloxycarbonyl group, an aralkyloxycarbonyl group, a carbamoyl-C1-C6 alkoxy group, a carboxy-C2-C6 alkenyl group, or a group of -$Q^1$-N($R^a$)-$Q^2$-$R^b$;

a C1-C6 alkyl group optionally having substituent(s) selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group;

an aryl or heterocyclic group optionally having substituent(s) selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$; or a C1-C6 alkyl group or a C2-C6 alkenyl group having the aryl or heterocyclic group.

The halogen atom for $R^1$ and $R^2$ is, for example, preferably a chlorine atom, a bromine atom.

The C2-C6 alkenyl group for $R^1$ and $R^2$ is, for example, preferably a 2-propenyl group, an isopropenyl group.

The C1-C6 alkoxy group for $R^1$ and $R^2$ is, for example, preferably a methoxy group, an ethoxy group, a propoxy group.

The halo-C1-C6 alkoxy group for $R^1$ and $R^2$ is, for example, preferably a fluoromethoxy group, a difluoromethoxy group.

The C2-C7 alkanoyl group for $R^1$ and $R^2$ is, for example, preferably an acetyl group, a propionyl group.

The halo-C2-C7 alkanoyl group for $R^1$ and $R^2$ is, for example, preferably a difluoroacetyl group, a 3-fluoropropionyl group.

The C2-C7 alkoxycarbonyl group for $R^1$ and $R^2$ is, for example, preferably a methoxycarbonyl group, an ethoxycarbonyl group.

The halo-C2-C7 alkoxycarbonyl group for $R^1$ and $R^2$ is, for example, preferably a fluoromethoxycarbonyl group, a difluoromethoxycarbonyl group.

The cyclo-C3-C6 alkyloxycarbonyl group for $R^1$ and $R^2$ is, for example, preferably a cyclopropyloxycarbonyl group.

The aralkyloxycarbonyl group for $R^1$ and $R^2$ is, for example, preferably a benzyloxycarbonyl group.

The carbamoyl-C1-C6 alkoxy group for $R^1$ and $R^2$ is, for example, preferably a carbamoylmethoxy group, a 2-carbamoylethoxy group.

The carboxy-C2-C6 alkenyl group for $R^1$ and $R^2$ is, for example, preferably a 2-carboxyvinyl group, a 3-carboxy-1-propenyl group, a 3-carboxy-2-propenyl group.

In the group of -$Q^1$-N($R^a$)-$Q^2$-$R^b$ for $R^1$ and $R^2$, $Q^1$ and $Q^2$ each independently represent a single bond, or a group of —CO—, —SO$_2$— or —C($R^g$)($R^h$)—; $R^a$ and $R^b$ each independently represent a hydrogen atom, a C2-C6 alkenyl group, a C1-C6 alkoxy group, a cyclo-C3-C6 alkyloxy group, a halo-C1-C6 alkoxy group, a cyclo-C3-C6 alkyl group, an aralkyloxy group, a carbamoyl group, a C2-C7 alkoxycarbonyl group, or a group of —N($R^i$)$R^j$; a C1-C6 alkyl group optionally having substituent(s) selected from a group consisting of a halogen atom, a C1-C6 alkoxy group, a carbamoyl group and a C2-C7 alkoxycarbonyl group; or a heteroaromatic group optionally substituted with a C1-C6 alkyl group optionally having substituent(s) selected from a group consisting of a halogen atom, a C1-C6 alkoxy group, a carbamoyl group and a C2-C7 alkoxycarbonyl group.

In the group of —C($R^g$)($R^h$)— for $Q^1$ and $Q^2$, $R^g$ and $R^h$ each independently represent a hydrogen atom, a C1-C6 alkyl group, or a halo-C1-C6 alkyl group.

$R^g$ and $R^h$ are, for example, preferably a hydrogen atom, a methyl group, an ethyl group.

$Q^1$ is, for example, preferably a single bond, or a group of —CO— or —C($R^g$)($R^h$)—; and $Q^2$ is, for example, preferably a single bond, or a group of —CO— or —C($R^g$)($R^h$)—. The group of —C($R^g$)($R^h$)— for $Q^1$ is more preferably —C(CH$_3$)$_2$—; and the group of —C($R^g$)($R^h$)— for $Q^2$ is more preferably —CH$_2$—.

The C2-C6 alkenyl group for $R^a$ and $R^b$ is, for example, preferably a vinyl group, a 2-propenyl group.

The cyclo-C3-C6 alkyloxy group for $R^a$ and $R^b$ is, for example, preferably a cyclopropyloxy group.

The C1-C6 alkoxy group for $R^a$ and $R^b$ is, for example, preferably a methoxy group, an ethoxy group.

The halo-C1-C6 alkoxy group for $R^a$ and $R^b$ is, for example, preferably a fluoromethoxy group, a difluoromethoxy group, a trifluoromethoxy group, a chloromethoxy group, a dichloromethoxy group.

The cyclo-C3-C6 alkyl group for $R^a$ and $R^b$ is, for example, preferably a cyclopropyl group.

The aralkyloxy group for $R^a$ and $R^b$ is, for example, preferably a benzyloxy group.

The C2-C7 alkoxycarbonyl group for $R^a$ and $R^b$ is, for example, preferably a methoxycarbonyl group, an ethoxycarbonyl group, a tert-butoxycarbonyl group.

In the group of —N($R^i$)$R^j$ for $R^a$ and $R^b$, $R^i$ and $R_j$ each independently represent a hydrogen atom, a C1-C6 alkyl group or a halo-C1-C6 alkyl group.

$R^i$ and $R^j$ are, for example, preferably a hydrogen atom, a methyl group or a 2,2,2-trifluoroethyl group.

The group of —N($R^i$)$R^j$ for $R^a$ and $R^b$ is, for example, preferably an amino group, a dimethylamino group, or a 2,2,2-trifluoroethylamino group.

"C1-C6 alkyl group optionally having substituent(s) selected from a group consisting of a halogen atom, a C1-C6 alkoxy group, a carbamoyl group and a C2-C7 alkoxycarbonyl group" for $R^a$ and $R^b$ means the above-mentioned unsubstituted C1-C6 alkyl group, or the above-mentioned C1-C6 alkyl group having substituent(s) at any substitutable position thereof, in which the substituent may be the same or different, one or two or more, preferably from 1 to 3 substituents selected from a group consisting of a halogen atom, a C1-C6 alkoxy group, a carbamoyl group and a C2-C7 alkoxycarbonyl group.

The halogen atom for the substituent is, for example, preferably a fluorine atom, a chlorine atom.

The C1-C6 alkoxy group for the substituent is, for example, preferably a methoxy group, an ethoxy group.

The C2-C7 alkoxycarbonyl group for the substituent is, for example, preferably a methoxycarbonyl group, an ethoxycarbonyl group, a tert-butoxycarbonyl group.

The substituent is, for example, preferably a halogen atom, a carbamoyl group, a C2-C7 alkoxycarbonyl group.

"C1-C6 alkyl group" itself of the above-mentioned, optionally-substituted C1-C6 alkyl group for $R^a$ and $R^b$ is, for example, preferably a methyl group, an ethyl group, a propyl group, an isopropyl group.

The above-mentioned, optionally-substituted C1-C6 alkyl group for $R^a$ and $R^b$ is, for example, preferably a methyl group, a difluoromethyl group, a trifluoromethyl group, a methoxymethyl group, a carbamoylmethyl group, a tert-butoxycarbonylmethyl group, an ethyl group, a propyl group, an isopropyl group.

"Heteroaromatic group optionally substituted with a C1-C6 alkyl group optionally having substituent(s) selected from a group consisting of a halogen atom, a C1-C6 alkoxy group, a carbamoyl group and a C2-C7 alkoxycarbonyl group" for $R^a$ and $R^b$ means the above-mentioned, unsubstituted heteroaromatic group, or the above-mentioned heteroaromatic group having "a C1-C6 alkyl group optionally having substituent(s) selected from a group consisting of a halogen atom, a C1-C6 alkoxy group, a carbamoyl group and a C2-C7 alkoxycarbonyl group" as substituent(s) at any substitutable position thereof, in which the substituent on the heteroaromatic group may be the same or different, one or two or more, preferably one or two selected from them.

Preferred examples of the substituent on the heteroaromatic group, "C1-C6 alkyl group optionally having substituent(s) selected from a group consisting of a halogen atom, a C1-C6 alkoxy group, a carbamoyl group and a C2-C7 alkoxycarbonyl group" may be the same as those mentioned hereinabove for the "optionally-substituted C1-C6 alkyl group" for $R^a$ and $R^b$.

"Heteroaromatic group" itself of the heteroaromatic group optionally substituted with the above-mentioned, optionally-substituted C1-C6 alkyl group for $R^a$ and $R^b$ is, for example, preferably a pyrrolyl group, a pyrazolyl group, an isoxazolyl group, a 1,2,4-triazolyl group, a pyrimidinyl group.

The heteroaromatic group optionally substituted with the above-mentioned, optionally-substituted C1-C6 alkyl group for $R^a$ and $R^b$ is, for example, preferably a 2-pyrrolyl group, a 1-methyl-2-pyrrolyl group, a 3-pyrazolyl group, a 1-methyl-3-pyrazolyl group, a 2-methyl-3-pyrazolyl group, a 2,5-dimethyl-3-pyrazolyl group, a 2-ethyl-3-pyrazolyl group, a 2-methoxymethyl-3-pyrazolyl group, a 5-methyl-3-isoxazolyl group, a 1,2,4-triazol-3-yl group, a 1-methyl-1,2,4-triazol-3-yl group, a 2-methyl-1,2,4-triazol-3-yl group, a 2-pyrimidinyl group, a 5-pyrimidinyl group.

$R^a$ and $R^b$ are, for example, preferably a hydrogen atom, a C1-C6 alkoxy group, an aralkyloxy group, a carbamoyl group, a C2-C7 alkoxycarbonyl group, a group of —N($R^i$)$R^j$, a C1-C6 alkyl group optionally having the above-mentioned substituent, or a heteroaromatic group optionally substituted with the above-mentioned, optionally-substituted C1-C6 alkyl group.

The group of -$Q^1$-N($R^a$)-$Q^2$-$R^b$ of $R^1$ and $R^2$ is, for example, preferably such that $Q^1$ and $Q^2$ are a single bond, $R^a$ is a hydrogen atom, and $R^b$ is a heteroaromatic group optionally substituted with a C1-C6 alkyl group optionally having substituent(s) selected from a group consisting of a halogen atom, a C1-C6 alkoxy group, a carbamoyl group and a C2-C7 alkoxycarbonyl group; more preferably, it is a 2-methyl-3-pyrazolylamino group; or such that $Q^1$ is a group of —CO—, $Q^2$ is a group of —C($R^g$)($R^h$)—, $R^a$ is a hydrogen atom, and $R^b$ is a carbamoyl group; or such that $Q^1$ is a group of —CO—, $Q^2$ is a group of —C($R^g$)($R^h$)—, $R^a$ is a hydrogen atom, and $R^b$ is a C1-C6 alkyl group optionally having substituent(s) selected from a group consisting of a halogen atom, a C1-C6 alkoxy group, a carbamoyl group and a C2-C7 alkoxycarbonyl group.

Examples of the group of -$Q^1$-N($R^a$)-$Q^2$-$R^b$ for $R^1$ and $R^2$ include, for example, an isopropylamino group, a formylamino group, an acetylamino group, a methoxycarbonylamino group, a benzyloxycarbonylamino group, a carbamoylamino group, a 2,2,2-trifluoroethylcarbamoylamino group, a 2-pyrrolylcarbonylamino group, a 1-methyl-2-pyrrolylcarbonylamino group, a 3-pyrazolylamino group, a 1-methyl-3-pyrazolylamino group, a 2-methyl-3-pyrazolylamino group, a 2,5-dimethyl-3-pyrazolylamino group, a 2-ethyl-3-pyrazolylamino group, a 2-methoxymethyl-3-pyrazolylamino group, an N-methyl-N-(2-methyl-3-pyrazolyl)amino group, a 5-methyl-3-isoxazolylamino group, a 1,2,4-triazol-3-ylamino group, a 1-methyl-1,2,4-triazol-3-ylamino group, a 2-methyl-1,2,4-triazol-3-ylamino group, a 2-pyridinylamino group, a 5-pyridinylamino group, a carbamoyl group, a methylcarbamoyl group, a 2,2-difluoroethylcarbamoyl group, a 2,2,2-trifluoroethylcarbamoyl group, a (carbamoylmethyl)carbamoyl group, a (2-carbamoylethyl)carbamoyl group, a (1-carbamoyl-1-methylethyl)carbamoyl group, a (1-tert-butoxycarbonyl-1-methylethyl)carbamoyl group, a (2-tert-butoxycarbonylethyl)carbamoyl group, an aminosulfonyl group, a methylaminosulfonyl group, a dimethylaminosulfonyl group, an ethylaminosulfonyl group, a propylaminosulfonyl group, a butylaminosulfonyl group, an N-acetyl-N-methylaminosulfonyl group, an N-acetyl-N-ethylaminosulfonyl group, an N-acetyl-N-propylaminosulfonyl group, a 1-amino-1-methylethyl group, a 1-acetylamino-1-methylethyl group, a 1-(benzyloxycarbonylamino)-1-methylethyl group. Of those, for example, preferred are a 1-methyl-3-pyrazolylamino group, a 2-methyl-3-pyrazolylamino group, a 2,5-dimethyl-3-pyrazolylamino group, a 5-methyl-3-isoxazolylamino group, a carbamoyl group, a 2,2,2-trifluoroethylcarbamoyl group, a (carbamoylmethyl) carbamoyl group; more preferred is a 2-methyl-3-pyrazolylamino group.

"C1-C6 alkyl group optionally having substituent(s) selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group" for $R^1$ and $R^2$ means the above-mentioned unsubstituted C1-C6 alkyl group, or the above-mentioned C1-C6 alkyl group having the substituent at the substitutable position thereof, in which the substituent may be the same or different, one or two or more, preferably from 1 to 3 groups selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group.

The halogen atom for the substituent is, for example, preferably a fluorine atom, a chlorine atom.

The C1-C6 alkoxy group for the substituent is, for example, preferably a methoxy group, an ethoxy group.

The halo-C1-C6 alkoxy group for the substituent is, for example, preferably a difluoromethoxy group.

The C1-C6 alkylthio group for the substituent is, for example, preferably a methylthio group, an ethylthio group.

The C2-C7 alkanoyloxy group for the substituent is, for example, preferably an acetyloxy group, a propionyloxy group.

The C2-C7 alkoxycarbonyl group for the substituent is, for example, preferably a methoxycarbonyl group, an ethoxycarbonyl group.

The C1-C6 alkylsulfonyl group for the substituent is, for example, preferably a methylsulfonyl group, an ethylsulfonyl group.

The substituent is, for example, preferably a halogen atom, a hydroxyl group, a carboxyl group, a carbamoyl group, a C2-C7 alkoxycarbonyl group.

"C1-C6 alkyl group" itself of the above-mentioned, optionally-substituted C1-C6 alkyl group for $R^1$ and $R^2$ is, for example, preferably a methyl group, an ethyl group, a propyl group, an isopropyl group, a tert-butyl group.

The above-mentioned, optionally-substituted C1-C6 alkyl group for $R^1$ and $R^2$ is, for example, preferably a methyl group, a fluoromethyl group, a hydroxymethyl group, an azidomethyl group, a methoxymethyl group, a methylthiomethyl group, an acetyloxymethyl group, a methoxycarbonylmethyl group, a methylsulfonylmethyl group, an ethyl group, a 1-hydroxyethyl group, a 1-carboxy-1-methylethyl group, a 1-carbamoyl-1-methylethyl group, a 1-methoxycarbonyl-1-methylethyl group, a propyl group, an isopropyl group, a tert-butyl group.

"Aryl or heterocyclic group optionally having substituent (s) selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$" for $R^1$ and $R^2$ means the above-mentioned unsubstituted aryl or heterocyclic group, or the above-mentioned aryl or heterocyclic group having the substituent at the substitutable position thereof, in which the substituent may be the same or different, one or two or more, preferably one or two groups selected from a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$.

The halogen atom for the substituent is, for example, preferably a fluorine atom, a chlorine atom.

The C1-C6 alkyl for the substituent is, for example, preferably a methyl group, an ethyl group, more preferably a methyl group.

The halo-C1-C6 alkyl group for the substituent is, for example, preferably a fluoromethyl group, a difluoromethyl group, a trifluoromethyl group.

The hydroxy-C1-C6 alkyl group for the substituent is, for example, preferably a hydroxymethyl group, a 1-hydroxyethyl group, a 2-hydroxyethyl group.

The C2-C7 alkanoyloxy-C1-C6 alkyl group for the substituent is, for example, preferably an acetyloxymethyl group, a pivaloyloxymethyl group.

The C1-C6 alkoxy group for the substituent is, for example, preferably a methoxy group, an ethoxy group.

The halo-C1-C6 alkoxy group for the substituent is, for example, preferably a difluoromethoxy group.

The C2-C7 alkanoyl group for the substituent is, for example, preferably an acetyl group, a propionyl group.

The C2-C7 alkoxycarbonyl group for the substituent is, for example, preferably a methoxycarbonyl group, an ethoxycarbonyl group.

The C1-C6 alkylsulfonyl group for the substituent is, for example, preferably a methylsulfonyl group.

In the group of —CO—N($R^c$)$R^d$ for the substituent, $R^c$ and $R^d$ each independently represent a hydrogen atom, a C1-C6 alkyl group or a halo-C1-C6 alkyl group.

The C1-C6 alkyl group for $R^c$ and $R^d$ is, for example, preferably a methyl group, an ethyl group.

The group of —CO—N($R^c$)$R^d$ for the substituent is, for example, preferably a carbamoyl group, a dimethylcarbamoyl group, more preferably a carbamoyl group.

The substituent is, for example, preferably an oxo group, a C1-C6 alkyl group, a formyl group, a carboxyl group, a C2-C7 alkoxycarbonyl group, a C1-C6 alkylsulfonyl group, a group of —CO—N($R^c$)$R^d$, more preferably a C1-C6 alkyl group or a group of —CO—N($R^c$)$R^d$.

"Aryl group" itself of the above-mentioned optionally-substituted aryl or heterocyclic group for $R^1$ and $R^2$ is, for example, preferably a phenyl group; "heterocyclic group" itself thereof is, for example, preferably a pyrrolyl group, an imidazolyl group, a pyrazolyl group, a 1,2,4-triazolyl group, a tetrazolyl group, a pyridyl group, a pyrimidinyl group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a dihydropyridyl group, a piperidyl group, a piperazinyl group, a morpholinyl group, a thiomorpholinyl group. Of those, more preferred is a pyrazolyl group or a pyridyl group.

The above-mentioned, optionally-substituted aryl or heterocyclic group for $R^1$ and $R^2$ is, for example, preferably a phenyl group optionally substituted with a halogen atom, a carboxyl group or a group of —CO—N($R^c$)$R^d$; a pyrazolyl group optionally substituted with a C1-C6 alkyl group; a 1,2,4-triazolyl group; a tetrazolyl group optionally substituted with a C2-C7 alkanoyloxy-C1-C6 alkyl group; a pyridyl group optionally substituted with a C1-C6 alkyl group, a C1-C6 alkoxy group, a carboxyl group, a C2-C7 alkoxycarbonyl group or a group of —CO—N(R$^c$)R$^d$; a pyrimidinyl group; a dihydro-1,2,4-triazolyl group optionally substituted with an oxo group; a dihydro-1,2,4-oxadiazolyl group optionally substituted with an oxo group; a dihydropyridyl group optionally substituted with an oxo group; a thiomorpholinyl group optionally substituted with an oxo group; or a piperazinyl group optionally substituted with a C2-C7 alkanoyl group. More preferred is a phenyl group optionally substituted with a group of —CO—N(R$^c$)R$^d$; a pyrazolyl group optionally substituted with a C1-C6 alkyl group; or a pyridyl group optionally substituted with a group of —CO—N(R$^c$)R$^d$.

Examples of the aryl group or the heterocyclic group for R$^1$ and R$^2$ include, for example, a phenyl group, a 3-carboxyphenyl group, a 3-carboxy-4-fluorophenyl group, a 3-carbamoylphenyl group, a 4-carbamoylphenyl group, a 1-pyrrolyl group, a 1-imidazolyl group, a 3-pyrazolyl group, a 4-pyrazolyl group, a 1-methyl-4-pyrazolyl group, a 1,2,4-triazol-3-yl group, a 1,2,4-triazol-4-yl group, a 5-carbamoyl-1,2,4-triazol-3-yl group, a 1-tetrazolyl group, a 5-tetrazolyl group, a 1-methyl-5-tetrazolyl group, a 2-methyl-5-tetrazolyl group, a 2-pivaloyloxymethyl-5-tetrazolyl group, a 2-dimethylcarbamoyl-5-tetrazolyl group, a 3-pyridyl group, a 6-methoxy-3-pyridyl group, a 5-methoxycarbonyl-3-pyridyl group, a 5-carboxy-3-pyridyl group, a 5-carboxy-6-methyl-3-pyridyl group, a 2-carboxy-4-pyridyl group, a 5-carboxy-2-pyridyl group, a 5-carbamoyl-2-pyridyl group, a 5-carbamoyl-3-pyridyl group, a 2-pyrimidinyl group, a 5-pyrimidinyl group, a 2-oxo-1-pyrrolidinyl group, a 5-oxo-4,5-dihydro-1,2,4-triazol-3-yl group, a 3-oxo-2,3-dihydro-1,2,4-triazol-4-yl group, a 5-oxo-4,5-dihydro-1,2,4-oxadiazol-3-yl group, a 5-thioxo-4,5-dihydro-1,2,4-oxadiazol-3-yl group, a 5-oxo-4,5-dihydro-1,3,4-oxadiazol-2-yl group, a 5-oxo-4,5-dihydro-1,2,4-thiadiazol-3-yl group, a 2-oxo-2,3-dihydro-1,2,3,5-oxathiadiazol-4-yl group, a 6-oxo-1,6-dihydro-3-pyridyl group, a 1-piperidyl group, a 4-oxo-1-piperidyl group, a 1-piperazinyl group, a 3-oxo-1-piperazinyl group, a 4-methyl-1-piperazinyl group, a 4-formyl-1-piperazinyl group, a 4-acetyl-1-piperazinyl group, a 4-methoxycarbonyl-1-piperazinyl group, a 4-carbamoyl-1-piperazinyl group, a 4-methylsulfonyl-1-piperazinyl group, a 4-morpholinyl group, a 1,1-dioxo-4-thiomorpholinyl group. Of those, preferred are a 3-carbamoylphenyl group, a 4-carbamoylphenyl group, a 3-pyrazolyl group, or a 1-methyl-4-pyrazolyl group.

"C1-C6 alkyl or C2-C6 alkenyl group having the aryl or heterocyclic group" for R$^1$ and R$^2$ means a C1-C6 alkyl or C2-C6 alkenyl group having the same or different, one or two or more, preferably one aryl or heterocyclic group selected from the above-mentioned "aryl or heterocyclic group optionally having substituent(s) selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N(R$^c$)R$^d$", and is, for example, preferably a 5-tetrazolylmethyl group, a 2-(5-tetrazolyl)ethyl group, a 2-(5-tetrazolyl)vinyl group, a 3-(5-tetrazolyl)-1-propenyl group.

Preferred embodiments of R$^1$ and R$^2$ are, for example, such that R$^1$ is a hydrogen atom, a halogen atom, a cyano group, a C2-C6 alkenyl group, a C1-C6 alkoxy group, a halo-C1-C6 alkoxy group, a cyclo-C3-C6 alkyloxy group, a C2-C7 alkanoyl group, a halo-C2-C7 alkanoyl group, a C2-C7 alkoxycarbonyl group, a halo-C2-C7 alkoxycarbonyl group, a cyclo-C3-C6 alkyloxycarbonyl group, an aralkyloxycarbonyl group, a carbamoyl-C1-C6 alkoxy group, a carboxy-C2-C6 alkenyl group or a group of -Q$^1$-N(R$^a$)-Q$^2$-R$^b$;

a C1-C6 alkyl group optionally having substituent(s) selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group;

an aryl or heterocyclic group optionally having substituent(s) selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N(R$^c$)R$^d$; or a C1-C6 alkyl group or a C2-C6 alkenyl group having the aryl or heterocyclic group; and R$^2$ is a hydrogen atom, a halogen atom, a C1-C6 alkyl group or a C1-C6 alkoxy group.

R$^1$ is, for example, preferably an aryl or heterocyclic group optionally having substituent(s) selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N(R$^c$)R$^d$.

T and U each independently represent a nitrogen atom or a methine group. In case where T or U is a methine group, the methine group may be substituted with R$^1$ or R$^2$.

T and U are preferably a methine group.

V represents an oxygen atom, a sulfur atom or an imino group, and is preferably an oxygen atom.

In the compounds of formula (I), R$^1$ and R$^2$ may be positioned at any substitutable position of the skeleton of the following formula:

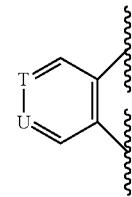

Preferred embodiments of the compounds of formula (I) are, for example, compounds of a general formula (I-1):

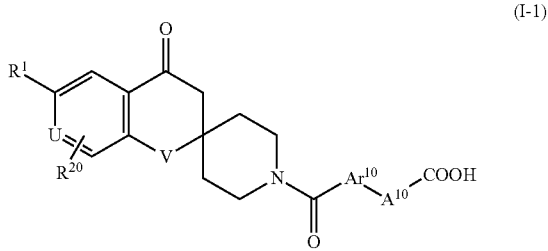

(I-1)

wherein $A^{10}$ represents a linking group formed from a carbo- or heterocyclic ring selected from a group consisting of a benzene ring, a furan ring, a thiophene ring, a pyrazole ring, a thiazole ring, an oxazole ring, an isoxazole ring, a 1,2,4-triazole ring, a 1,2,4-oxadiazole ring, a 1,3,4-oxadiazole ring, a tetrazole ring, a pyridine ring, a pyrazine ring, a pyrimidine ring, an indole ring, a benzo[b]thiophene ring, a piperidine ring, a piperazine ring, a morpholine ring and a thiomorpholine ring, or formed from a hydrocarbon chain selected from a C1-C6 alkane chain, a C2-C6 alkene chain and a C2-C6 alkyne chain, said hydrocarbon chain may be interrupted by an oxygen atom, a sulfur atom or an imino group, in which said linking group optionally has substituent(s) selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a C2-C7 alkanoylamino group, a C1-C6 alkylcarbamoyl group, a cyclo-C3-C6 alkylcarbamoyl group, a (C1-C6 alkoxy-C1-C6 alkyl)carbamoyl group, a C2-C7 alkoxycarbonyl group, a C1-C6 alkylsulfonyl group, a C1-C6 alkylsulfonylamino group and a tetrazolyl group; $Ar^{10}$ represents a group formed from an aromatic ring selected from a group consisting of a benzene ring, a pyrazole ring, an isoxazole ring, a pyridine ring, an indole ring, a 1H-indazole ring, a 2H-indazole ring, a 1H-furo[2,3-c]pyrazole ring, a 1H-thieno[2,3-c]pyrazole ring, a benzo[b]furan ring, a benzimidazole ring, a benzoxazole ring, a 1,2-benzisoxazole ring, an imidazo[1,2-a]pyridine ring, an imidazo[1,5-a]pyridine ring, a 1H-pyrazolo[3,4-b]pyridine ring, a quinoline ring, an isoquinoline ring, a phthalazine ring, a 1,5-naphthyridine ring, a 1,6-naphthyridine ring, a 1,7-naphthyridine ring, a 1,8-naphthyridine ring, a 2,6-naphthyridine ring, a 2,7-naphthyridine ring, a quinoxaline ring, a quinazoline ring and a cinnoline ring, optionally having substituent(s) selected from $R^3$; $R^{20}$ represents a hydrogen atom, a halogen atom, a C1-C6 alkyl group or a C1-C6 alkoxy group; and $R^1$, $R^3$ and U have the same meanings as above.

In formula (I-1), preferred embodiments of $A^{10}$, $Ar^{10}$, $R^1$ and U are the same as those of A, $Ar^1$, $R^1$ and U in formula (I). $R^{20}$ is preferably a hydrogen atom.

In one embodiment of the invention, a compound is illustrated by the above formula (I-1), wherein $A^{10}$ is a linking group formed from a carbo- or heterocyclic ring selected from a group consisting of a benzene ring, a pyridine ring and a piperidine ring, in which said linking group optionally has substituent(s) selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a C2-C7 alkanoylamino group, a C1-C6 alkylcarbamoyl group, a cyclo-C3-C6 alkylcarbamoyl group, a (C1-C6 alkoxy-C1-C6 alkyl)carbamoyl group, a C2-C7 alkoxycarbonyl group, a C1-C6 alkylsulfonyl group, a C1-C6 alkylsulfonylamino group and a tetrazolyl group; $Ar^{10}$ represents a group formed from an aromatic ring selected from a group consisting of a benzene ring, an indole ring, a 1H-indazole ring and a quinoline ring, optionally having substituent(s) selected from $R^3$; $R^1$ is an aryl or heterocyclic group optionally having substituent(s) selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$; $R^{20}$ is a hydrogen atom; U is a methine group; and $R^3$ has the same meanings as above.

In another embodiment of the invention, $R^1$ in the above embodiment is a phenyl group optionally substituted with a group of —CO—N($R^c$)$R^d$; a pyrazolyl group optionally substituted with a C1-C6 alkyl group; or a pyridyl group optionally substituted with a group of —CO—N($R^c$)$R^d$; $R^c$ and $R^d$ have the same meanings as above.

"A substitutable position" and "a bondable position" mean a position of a group at which the group has a chemically-substitutable hydrogen atom on the carbon atom, the nitrogen atom, the oxygen atom and/or the sulfur atom thereof, and the substitution gives a chemically-stable compound; or mean that a chemical bond gives a chemically-stable compound not resulting from the substitution of the type.

Depending on the type of the substituents therein and on the form of their salts, the compounds of the invention include stereoisomers and tautomers such as optical isomers, diastereoisomers and geometrical isomers, and the compounds of the invention encompass all these stereoisomers and tautomers and their mixtures.

The invention encompasses various crystals, amorphous phases, salts, hydrates and solvates of the compounds of the invention.

Further, prodrugs of the compounds of the invention are also within the scope of the invention. In general, such prodrugs are functional derivatives of the compounds of the invention, and they can be readily converted into the compounds that are needed in bodies. Accordingly, the term "administer" as referred to herein for the method of treating various disorders includes not only the administration of a specific compound but also the administration of a compound which, after administered to patients, may be converted into the specific compound in bodies. General methods for selection and production of suitable prodrug derivatives are described, for example, in *Design of Prodrugs*, ed. H. Bundgaard, Elsevier, 1985; and its entire description is referred to and incorporated herein as a part of the specification of the present application. Metabolites of these compounds include active compounds that are produced by leaving the compounds of the invention in a biological environment, and they are within a scope of the invention.

Specific examples of the compound of the invention are, for example, as follows:

(1) 4'-({6-(5-carbamoylpyridin-3-yl)-4-oxospiro[chroman-2,4'-piperidin]-1'-yl}carbonyl)-2',6'-diethoxybiphenyl-3-carboxylic acid;

(2) 2',6'-diethoxy-4'-{[6-(1H-pyrazol-5-yl)-4-oxospiro[chroman-2,4'-piperidin]-1'-yl]carbonyl}biphenyl-4-carboxylic acid;

(3) 4'-({6-(4-carbamoylphenyl)-4-oxospiro[chroman-2,4'-piperidin]-1'-yl}carbonyl)-2',6'-diethoxybiphenyl-4-carboxylic acid;

(4) 4'-({6-(3-carbamoylphenyl)-4-oxospiro[chroman-2,4'-piperidin]-1'-yl}carbonyl)-2',6'-diethoxybiphenyl-4-carboxylic acid;

(5) 4'-({6-(5-carbamoylpyridin-2-yl)-4-oxospiro[chroman-2,4'-piperidin]-1'-yl}carbonyl)-2',6'-diethoxybiphenyl-4-carboxylic acid;

(6) 4'-({6-(5-carbamoylpyridin-3-yl)-4-oxospiro[chroman-2,4'-piperidin]-1'-yl}carbonyl)-2',6'-diethoxybiphenyl-4-carboxylic acid;

(7) 4-(8-cyclopropyl-2-{[6-(1-methyl-1H-pyrazol-4-yl)-4-oxospiro[chroman-2,4'-piperidin]-1'-yl]carbonyl}quinolin-4-yl)benzoic acid;

(8) 4-(3-methyl-6-{[6-(1-methyl-1H-pyrazol-4-yl)-4-oxospiro[chroman-2,4'-piperidin]-1'-yl]carbonyl}-1H-indazol-1-yl)benzoic acid;

(9) 3-(3-methyl-6-{[6-(1-methyl-1H-pyrazol-4-yl)-4-oxospiro[chroman-2,4'-piperidin]-1'-yl]carbonyl}-1H-indazol-1-yl)benzoic acid;

(10) 4-(1-cyclopropyl-3-methyl-6-{[6-(1-methyl-1H-pyrazol-4-yl)-4-oxospiro[chroman-2,4'-piperidin]-1'-yl]carbonyl}-1H-indol-4-yl)benzoic acid;

(11) 1-(1-cyclopropyl-6-{[6-(1-methyl-1H-pyrazol-4-yl)-4-oxospiro[chroman-2,4'-piperidin]-1'-yl]carbonyl}-1H-indol-4-yl)piperidine-4-carboxylic acid;

(12) 3-(3-methyl-5-{[6-(1-methyl-1H-pyrazol-4-yl)-4-oxospiro[chroman-2,4'-piperidin]-1'-yl]carbonyl}-1H-indazol-1-yl)benzoic acid;

(13) 4-(3-methyl-5-{[6-(1-methyl-1H-pyrazol-4-yl)-4-oxospiro[chroman-2,4'-piperidin]-1'-yl]carbonyl}-1H-indazol-1-yl)benzoic acid;

(14) [(1-cyclopropyl-6-{[6-(1-methyl-1H-pyrazol-4-yl)-4-oxospiro[chroman-2,4'-piperidin]-1'-yl]carbonyl}-1H-indol-4-yl)oxy]acetic acid;

(15) 2-(1-cyclopropyl-6-{[6-(1-methyl-1H-pyrazol-4-yl)-4-oxospiro[chroman-2,4'-piperidin]-1'-yl]carbonyl}-1H-indol-4-yl)benzoic acid;

(16) 3-(1-cyclopropyl-6-{[6-(1-methyl-1H-pyrazol-4-yl)-4-oxospiro[chrornan-2,4'-piperidin]-1'-yl]carbonyl}-1H-indol-4-yl)benzoic acid;

(17) 4-(1-cyclopropyl-6-{[6-(1-methyl-1H-pyrazol-4-yl)-4-oxospiro[chroman-2,4'-piperidin]-1'-yl]carbonyl}-1H-indol-4-yl)benzoic acid;

(18) 2',6'-diethoxy-4'-{[6-(1-methyl-1H-pyrazol-4-yl)-4-oxospiro[chroman-2,4'-piperidin]-1'-yl]carbonyl}biphenyl-4-carboxylic acid;

(19) 4'-({6-(5-carbamoylpyridin-2-yl)-4-oxospiro[chroman-2,4'-piperidin]-1'-yl}carbonyl)-2',6'-diethoxybiphenyl-3-carboxylic acid;

(20) 2',6'-diethoxy-4'-{[6-(1-methyl-1H-pyrazol-4-yl)-4-oxospiro[chroman-2,4'-piperidin]-1'-yl]carbonyl}biphenyl-3-carboxylic acid;

(21) 5-(2,6-diethoxy-4-{[6-(1-methyl-1H-pyrazol-4-yl)-4-oxospiro[chroman-2,4'-piperidin]-1'-yl]carbonyl}phenyl)nicotinic acid;

(22) 2',6'-diethoxy-3-fluoro-4'-{[6-(1-methyl-1H-pyrazol-4-yl)-4-oxospiro[chroman-2,4'-piperidin]-1'-yl]carbonyl}biphenyl-4-carboxylic acid;

(23) 5-[4-({6-(3-carbamoylphenyl)-4-oxospiro[chroman-2,4'-piperidin]-1'-yl}carbonyl)-2,6-diethoxyphenyl]nicotinic acid; and

(24) 2',6'-diethoxy-4-fluoro-4'-{[6-(1-methyl-1H-pyrazol-4-yl)-4-oxospiro[chroman-2,4'-piperidin]-1'-yl]carbonyl}biphenyl-3-carboxylic acid;

or a pharmaceutically acceptable salt or ester thereof.

Methods for producing the compounds of the invention are described below.

The compounds (I) of the invention may be produced according to the production method such as Scheme 1, 2 or 3 mentioned below, or according to the methods shown in Examples and Reference Examples given hereinunder. However, the production of the compounds (I) of the invention should not be restricted by these reaction examples.

Production Method

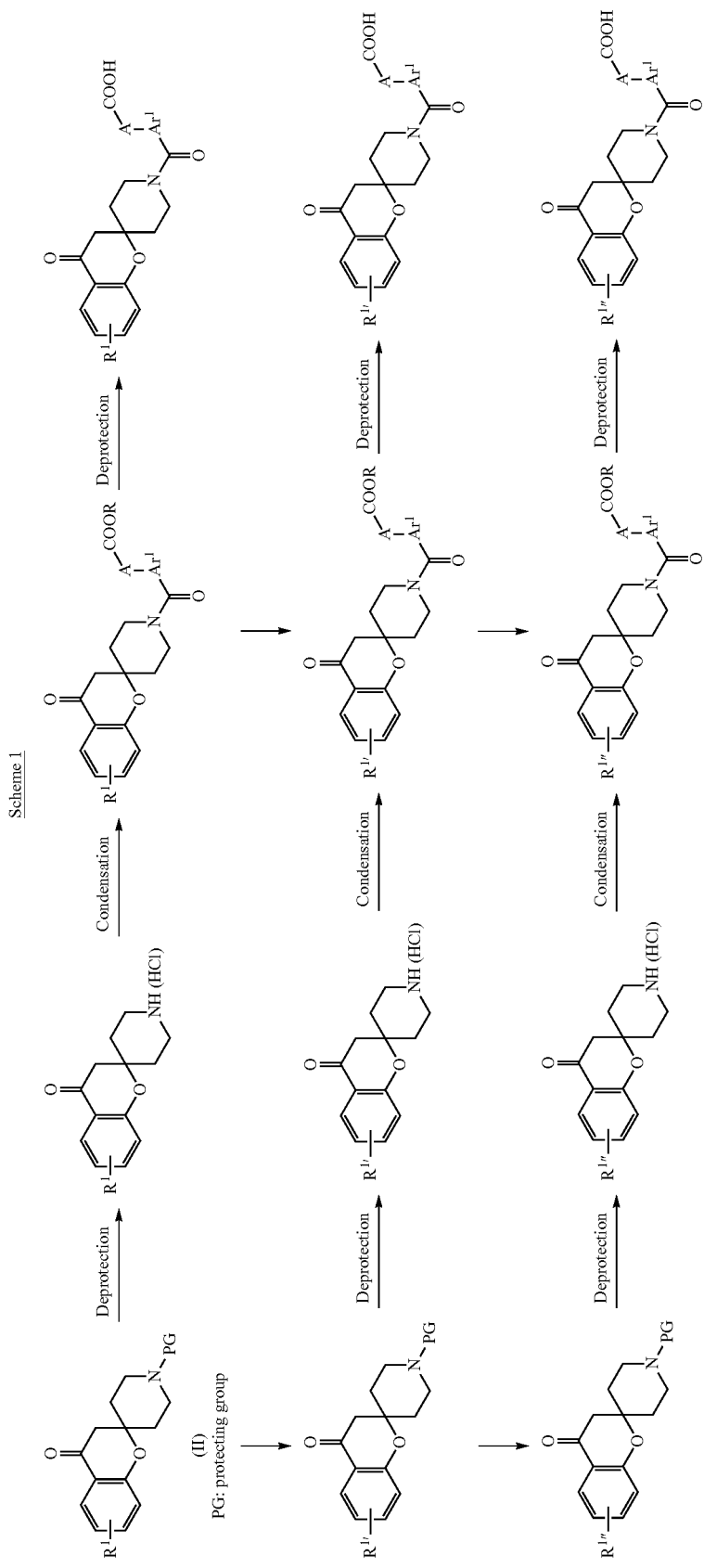

Scheme 2
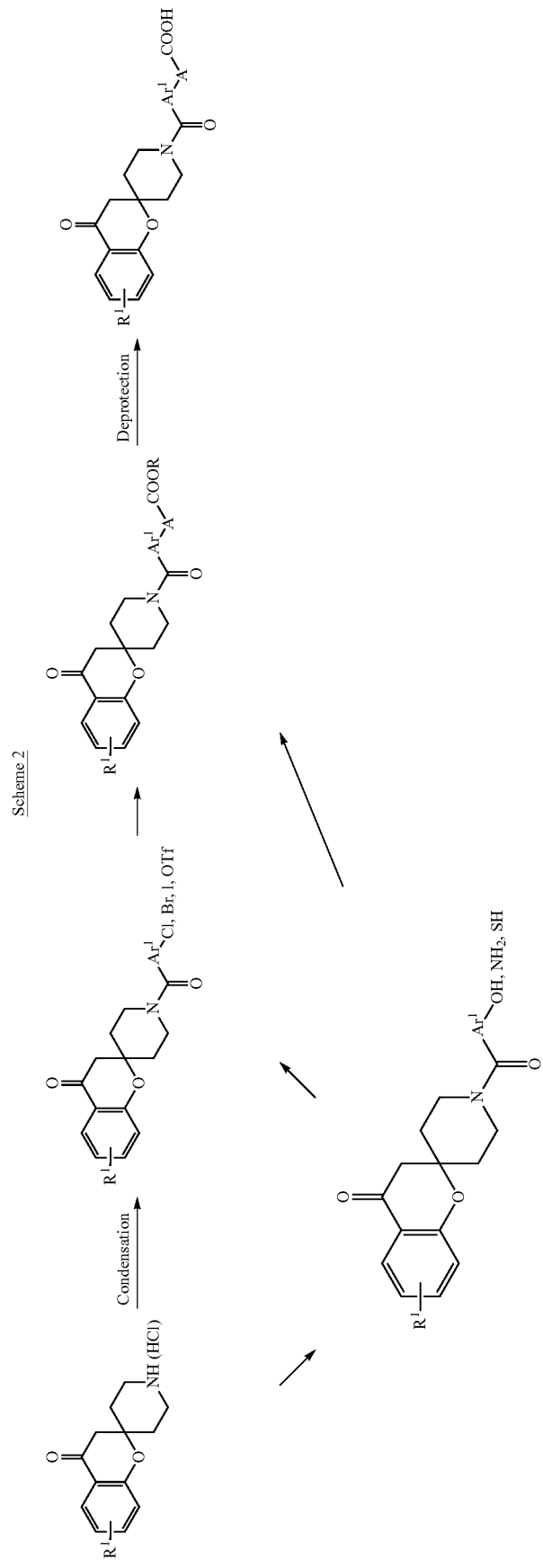

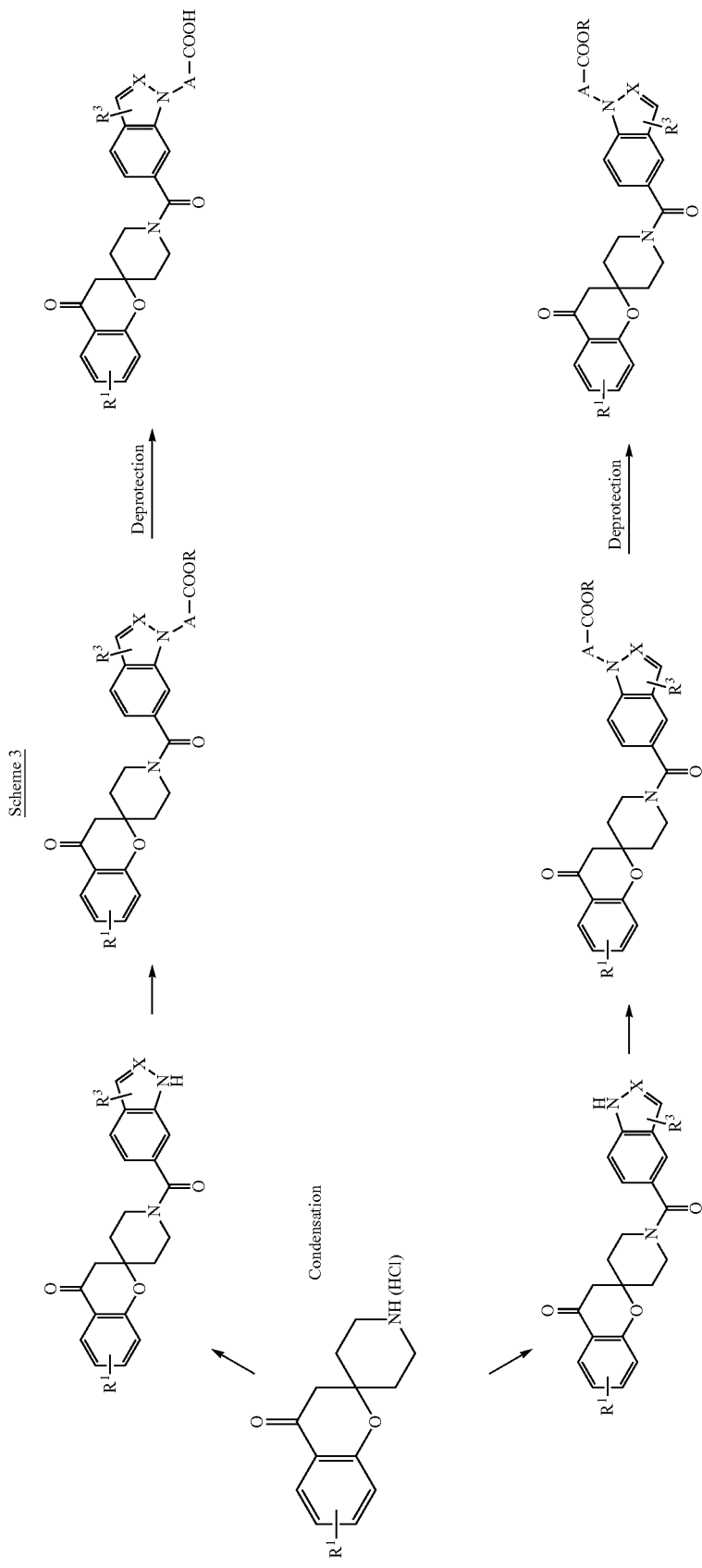

wherein OTf is a trifluoromethanesulfonyloxy group; R is a protective group for carboxyl group; X is a methine group or a nitrogen atom; and A, $Ar^1$, $R^1$ and $R^3$ have the same meanings as above.

A compound protected with a suitable group (II in the following drawing) is deprotected, and then condensed with an aromatic carboxylic acid or its reactive derivative of a formula (III):

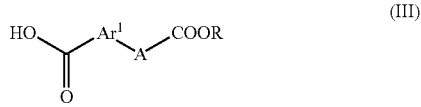

(III)

wherein A, $Ar^1$, and R have the same meanings as above, according to a chemical process itself well known in the field of organic chemistry.

The protective group (PG) may be, for example, a tert-butoxycarbonyl, benzyloxycarbonyl or benzoyl group, and may also be any other known protective group. For selecting suitable protective groups and their deprotection, for example, referred to is *Protective Groups in Organic Synthesis* (Theodora W. Greene & Peter G. M. Wuts, John Wiley & Sons, 1999).

In the above series of reaction, the functional groups such as hydroxyl group, amino group, imino group and carboxyl group not participating in the reaction may be suitably protected, if desired, and they may be deprotected after the reaction.

Not specifically defined, "protective group for hydroxyl group" may be any one having its function and includes, for example, a C1-C6 alkyl group such as a methyl group, an ethyl group, a propyl group, an isopropyl group, a tert-butyl group; a C1-C6 alkylsilyl group such as a trimethylsilyl group, a tert-butyldimethylsilyl group; a C1-C6 alkoxymethyl group such as a methoxymethyl group, a 2-methoxyethoxymethyl group; a tetrahydropyranyl group; a trimethylsilylethoxymethyl group, an aralkyl group such as a benzyl group, a p-methoxybenzyl group, a 2,3-dimethoxybenzyl group, an o-nitrobenzyl group, a p-nitrobenzyl group, a trityl group; an acyl group such as a formyl group, an acetyl group. Especially preferred are a methyl group, a methoxymethyl group, a tetrahydropyranyl group, a trityl group, a trimethylsilylethoxymethyl group, a tert-butyldimethylsilyl group, and an acetyl group.

Also not specifically defined, "protective group for amino group and imino group" may be any one having its function and includes, for example, an aralkyl group such as a benzyl group, a p-methoxybenzyl group, a 3,4-dimethoxybenzyl group, an o-nitrobenzyl group, a p-nitrobenzyl group, a benzhydryl group, a trityl group; a C2-C7 alkanoyl group such as a formyl group, an acetyl group, a propionyl group, a butyryl group, a pivaloyl group; a benzoyl group; an arylalkanoyl group such as a phenylacetyl group, a phenoxyacetyl group; a C2-C7 alkoxycarbonyl group such as a methoxycarbonyl group, an ethoxycarbonyl group, a propyloxycarbonyl group, a tert-butoxycarbonyl group; an aralkyloxycarbonyl group such as a benzyloxycarbonyl group, a p-nitrobenzyloxycarbonyl group, a phenethyloxycarbonyl group; a C1-C6 alkylsilyl group such as a trimethylsilyl group, a tert-butyldimethylsilyl group; a tetrahydropyranyl group; a trimethylsilylethoxymethyl group; a C1-C6 alkylsulfonyl group such as a methylsulfonyl group, an ethylsulfonyl group; an arylsulfonyl group such as a benzenesulfonyl group, a toluenesulfonyl group. Especially preferred are an acetyl group, a benzoyl group, a tert-butoxycarbonyl group, a benzyloxycarbonyl group, a trimethylsilylethoxymethyl group, and a methylsulfonyl group.

Also not specifically defined, "protective group for carboxyl group" may be any one having its function and includes, for example, a C1-C6 alkyl group such as a methyl group, an ethyl group, a propyl group, an isopropyl group, a tert-butyl group; a halo-C1-C6 alkyl group such as a 2,2,2-trichloroethyl group; a C2-C6 alkenyl group such as a 2-propenyl group; an aralkyl group such as a benzyl group, a p-methoxybenzyl group, a p-nitrobenzyl group, a benzhydryl group, a trityl group. Especially preferred are a methyl group, an ethyl group, a tert-butyl group, a 2-propenyl group, a benzyl group, a p-methoxybenzyl group, and a benzhydryl group.

For the introduction and the removal of the protective groups, referred to is the above reference.

The substituent $R^1$ may be converted into a group of any other type ($R^{1'}$, $R^{1''}$) in any suitable stage according to a chemical process per-se well known in the field of organic chemistry.

For example, when $R^1$ is a bromide group, then it may be converted into a cyano group and may be further into a tetrazolyl group. The conversion reaction may be attained according to a chemical process itself well known in the field of organic chemistry.

In the above drawing, the condensation of the amino compound derived from the compound of formula (II), with an aromatic carboxylic acid may be attained in the same manner. In general, from 0.5 mol to an excessive molar amount, preferably from 1 mol to 1.5 mols of an aromatic carboxylic acid is used relative to one mol of the amino compound.

The reaction may be attained generally in an inert solvent. The insert solvent is preferably methylene chloride, chloroform, tetrahydrofuran, dimethylformamide, pyridine or their mixtures.

Preferably, the reaction is effected in the presence of a condensing agent. The condensing agent includes, for example, N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris(dimethylamino)phosphonium hexafluorophosphate, benzotriazol-1-yloxy-tris-pyrrolidinophosphonium hexafluorophosphate, bromotris-(dimethylamino)phosphonium hexafluorophosphate, diphenylphosphoryl azide, 1,1'-carbonyldiimidazole.

The condensing agent may be used in an amount of from 1 mol to an excessive molar amount, preferably from 1 mol to 1.5 mols relative to 1 mol of the aromatic carboxylic acid.

The reaction temperature may be generally from −50° C. to 120° C., preferably from −20° C. to 80° C.

The reaction time may be generally from 30 minutes to 7 days, preferably from 1 hour to 24 hours.

In place of the aromatic carboxylic acid, a reactive derivative of the carboxylic acid may be reacted with the amino compound to produce the intended product.

The reactive derivative of the aromatic carboxylic acid usable herein includes, for example, acid halides, mixed acid anhydrides, active esters, and active amides.

The acid halide may be prepared by reacting the aromatic carboxylic acid with a halogenating agent in an ordinary manner. The halogenating agent includes, for example, thionyl chloride, phosphorus trichloride, phosphorus pentachloride, phosphorus oxychloride, phosphorus tribromide, oxalyl chloride, and phosgene.

The mixed acid anhydride may be prepared by reacting the aromatic carboxylic acid with an alkyl chlorocarbonate such as ethyl chlorocarbonate or with an aliphatic carboxylic acid chloride such as pivaloyl chloride, in an ordinary manner.

The active ester may be prepared by reacting the aromatic carboxylic acid with an N-hydroxy compound such as N-hydroxysuccinimide, N-hydroxyphthalimide or 1-hydroxybenzotriazole, or with a phenol compound such as 4-nitrophenol, 2,4-dinitrophenol, 2,4,5-trichlorophenol or pentachlorophenol, in the presence of a condensing agent such as N,N'-dicyclohexylcarbodiimide or 1-(3-dimethylaminopropyl)-3-ethylcarbodiimide, in an ordinary manner.

The active amide may be prepared by reacting the aromatic carboxylic acid with, for example, 1,1'-carbonyldiimidazole or 1,1'-carbonylbis(2-methylimidazole) in an ordinary manner.

The reaction between the amino compound and the reactive derivative of the carboxylic acid may be attained, generally using from 0.5 mols to an excessive molar amount, preferably from 1 mol to 1.5 mols of the reactive derivative of the carboxylic acid, per 1 mol of the amino compound.

The reaction may be effected generally in an inert solvent. The inert solvent is, for example, preferably methylene chloride, chloroform, tetrahydrofuran, dimethylformamide, pyridine and their mixtures.

The reaction may go on in the absence of a base, but for more smoothly promoting it, the reaction is preferably effected in the presence of a base.

The base includes an organic base such as triethylamine, diisopropylethylamine, pyridine, 4-dimethylaminopyridine; and an inorganic base such as sodium hydroxide, potassium hydroxide, sodium carbonate, potassium carbonate, sodium hydrogencarbonate.

In general, the base is used preferably in an amount of from 1 mol to an excessive molar amount relative to 1 mol of the amino compound. When the base is liquid, then the base may serve also as a solvent.

The reaction temperature may be generally from −50° C. to 120° C., preferably from −20° C. to 80° C.

The reaction time may be generally from 5 minutes to 7 days, preferably from 30 minutes to 24 hours.

After the reaction, the system may be processed in an ordinary manner to give a crude product of the intended compound. The thus-obtained compound may be purified in an ordinary manner, or not purified, it may be subjected to the next reaction, if desired.

After the reaction, when the product has a protective group, then the protective group may be removed. When the product does not have a protective group, it may be processed in any ordinary manner, and the intended final product may be thus produced.

The compounds of formulae (II) and (III) may be commercial products, or may be prepared according to a known method or according to a method similar to a known method, or with reference to the methods described in Examples and Reference Examples, suitably as combined, if desired.

Alternatively, the compounds (I) of the invention may be produced by reacting a compound or its reactive derivative of formula (III'):

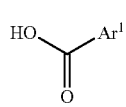

(III')

wherein Ar¹ has the same meanings as above but it may have a leaving group such as a halogen atom or a trifluoromethylsulfonyl group, or other group that can be converted to said leaving group according to a chemical process itself well known in the field of organic chemistry, instead of the compound of formula (III) or its reactive derivative, and then introducing the group of formula:

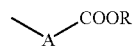

on the Ar¹ according to a chemical process itself well known in the field of organic chemistry.

The compounds of formula (I) may be administered orally or parenterally, and after formulation into preparations suitable for the intended administration route, they can be used as therapeutic agents, for example, for vascular diseases such as hypertension, cardiac angina, heart failure, cardiac infarction, stroke, claudication, diabetic nephropathy, diabetic retinopathy, eyesight failure, electrolyte abnormality and arteriosclerosis; nervous system diseases such as bulimia and diabetic neuropathy; metabolic diseases such as metabolic syndrome, obesity, diabetes, insulin resistance, hyperlipemia, hypercholesterolemia, hypertriglyceridemia, dyslipidemia, non-alcoholic fatty liver disease, hormone secretion failure, gout and hepatic steatosis; genital diseases such as emmeniopathy, sexual dysfunction; digestive system diseases such as liver dysfunction, pancreatitis, cholecystitis and gastroesophageal reflux; respiratory diseases such as Pickwickian syndrome and sleep apnea syndrome; infectious diseases caused by bacteria, fungi or parasites; malignant neoplasm; and inflammatory diseases such as arthritis and skin ulcer.

The following "diabetes related disorders" are diseases, disorders and conditions that are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, ACC 1/2 inhibitors may also be useful to treat hypertension associated with this condition.

One aspect of the present invention provides a method for the treatment or prevention of disorders, diseases or conditions responsive to the modulation of ACC-1 or ACC-2 in a subject in need thereof which comprises administering to the subject a therapeutically or prophylactically effective amount of a compound of formula (I), or a pharmaceutically acceptable salt or ester thereof.

Another aspect of the present invention provides a method for the treatment or prevention of metabolic syndrome, fatty liver, hyperlipemia, dyslipidemia, non-alcoholic fatty liver disease, obesity, diabetes, bulimia, malignant neoplasm or an infectious disease in a subject in need thereof which comprises administering to said subject a therapeutically or prophylactically effective amount of a compound of formula (I), or a pharmaceutically acceptable salt or ester thereof.

Another aspect of the present invention provides a method for the treatment of metabolic syndrome, fatty liver, hyperlipemia, obesity, diabetes, bulimia, malignant neoplasm or infectious diseases, which comprises administering to a subject in need thereof a therapeutically effective amount of the compound or its salt or ester of Claim 1.

Another aspect of the present invention provides a method for the treatment or prevention of diabetes in a subject in need thereof which comprises administering to said subject a therapeutically or prophylactically effective amount of a compound of formula (I), or a pharmaceutically acceptable salt or ester thereof.

Another aspect of the present invention provides a method for the treatment or prevention of obesity in a subject in need thereof which comprises administering to said subject a therapeutically or prophylactically effective amount of a compound of formula (I), or a pharmaceutically acceptable salt or ester thereof.

Another aspect of the present invention provides a method for the treatment or prevention of an obesity-related disorder selected from the group consisting of overeating, binge eating, hypertension, elevated plasma insulin concentrations, insulin resistance, hyperlipidemia, endometrial cancer, breast cancer, prostate cancer, colon cancer, kidney cancer, osteoarthritis, obstructive sleep apnea, heart disease, abnormal heart rhythms and arrythmias, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastro-esophageal reflux, Pickwickian syndrome, inflammation, systemic inflammation of the vasculature, arteriosclerosis, hypercholesterolemia, hyperuricaemia, lower back pain, gallbladder disease, gout, constipation, irritable bowel syndrome, inflammatory bowel syndrome, cardiac hypertrophy, left ventricular hypertrophy, in a subject in need thereof which comprises administering to the subject a therapeutically or prophylactically effective amount of a compound of formula (I), or a pharmaceutically acceptable salt or ester thereof.

Another aspect of the present invention provides a method for the treatment or prevention of hyperlipemia or dyslipidemia in a subject in need thereof which comprises administering to the subject a therapeutically or prophylactically effective amount of a compound of formula (I), or a pharmaceutically acceptable salt or ester thereof.

Another aspect of the present invention provides a method for caloric intake in a subject in need thereof which comprises administering to the subject a therapeutically or prophylactically effective amount of a compound of formula (I), or a pharmaceutically acceptable salt or ester thereof. Another aspect of the present invention provides a method for reducing food intake in a subject in need thereof which comprises administering to the subject a therapeutically or prophylactically effective amount of a compound of formula (I), or a pharmaceutically acceptable salt or ester thereof. Another aspect of the present invention provides a method for increasing satiety in a subject in need thereof which comprises administering to the subject a therapeutically or prophylactically effective amount of a compound of formula (I), or a pharmaceutically acceptable salt or ester thereof. Another aspect of the present invention provides a method for reducing appetite in a subject in need thereof which comprises administering to the subject a therapeutically or prophylactically effective amount of a compound of formula (I), or a pharmaceutically acceptable salt or ester thereof.

The present invention also relates to methods for treating or preventing obesity by administering a compound of formula (I), or a pharmaceutically acceptable salt or ester thereof, in combination with a therapeutically or prophylactically effective amount of another agent known to be useful to treat or prevent the condition.

The present invention also relates to methods for treating or preventing diabetes by administering a compound of formula (I), or a pharmaceutically acceptable salt or ester thereof, in combination with a therapeutically or prophylactically effective amount of another agent known to be useful to treat or prevent the condition.

The present invention also relates to methods for treating or preventing hyperlipemia or dyslipidemia by administering a compound of formula (I), or a pharmaceutically acceptable salt or ester thereof, in combination with a therapeutically or prophylactically effective amount of another agent known to be useful to treat or prevent the condition.

Another aspect of the present invention provides a pharmaceutical composition comprising a compound of formula (I), or a pharmaceutically acceptable salt or ester thereof, and a pharmaceutically acceptable carrier.

Yet another aspect of the present invention relates to a compound of formula (I), or a pharmaceutically acceptable salt or ester thereof, for use in medicine.

Yet another aspect of the present invention relates to the use of a compound of formula (I), or a pharmaceutically acceptable salt or ester thereof, for the manufacture of a medicament useful for the treatment or prevention, or suppression of a disease mediated by ACC-1 or ACC-2 in a subject in need thereof.

Yet another aspect of the present invention relates to the use of a compound of formula (I), or a pharmaceutically acceptable salt or ester thereof, for the manufacture of a medicament useful for the treatment or prevention of metabolic syndrome, hyperlipemia, dyslipidemia, non-alcoholic fatty liver disease, obesity, diabetes, bulimia, malignant neoplasm or an infectious disease in a subject in need thereof.

Yet another aspect of the present invention relates to the use of a compound of formula (I), or a pharmaceutically acceptable salt or ester thereof, for the manufacture of a medicament useful for the treatment or prevention of obesity in a subject in need thereof.

Yet another aspect of the present invention relates to the use of a compound of formula (I), or a pharmaceutically acceptable salt or ester thereof, for the manufacture of a medicament useful for the treatment or prevention of diabetes in a subject in need thereof.

Yet another aspect of the present invention relates to the use of a compound of formula (I), or a pharmaceutically acceptable salt or ester thereof, for the manufacture of a medicament useful for the treatment or prevention of hyperlipemia or dyslipidemia in a subject in need thereof.

Yet another aspect of the present invention relates to the use of a therapeutically effective amount of a compound of formula (I), or a pharmaceutically acceptable salt or ester thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagons like peptide 1 (GLP-1) agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, PYY$_{3-36}$, and a NK-1 antagonist, or a pharmaceutically acceptable salt thereof, for the manufacture of a medicament useful for the treatment, control, or prevention of obesity, diabetes, a diabetes related disorder, or an obesity-related disorder in a subject in need of such treatment.

Yet another aspect of the present invention relates to the use of a therapeutically effective amount of a compound of formula (I), or a pharmaceutically acceptable salt or ester thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagon-like peptide 1 agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid CB$_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, PYY$_{3-36}$, and a NK-1 antagonist, or a pharmaceutically acceptable salt thereof, for the manufacture of a medicament for treatment or prevention of obesity, diabetes, a diabetes related disorder, or an obesity-related disorder which comprises an effective amount of a compound of formula (I), or a pharmaceutically acceptable salt or ester thereof, and an effective amount of the agent, together or separately.

Yet another aspect of the present invention relates to a product containing a therapeutically effective amount of a compound of formula (1), or a pharmaceutically acceptable salt or ester thereof; and and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid CB$_1$ receptor antagonist or inverse agonist, a melanocortin 4 receptor agonist, a melanin-concentrating hormone receptor antagonist, a bombesin receptor subtype 3 agonist, a ghrelin receptor antagonist, PYY, PYY$_{3-36}$, and a NK-1 antagonist, or a pharmaceutically acceptable salt thereof, as a combined preparation for simultaneous, separate or sequential use in obesity, diabetes, a diabetes related disorder, or an obesity-related disorder.

Yet another aspect of the present invention relates to the use of a therapeutically effective amount of a compound of formula (I), or a pharmaceutically acceptable salt or ester thereof, and a therapeutically effective amount of at least one agent selected from the group consisting of: simvastatin, mevastatin, ezetimibe, atorvastatin, sitagliptin, metformin, sibutramine, orlistat, Qnexa, topiramate, phentermine, losartan, losartan with hydrochlorothiazide, or a CB1 antagonist/inverse agonist selected from: rimonabant, N-[3-(4-chlorophenyl)-2(S)-phenyl-1(S)-methylpropyl]-2-(4-trifluoromethyl-2-pyrimidyloxy)-2-methylpropanamide, N-[(1S,2S)-3-(4-chlorophenyl)-2-(3-cyanophenyl)-1-methylpropyl]-2-methyl-2-{[5-(trifluoromethyl)pyridin-2-yl]oxy}propanamide, N-[3-(4-chlorophenyl)-2-(5-chloro-3-pyridyl)-1-methylpropyl]-2-(5-trifluoromethyl-2-pyridyloxy)-2-methylpropanamide, 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]-azetidin-3-yl}-1-(3,5-difluorophenyl)-2-methylpropan-2-ol, 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)-benzonitrile, 3-((4-chlorophenyl){3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl) {3-[1-(3,5-difluorophenyl)-2-fluoro-2-methylpropyl]azetidin-1-yl}methyl)thiophene-3-carbonitrile, or a pharmaceutically acceptable salt or ester or prodrug thereof, for the manufacture of a medicament useful for the treatment, control, or prevention of obesity, diabetes, a diabetes related disorder, or an obesity-related disorder in a subject in need of such treatment.

In clinical use of the compounds of the invention, pharmaceutically-acceptable additives may be added thereto to formulate various preparations in accordance with the intended administration route thereof, and the preparations may be administered. Various additives generally used in the field of pharmaceutical compositions may be used herein, including, for example, gelatin, lactose, sucrose, titanium oxide, starch, crystalline cellulose, methyl cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into various forms of preparations, for example, solid preparations such as tablets, capsules, granules, powders and suppositories; and liquid preparations such as syrups, elixirs and injections. These preparations can be produced in any method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The compounds of the invention are effective for animals including humans and other mammals and plants that require the treatment with the compound. For the mammals, humans are preferred and they may be either men or women. The mammals except humans are, for example, companion animals such as dogs and cats. The compounds of the invention are effective also for obesity and obesity-related disorders of dogs and cats. Any ordinary physicians, veterinarians and clinicians may readily determine the necessity, if any, of the treatment with the compound of the invention.

When the compound of the invention is, for example, put into clinical use, then its dose and its administration frequency may vary depending on the sex, the age, the body weight and the condition of the patient and on the type and the range of the necessary treatment with the compound. In oral administration, in general, the dose of the compound may be from 0.01 to 100 mg/kg of adult/day, preferably from 0.03 to 1 mg/kg of adult/day, and the administration frequency is preferably from one to a few times; and in parenteral administration, the dose may be from 0.001 to 10 mg/kg of adult/ day, preferably from 0.001 to 0.1 mg/kg of adult/day, more preferably from 0.01 to 0.1 mg/kg of adult/day, and the administration frequency is preferably from one to a few times. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing obesity and/or diabetes mellitus and/or hyperlipemia and/or dyslipidemia and/or non-alcoholic fatty liver disease, or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

Ordinary physicians, veterinarians and clinicians may readily determine the effective dose of the pharmaceutical compound necessary to treat, prevent, inhibit, retard or stop the intended disease, and may readily treat the diseased patient with the compound.

The preparation may contain the compound of the invention in an amount of from 1.0 to 100% by weight, preferably from 1.0 to 60% by weight of the preparation. The preparation may contain any other therapeutically-effective compound.

In their use, the compounds of the invention may be combined with any other therapeutic agents that are useful for the treatment of disorders, for example, vascular diseases such as hypertension, cardiac angina, heart failure, cardiac infarction, stroke, claudication, diabetic nephropathy, diabetic retinopathy, eyesight failure, electrolyte abnormality and arteriosclerosis; nervous system diseases such as bulimia and diabetic neuropathy; metabolic diseases such as metabolic syndrome, obesity, diabetes, pre-diabetes, insulin resistance, hyperlipemia, hypercholesterolemia, hypertriglyceridemia, dyslipidemia, non-alcoholic fatty liver disease, hormone secretion failure, gout and hepatic steatosis; genital diseases such as emmeniopathy and sexual dysfunction; digestive tract diseases such as liver dysfunction, pancreatitis, cholecystitis and gastroesophageal reflux; respiratory system diseases such as Pickwickian syndrome and sleep apnea syndrome; infectious diseases caused by bacteria, fungi or parasites; malignant neoplasm; and inflammatory diseases such as arthritis and skin ulcer. The individual ingredients to be combined may be administered at the same time or at different times during the treatment period, either as one preparation or as different preparations. Accordingly, the invention should be so interpreted that it encompasses any and every administration mode at the same time or at different times, and the administration in the invention should be interpreted so. The range of the combination of the compound of the invention and the other therapeutic agent useful for the above-mentioned disorders encompasses, in principle, all combinations of the compound of the invention and any and every pharmaceutical agent useful for the above-mentioned disorders.

The combination includes not only the composition of compounds of the invention and one other active substance but also the composition of compounds of the invention and two or more other active substances. There are a lot of examples of the combinations of a compound of the invention and one, two or more active substances selected from the therapeutic agents for the above-mentioned disorders. For example, for the treatment, management and prevention of metabolic syndrome, a combination of a compound of the invention and one, two or more active substances selected from hypolipidemic agents, lipid lowering agents, and anti-diabetic agents is useful. In particular, a composition that also contains an anti-obesity agent and an anti-hypertension agent, in addition to an anti-diabetic agent and/or a hypolipidemic agent or lipid lowering agent, may exhibit a synergistic effect for treatment, management and prevention of metabolic syndrome.

The pharmaceutical agents that may be combined with the compound of the invention are, for example, ACAT inhibitor, α-blocker, aldose reductase inhibitor, α-amylase inhibitor, angiotensin-converting enzyme inhibitor, angiotensin receptor antagonist, anion exchange resin, anorectic, antioxidant, antiplatelet, β-blocker, biguanide agent, calcium antagonist, CB1 receptor inverse agonist/antagonist, CETP inhibitor, cholesterol absorption inhibitor, DGAT inhibitor, DP-IV inhibitor, diuretic, eicosapentaenoic acid, endothelin antagonist, FLAP inhibitor, FXR modulator, Ghrelin antagonist, GLP-1 agonist, GLP-1 secretagogue, glucagon antagonist, glucokinase activator, glucocorticoid receptor ligand, α-glucosidase inhibitor, GPAT inhibitor, histamine-H3 receptor ligand, HMG-CoA reductase inhibitor, HSD inhibitor, insulin and insulin mimetics, kinase inhibitors such as VEGF inhibitor and PDGF inhibitor, leptin, lipase inhibitor, 5-LO inhibitor, LXR ligand, melanocortin agonist, MCH antagonist, MTTP inhibitor, orexin antagonist, opioid antagonist, neuropeptide Y antagonist, nicotinic acid agonist, PPAR ligand, PTP-1B inhibitor, SCD-1 inhibitor, serotonin transporter inhibitor, SGLT inhibitor, SUR ligand, thyroid hormone agonist, UCP activator, VPAC receptor agonist.

More concretely, examples of the other active ingredients that can be combined with a compound of the invention as different or the same pharmaceutical compositions are shown below, which, however, do not restrict the invention.

(a) Anti-diabetic medicines or agents, for example, (1) glitazones (e.g., ciglitazone, darglitazone, englitazone, isaglitazone (MCC-555), pioglitazone, rosiglitazone, troglitazone, tularik, BRL49653, CLX-0921, 5-BTZD), and PPAR-γ agonists such as GW-0207, LG-100641 and LY-300512; (2) biguanides such as buformin, metformin and phenformin; (3) protein tyrosine phosphatase-1B (PTP-1B) inhibitors; (4) sulfonylureas such as acetohexamide, chlorpropamide, diabinese, glibenclamide, glipizide, glyburide, glimepiride, gliclazide, glipentide, gliquidone, glisolamide, tolazamide and tolbutamide; (5) meglitinides such as repaglinide, nateglinide, and the like; (6) α-glucosidase inhibitors such as acarbose, adiposine, camiglibose, emiglitate, miglitol, voglibose, pradimicin-Q, salbostatin, CKD-711, MDL-25,637, MDL-73,945, and MOR14; (7) α-amylase inhibitors such as tendamistat, trestatin, and AI-3688; (8) insulin secretagogues such as linogliride, A-4166 and the like; (9) fatty acid oxidation inhibitors such as clomoxir, and etomoxir; (10) α-2 antagonists such as midaglizole, isaglidole, deriglidole, idazoxan, earoxan, and fluparoxan; (11) insulin and insulin mimetics such as biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-NH$_2$; (12) non-thiazolidinediones such as JT-501, farglitazar (GW-2570/GI-262579), and muraglitazar; PPAR α/δ agonists, such as muraglitazar, and the compounds disclosed in U.S. Pat. No. 6,414,002; (13) PPAR-α/γ dual agonists such as MK-0767/KRP-297, CLX-0940, GW-1536, GW-1929, GW-2433, L-796449, LR-90, and SB219994; (14) other insulin sensitizers; (15) VPAC2 receptor agonists; (16) glucokinase activators; and (17) DPP-4 inhibitors, such as sitagliptin (Januvia™), isoleucine thiazolidide (P32/98); NVP-DPP-728; vildagliptin (LAF 237); P93/01; denagliptin (GSK 823093), SYR322, RO 0730699, TA-6666, and saxagliptin (BMS 477118).

(b) lipid lowering agents, for example, (1) bile acid sequestrants such as cholestyramine, colesevelam, colestipol, dialkylaminoalkyl derivatives of a cross-linked dextran, Colestid®, LoCholest®, and Questran®, and the like; (2) HMG-CoA reductase inhibitors such as atorvastatin, itavastatin, fluvastatin, lovastatin, pitavastatin, pravastatin, rivastatin, rosuvastatin, and simvastatin, ZD-4522, and the like; (3) HMG-CoA synthase inhibitors; (4) cholesterol absorption inhibitors such as stanol esters, β-sitosterol, sterol glycosides such as tiqueside, and azetidinones like ezetimibe; (5) acyl coenzyme A-cholesterol acyl-transferase (ACAT) inhibitors such as avasimibe, eflucimibe, KY505, and SMP797, and the like; (6) CETP inhibitors such as JTT705, torcetrapib, CP532632, BAY63-2149, SC591, and SC795, and the like; (7) squalene synthase inhibitors; (8) antioxidants such as probucol; (9) PPAR-α agoists such as beclofibrate, benzafibrate, ciprofibrate, clofibrate, etofibrate, fenofibrate, gemcabene, gemfibrozil, and other fibric acid derivatives, e.g., GW7647, BM170744, LY518674, Atromid®, Lopid®, and Tricor®, and compounds described in WO 97/36579, and the like; (10) FXR receptor modulators such as GW4064, SR103912, and the like; (11) LXR receptor ligands such as GW3965, T9013137, and XTCO179628, and the like; (12) lipoprotein synthesis inhibitors such as niacin; (13) renin/angiotensin system inhibitors; (14) PPAR-δ partial agonists; (15) bile acid reabsorption inhibitors such as BARI1453, SC435, PHA384640, S8921, AZD7706, and the like; (16) PPAR-δ agonists such as GW501516, GW590735, and compounds described in WO97/28149, and the like; (17) triglyceride synthesis inhibitors, (18) microsomal triglyceride transport (MTTP) inhibitors such as inplitapide, LAB687, and CP346086; (19) transcription modulators, (20) squalene epoxidase inhibitors; (21) low-density lipoprotein (LDL) receptor inducers; (22) platelet aggregation inhibitors; (23) 5-LO or FLAP inhibitors; and (24) niacin receptor agonists; and (c) anti-hypertensive agents, for example, (1) diuretics such as thiazides including chlorthalidone, chlorothiazide, dichlorphenamide, hydroflumethiazide, indapamide and hydrochlorothiazide; loop diuretics such as bumetanide, ethacrynic acid, furosemide, and torsemide; potassium sparing agents such as amiloride, triamterene; aldosterone antagonists such as spironolactone, and epirenone, and the like; (2) β-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, and verapamil, and the like; (4) angiotensin converting enzyme (ACE) inhibitors such as benazepril, captopril, cilazapril, delapril, enalapril, fosinopril, imidapril, lisinopril, moexipril, quinapril, quinaprilat, ramipril, perindopril, perindropril, quanipril, spirapril, tenocapril, trandolapril, and zofenopril and the like; (5) neutral endopeptidase inhibitors such as omapatrilat, cadoxatril, ecadotril, fosidotril, sampatrilat, AVE7688, ER4030, and the like; (6) endothelin antagonists such as bosentan, tezosentan, A308165, and YM62899, and the like; (7) vasodilators such as hydralazine, clonidine, minoxidil, and nicotinyl alcohol; (8) angiotensin II receptor antagonists such as candesartan, eprosartan, irbesartan, losartan, losartan and hydrochlorothiazide, pratosartan, tasosartan, telmisartan, valsartan, EXP-3137, FI6828K, and RNH6270, and the like; (9) α/β-adrenergic blockers such as nipradilol, arotinolol, and amosulalol; (10) α1 blockers such as terazosin, urapidil, prazosin, bunazosin, trimazosin, doxazosin, naftopidil, indoramin, WHIP164, and XEN010; (11) α2 agonists such as lofexidine, tiamenidine, moxonidine, rilmenidine, and guanobenz; (12) aldosterone inhibitors; and (d) anti-obesity agents, for example, (1) 5HT (serotonin) transporter inhibitors such as paroxetine, fluoxetine, fenfluramine, fluvoxamine, sertraline, and imipramine; (2) NE (norepinephrine) transporter inhibitors such as GW320659, despiramine, talsupram, nomifensine, and the like; (3) CB-1 (cannabinoid-1 receptor) antagonists/inverse agonists such as rimonabant (Sanofi Synthelabo), SR-147778 (Sanofi Synthelabo), BAY65-2520 (Bayer), SLV319 (Solvey); and the compounds disclosed in U.S. Pat. Nos. 5,532,237, 4,973,587, 5,013,837, 5,081,122, 5,112,820, 5,292,736, 5,624,941, 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887, WO04/048317, WO05/000809, and EPO NO. EP-658546, EP656354, EP576357; (4) ghrelin antagonists such as those disclosed in WO01/87335, WO02/08250; (5) H3 (histamine H3) antagonists/inverse agonists such as thioperamide, 3-(1H-imidazol-4-yl)propyl N-(4-pentenyl) carbamate, clobenpropit, iodophenpropit, imoproxifan, GT2394 (Gliatech), A331440, and those disclosed in WO02/15905, O-[3-(1H-imidazol-4-yl)propanol]carbamates (Kiec-Kononowicz, K. et al., *Pharmazie,* 55:349-355 (2000)), piperidine-containing histamine H3-receptor antagonists (Lazewska, D. et al., *Pharmazie,* 56:927-932 (2001)), benzophenone derivatives and related compounds (Sasse, A. et al., *Arch. Pharm.* (Weinheim) 334:45-52 (2001)), substituted N-phenylcarbamates (Reidemeister, S. et al., Pharmazie, 55:83-86 (2000)), and proxifan derivatives (Sasse, A. et al., *J. Med. Chem.,* 43:3335-3343 (2000)); (6) melanin-concentrating hormone-1 receptor (MCH1R) antagonists such as T-226296 (Takeda), SNP-7941 (Synaptic), and those disclosed in WO01/82925, WO01/87834, WO02/051809, WO02/06245, WO02/076929, WO02/076947, WO02/04433, WO02/51809, WO02/083134, WO02/094799, WO03/004027, and Japanese Patent Application No. JP13226269, JP2004-139909; (7) MCH2R (melanin-concentrating hormone 2R) agonists/antagonists; (8) NPY1 (neuropeptide Y Y1) antagonists such as BIBP3226, 2-[1-(5-chloro-3-isopropyloxycarbonylaminophenyl)ethylamino]-6-[2-(5-ethyl-4-methyl-1,3-thiazol-2-yl)ethyl]-4-morpholinopyridine, BIBO3304, LY-357897, CP-671906, GI-264879A, and those disclosed in U.S. Pat. No. 6,001,836, WO96/14307, WO01/23387, WO99/51600, WO01/85690, WO01/85098, WO01/85173, and WO01/89528; (9) NPY5 (neuropeptide Y Y5) antagonists such as L-152,804, GW-569180A, GW-594884A, GW-587081X, GW-548118X, FR235,208, FR-226928, FR240662, FR252384, 1229U91, GI-264879A, CGP71683A, LY-377897, LY366377, PD-160170, SR-120562A, SR-120819A, JCF-104, H409/22, and the compounds disclosed in U.S. Pat. Nos. 6,057,335, 6,043,246, 6,140,354, 6,166,038, 6,180,653, 6,191,160, 6,258,837, 6,313,298, 6,337,332, 6,329,395, 6,340,683, 6,326,375, 6,329,395, 6,337,332, 6,335,345, 6,388,077, 6,462,053, 6,649,624, 6,723,847, EPO EP-01010691, EP-01044970, PCT WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO01/85730, WO01/07409, WO01/02379, WO01/23388, WO01/23389, WO01/44201, WO01/62737, WO01/62738, WO01/09120, WO02/20488, WO02/22592, WO02/48152, WO02/49648, WO02/094789, WO02/094825, WO03/014083, WO03/10191, WO03/092889, WO2004/002986, WO2004/031175, and Norman et al., *J. Med. Chem.*, 43:4288-4312 (2000); (10) leptins such as recombinant human leptin (PEG-OB, Hoffman La Roche), and recombinant methionyl human leptin (Amgen); (11) leptin derivatives such as those disclosed in U.S. Pat. Nos. 5,552,524, 5,552,523, 5,552,522, 5,521,283, PCT WO96/23513, WO96/23514, WO96/23515, WO96/23516, WO96/23517, WO96/23518, WO96/23519, and WO96/23520; (12) opioid antagonists such as nalmefene (Revex®), 3-methoxynaltrexone, naloxone, naltrexone, and the compounds disclosed in WO00/21509; (13) orexin antagonists such as SB-334867-A, and the compounds disclosed in WO01/96302, WO01/68609, WO02/51232, WO02/51838, and WO03/023561; (14) BRS3 (bombesin receptor subtype 3) agonists such as [D-Phe6,beta-Ala11,Phe13,Nle14]Bn(6-14) and [D-Phe6,Phe13]Bn(6-13)propylamide, and those compounds disclosed in Pept. Sci. 2002 August; 8(8): 461-75); (15) CCK-A (cholecystokinin-A) agonists such as AR-R15849, GI181771, JMV-180, A-71378, A-71623, SR146131, and the compounds disclosed in U.S. Pat. No. 5,739,106; (16) CNTF (ciliary neurotrophic factors) such as GI-181771 (Glaxo-SmithKline), SR146131 (Sanofi Synthelabo), butabindide, and PD170292 and PD149164 (Pfizer); (17) CNTF derivatives such as axokine (Regeneron), and the compounds disclosed in WO94/09134, WO98/22128, and WO99/43813; (18) GHS (growth hormone secretagogue receptor) agonists such as NN703, hexarelin, MK-0677, SM-130686, CP-424,391, L-692,429, L-163,255, and the compounds disclosed in U.S. Pat. Nos. 5,536,716, 6,358,951, USP Application Nos. 2002/049196, 2002/022637, WO01/56592, and WO02/32888; (19) 5HT2c (serotonin receptor 2c) agonists such as BVT933, DPCA37215, IK264, PNU22394, WAY161503, R-1065, YM348, and the compounds disclosed in U.S. Pat. No. 3,914,250, WO02/36596, WO02/48124, WO02/10169, WO01/66548, WO02/44152, WO02/51844, WO02/40456, and WO02/40457; (20) Mc3r (melanocortin-3 receptor) agonists; (21) Mc4r (melanocortin-4 receptor) agonists such as CHIR86036 (Chiron), ME-10142 and ME-10145 (Melacure), PT-141 and PT-14 (Palatin), and the compounds disclosed in U.S. Pat. Nos. 6,410,548, 6,294,534, 6,350,760, 6,458,790, 6,472,398, 6,376,509, and 6,818,658, USP Application No. US2002/0137664, US2003/0236262, US2004/009751, US2004/0092501, WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, WO03/009847, WO04/024720, WO04/078716, WO04/078717, WO04/087159, WO04/089307 and WO05/009950; (22) monoamine reuptake inhibitors such as sibutramine (Meridia®/Reductil®) and its salts, and the compounds disclosed in U.S. Pat. Nos. 4,746,680, 4,806,570, 5,436,272, USP Publication No. 2002/0006964, and WO01/27068, and WO01/62341; (23) serotonin reuptake inhibitors such as dexfenfluramine, fluoxetine, paroxetine, sertraline, and the compounds disclosed in U.S. Pat. No. 6,365,633, and WO01/27060, and WO01/162341; (24) GLP-1 (glucagon-like peptide-1) agonists; (25) topiramate (Topimax®); (26) Phytopharm compound 57 (CP644,673); (27) ACC2 (acetyl-CoA carboxylase-2) inhibitors; (28) β3 (β-adrenergic receptor-3) agonists such as AD9677/TAK677 (Dainippon/Takeda), CL-316, 243, SB418790, BRL-37344, L-796568, BMS-196085, BRL-35135A, CGP12177A, BTA-243, GW427353, trecadrine, Zeneca D7114, SR59119A, and the compounds disclosed in U.S. patent application Ser. No. 5,705,515, U.S. Pat. No. 5,451,677, and WO94/18161, WO95/29159, WO97/46556, WO98/04526, WO98/32753, WO01/74782 and WO02/32897; (29) DGAT1 (diacylglycerol acyltransferase-1) inhibitors; (30) DGAT2 (diacylglycerol acyltransferase-2) inhibitors; (31) FAS (fatty acid synthase) inhibitors such as cerulenin, C75; (32) PDE (phosphodiesterase) inhibitors such as theophylline, pentoxifylline, zaprinast, sildenafil, amrinone, milrinone, cilostamide, rolipram, and cilomilast; (33) thyroid hormone-β agonists such as KB-2611 (KaroBioBMS), and the compounds disclosed in WO02/15845 and Japanese Patent Application No. JP2000256190; (34) UCP-1 (uncoupling protein-1), 2 and 3 activators such as phytanic acid, 4-[(E)-2-(5,6,7,8-tetrahydro-5,5,8,8-tetramethyl-2-naphthalenyl)-1-propenyl]benzoic acid (TTNPB), retinoic acid, and the compounds disclosed in WO99/00123; (35) acyl-estrogens such as oleoyl-estrones disclosed in del Mar-Grasa, M. et al., *Obesity Research*, 9:202-209 (2001); (36) glucocorticoid antagonists; (37) 11βHSD-1 (11-β-hydroxysteroid dehydrogenase type 1) inhibitors such as BVT3498, BVT2733, and the compounds disclosed in WO01/90091, WO01/90090, and WO01/90092, and U.S. Pat. No. 6,730,690 and USP Application No. 2004/0133011; (38) SCD-1 (stearoyl-CoA desaturase-1) inhibitors; (39) dipeptidyl peptidase IV (DP-IV) inhibitors such as isoleucine thiazolidide, valine pyrrolidide, NVP-DPP728, LAF237, P93/01, TSL225, TMC-2A/2B/2C, FE999011, P9310/K364, VIP0177, SDZ274-444, and the compounds disclosed in U.S. Pat. No. 6,699,871, WO03/004498, WO03/004496, EP1258476, WO02/083128, WO02/062764, WO03/000250, WO03/002530, WO03/002531, WO03/002553, WO03/002593, WO03/000180, and WO03/000181; (40) lipase inhibitors such as tetrahydrolipstatin (orlistat/Xenical®), Triton WR1339, RHC80267, lipstatin. teasaponin, diethylumbelliferyl phosphate, FL-386, WAY-121898, Bay-N-3176, valilactone, esteracin, ebelactone A, ebelactone B, RHC80267, and the compounds disclosed in WO01/77094, U.S. Pat. Nos. 4,598,089, 4,452,813, 5,512,565, 5,391,571, 5,602,151, 4,405,644, 4,189,438, and 4,242,453; (41) fatty acid transporter inhibitors; (42) dicarboxylate transporter inhibitors; (43) glucose transporter inhibitors; (44) phosphate transporter inhibitors; (45) melanocortin agonists such as melanotan II and the compounds described in WO99/64002, and WO00/746799; (46) melanin condensating hormone antagonists such as the compounds disclosed in WO01/21577 and WO01/21169; (47) galanin antagonists; (48) CCK agonists; (49) corticotropin-releasing hormone agonists; and (50) phosphodiesterase-3B (PDE3B) inhibitors; (51) 5HT-2 agonists; (52) histamine receptor-3 (H3) modulators; (53) β-hydroxy steroid dehydrogenase-1 inhibitors (β-HSD-1); (54) anti-obesity serotonergic agents, such as fenfluramine, dexfenfluramine, phentermine, and sibutramine; (55) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. Nos. 5,026,685, 5,604,203, 5,574,010, 5,696,093, 5,936,092, 6,046,162, 6,046,167, 6,093,692, 6,225,445, 5,604,203, 4,002,531, 4,179,337, 5,122,614, 5,349,052, 5,552,520, 6,127,355, WO 95/06058, WO 98/32466, WO 03/026591, WO 03/057235, WO 03/027637, and WO 2004/066966, which are incorporated herein by reference; (56) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (57) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (58) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (59) aminorex; (60) amphechloral; (61) amphetamine; (62) benzphetamine; (63) chlorphentermine; (64) clobenzorex; (65) cloforex; (66) clominorex; (67) clortermine; (68) cyclexedrine; (69) dextroamphetamine; (70) diphemethoxidine, (71) N-ethylamphetamine; (72) fenbutrazate; (73) fenisorex; (74) fenproporex; (75) fludorex; (76) fluminorex; (77) furfurylmethylamphetamine; (78) levamfetamine; (79) levophacetoperane; (80) mefenorex; (81) metamfepramone; (82) methamphetamine; (83) norpseudoephedrine; (84) pentorex; (85) phendimetrazine; (86) phenmetrazine; (87) picilorex; (88) zonisamide, and (89) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; and 90) Qnexa; and (e) (1) Glucagon Receptor Agonists; (2) G Protein Receptor Agonist-40 (GPR-40) also called SNORF 55 such as BG 700, and those disclosed in WO 04/041266, 04/022551, 03/099793; (3) G Protein Receptor Agonist-119 (GPR119, also called RUP3; SNORF 25)—such as RUP3, HGPRBMY26, PFI 007, SNORF 25; (4) Selective Peroxisome Proliferator Activator Receptor Modulator (SPPARMS, also known as selective PPAR gamma modulators)—such as T131 (Amgen), FK614 (Fujisawa), netoglitazone, and metaglidasen; (5) oxyntomodulin; (6) SGLT inhibitors (sodium dependent glucose transporter inhibitors)—such as AVE 2268, KGT 1251, T1095/RWJ 394718.

The present agent may be combined with non-drug therapy such as kinesitherapy, dietetic treatment, and radiation therapy.

The compound and the combined compositions of the invention are effective for treating and preventing diabetes. The term "diabetes" as used herein includes both insulin-dependent diabetes (that is, also known as IDDM, type-1 diabetes), and insulin-independent diabetes (that is, also known as NIDDM, type-2 diabetes).

Diabetes is characterized by a fasting plasma glucose level of greater than or equal to 126 mg/dl. A diabetic subject has a fasting plasma glucose level of greater than or equal to 126 mg/dl. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of $\geq$140 mg/dl and <200 mg/dl); or insulin resistance, resulting in an increased risk of developing diabetes.

The compounds and compositions of the invention are useful for treatment of both type-1 diabetes and type-2 diabetes. The compounds and compositions are especially useful for treatment of type-2 diabetes. The compounds and compositions of the invention are especially useful for treatment and/or prevention of pre-diabetes. Also, the compounds and compositions of the invention are especially useful for treatment and/or prevention of gestational diabetes mellitus.

Treatment of diabetes mellitus refers to the administration of a compound or combination of the present invention to treat a diabetic subject. One outcome of the treatment of diabetes is to reduce an increased plasma glucose concentration. Another outcome of the treatment of diabetes is to reduce an increased insulin concentration. Still another outcome of the treatment of diabetes is to reduce an increased blood triglyceride concentration. Still another outcome of the treatment of diabetes is to increase insulin sensitivity. Still another outcome of the treatment of diabetes may be enhancing glucose tolerance in a subject with glucose intolerance. Still another outcome of the treatment of diabetes is to reduce insulin resistance. Another outcome of the treatment of diabetes is to lower plasma insulin levels. Still another outcome of treatment of diabetes is an improvement in glycemic control, particulary in type 2 diabetes. Yet another outcome of treatment is to increase hepatic insulin sensitivity.

Prevention of diabetes mellitus, in particular diabetes associated with obesity, refers to the administration of a compound or combination of the present invention to prevent or treat the onset of diabetes in a subject in need thereof. A subject in need of preventing diabetes in a prediabetic subject.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated, and isolated systolic hypertension, in which only the systolic pressure is elevated to greater than or equal to 140 mm Hg, while the diastolic pressure is less than 90 mm Hg. One outcome of treatment is decreasing blood pressure in a subject with high blood pressure.

Dyslipidemias or disorders of lipid metabolism, include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and BM). Dyslipidemia includes atherogenic dyslipidemia. Hyperlipidemia is associated with abnormally high levels of lipids, LDL and VLDL cholesterol, and/or triglycerides. An outcome of the treatment of dyslipidemia, including hyperlipemia, is to reduce an increased LDL cholesterol concentration. Another outcome of the treatment is to increase a low-concentration of HDL cholesterol. Another outcome of treatment is to decrease very low density lipoproteins (VLDL) and/or small density LDL.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "obesity" as used herein is a condition in which there is an excess of body fat, and includes visceral obesity. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians than that in Europeans and Americans. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, impaired glucose tolerance, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be decreasing body fat, including visceral body fat. Another outcome of treatment may be preventing body weight gain. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type 2 diabetes, polycystic ovary disease, cardiovascular diseases, osteoarthritis, dermatological disorders, hypertension, insulin resistance, hypercholesterolemia, hypertriglyceridemia, and cholelithiasis.

The invention is described more concretely with reference to Examples and Reference Examples mentioned below, which, however, do not restrict the invention.

In thin-layer chromatography in Examples, Silica gel$_{60}$F$_{254}$ (Merck) was used as the plate; and a UV detector was used for detection. In column silica gel, used was Wakogel™ C-300 or C-200 (Wako Jun-yaku), FLASH+ cartridge (Biotage), Chromatorex (FUJI SILYSIA CHEMICAL) or Purif-Pack (Moritex). In revers phase column chromatography, used was C18 catridge (Biotage). In high-performance partitioning liquid chromatography, used was ODS (C18) filler. The MS spectrum was determined through electrospray ionization (ESI), using Micromass ZQ 2000 (Waters). In NMR spectrometry, used was dimethylsulfoxide as the internal standard in a heavy dimethylsulfoxide solution, or used was tetramethylsilane as the internal standard in a heavy chloroform solution. For it, used was a spectrophotometer of JNM—AL400 (JEOL), Mercury 400 (400 MHz; Varian) or Inova 400 (400 MHz; Varian), and the total δ value was shown as ppm.

Abbreviations in experimental section have the following meanings. s: singlet; d: doublet; dd: double doublet; t: triplet;

dt: double triplet; q: quartet; m: multiplet; br: broad; br m: broad multiplet; J: coupling constant; Hz: hertz; DMSO-$d_6$: heavy dimethylsulfoxide; $CDCl_3$: heavy chloroform; $Ac_2O$: acetic anhydride; $B(OMe)_3$: trimethoxyborane; Boc: tert-butoxycarbonyl; CDI: N,N'-carbonyldiimidazole; $Cu(OAc)_2$: copper (II) acetate; DBU: 1,8-diazabicyclo[5.4.0]undec-7-ene; DME: 1,2-dimethoxyethane; DMF: dimethylformamide; DPPF: 1,1'-bis(diphenylphosphino)ferrocene; $Et_2O$: diethyl ether; EtO: ethoxy; EtOAc: ethyl acetate; EtOH: ethanol; h.: hour(s); HOBT: 1-hydroxybenzotriazole hydrate; HPLC: high-performance liquid chromatography; KOAc: potassium acetate; Me: methyl; MeCN: acetonitrile; MeOH: methanol; min.: minute(s); n-BuLi: n-butyl lithium; ODS: C18; $PdCl_2$(dppf): 1,1-bis(diphenylphosphino)ferrocene palladium dichloride; $Pd(OAc)_2$: palladium(II) acetate; $Pd(PPh_3)_4$: tetraki(triphenylphosphine)palladium(0); S-phos: 2-dicyclohexylphosphino-2',6'-dimethoxybiphenyl; TBAB: tetrabuthylammonium bromide; t-Bu: tert-butyl; t-BuOH: tert-butanol; TEA: triethylamine; TFA: trifluoroacetic acid; TfO: trifluoromethanesulfonyloxy; $Tf_2O$: triflic anhydride; THF: tetrahydrofuran; TLC: thin-layer chromatgraphy; and WSCDI: N-(3-dimethylaminopropyl)-N'-ethylcarbodiimide hydrochloride.

In the following structural formulae, the expression of the hydrogen atom in the group of —NH— or —$NH_2$ may be omitted for convenience's sake, and the group may be expressed as —N— or —N.

EXAMPLE 1

4'-({6-(5-Carbamoylpyridin-3-yl)-4-oxospiro[chroman-2,4'-piperidin]-1'-yl}carbonyl)-2',6'-diethoxybiphenyl-3-carboxylic acid

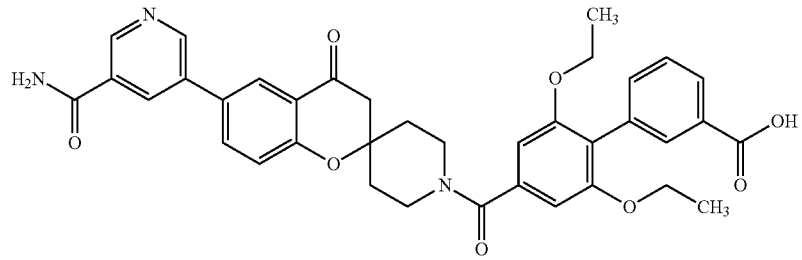 [SMILES: CCOc1cc(C(=O)N2CCC3(CC2)CC(=O)c2cc(-c4cncc(C(N)=O)c4)ccc2O3)cc(OCC)c1-c1cccc(C(=O)O)c1]

TEA (0.081 ml, 0.581 mmol) was added to a stirred mixture of HOBT (21.35 mg, 0.139 mmol), WSCDI (26.7 mg, 0.139 mmol), 5-(4-oxospiro[chroman-2,4'-piperidin]-6-yl)nicotinamide dihydrochloride (57.2 mg, 0.139 mmol) and 2,6-diethoxy-3'-(methoxycarbonyl)biphenyl-4-carboxylic acid (40 mg, 0.116 mmol) in DMF (1 ml) and the mixture was stirred at room temperature overnight. The reaction mixture was poured into water (20 ml) and stirred for 30 min. The resulted precipitate was filtered, washed with water and the solid was dried in vacuo at 70° C. to give the crude coupling product as a brown solid.

Aqueous 1N NaOH (0.5 ml, 0.500 mmol) was added to a stirred solution of the coupling product in THF (1 ml)-MeOH (1 ml) and the mixture was stirred at room temperature overnight. Aqueous 1N HCl (0.5 ml) was added to the mixture and the solvent was evaporated under reduced pressure. The residue was suspended in $CHCl_3$-MeOH (8:2) and the mixture stirred for 1 h at room temperature. The insoluble material was filtered off and the filtrate was concentrated in vacuo. The crude material was purified by preparative HPLC (ODS, 0.1% HCOOH in $H_2O$/MeCN, gradient) to give intended compound (28.8 mg, 0.044 mmol, 38.2% yield) as a colorless solid.

$^1$H-NMR (DMSO-$D_6$) δ: 12.96-12.64 (1.0H, br m), 8.96 (1.0H, d, J=2.0 Hz), 8.93 (1.0H, d, J=2.0 Hz), 8.42 (1.0H, dd, J=2.0, 2.0 Hz), 8.24 (1.0H, s), 8.07 (1.0H, d, J=2.3 Hz), 8.01 (1.0H, dd, J=8.6, 2.3 Hz), 7.84-7.76 (2.0H, m), 7.61 (1.0H, s), 7.51-7.46 (1.0H, m), 7.42 (1.0H, dd, J=7.4, 7.4 Hz), 7.22 (1.0H, d, J=8.6 Hz), 6.69 (2.0H, s), 4.29-4.17 (1.0H, m), 3.95 (4.0H, q, J=7.0 Hz), 3.61-3.35 (2.0H, m), 3.30-3.15 (1.0H, m), 2.91 (2.0H, s), 2.06-1.86 (2.0H, m), 1.83-1.72 (2.0H, m), 1.09 (6.0H, t, J=7.0 Hz).

MS[M+H]+=650.5

EXAMPLE 2

2',6'-Diethoxy-4'-{[6-(1H-pyrazol-5-yl)-4-oxospiro[chroman-2,4'-piperidin]-1'-yl]carbonyl}biphenyl-4-carboxylic acid

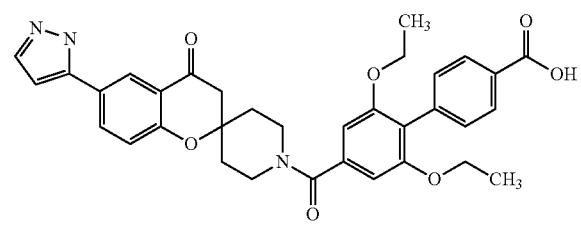 [SMILES: CCOc1cc(C(=O)N2CCC3(CC2)CC(=O)c2cc(-c4ccn[nH]4)ccc2O3)cc(OCC)c1-c1ccc(C(=O)O)cc1]

In the same manner as in Example 1, the intended compound was obtained as a colorless solid from 6-(1H-pyrazol-5-yl)spiro[chroman-2,4'-piperidin]-4-one hydrochloride and 2,6-diethoxy-4'-(methoxycarbonyl)biphenyl-4-carboxylic acid.

$^1$H-NMR (DMSO-D6) δ: 13.01-12.69 (1.0H, br m), 8.07 (1.0H, d, J=2.3 Hz), 7.97 (1.0H, dd, J=8.6, 2.3 Hz), 7.86 (2.0H, d, J=8.2 Hz), 7.66 (1.0H, s), 7.35 (2.0H, d, J=8.2 Hz), 7.09 (1.0H, d, J=8.6 Hz), 6.68 (2.0H, s), 6.64 (1.0H, d, J=2.0 Hz), 4.25-4.17 (1.0H, m), 3.94 (4.0H, q, J=7.0 Hz), 3.58-3.56 (2.0H, m), 3.32-3.13 (1.0H, m), 2.86 (2.0H, s), 2.06-1.85 (2.0H, m), 1.80-1.69 (2.0H, m), 1.09 (6.0H, t, J=7.0 Hz).

MS[M+H]+=596.4

EXAMPLE 3

4'-({6-(4-Carbamoylphenyl)-4-oxospiro[chroman-2,4'-piperidin]-1'-yl}carbonyl)-2',6'-diethoxybiphenyl-4-carboxylic acid

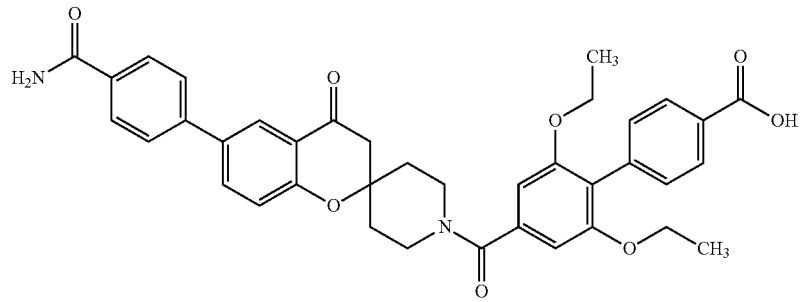 [SMILES: CCOc1cc(C(=O)N2CCC3(CC2)CC(=O)c2cc(-c4ccc(C(N)=O)cc4)ccc2O3)cc(OCC)c1-c1ccc(C(=O)O)cc1]

In the same manner as in Example 1, the intended compound was obtained as a colorless solid from 4-(4-oxospiro[chroman-2,4'-piperidin]-6-yl)benzamide hydrochloride and 2,6-diethoxy-4'-(methoxycarbonyl)biphenyl-4-carboxylic acid.

$^1$H-NMR (DMSO-D$_6$) δ: 12.87-12.76 (1.0H, br m), 7.98-7.92 (3.0H, m), 7.90 (2.0H, d, J=8.2 Hz), 7.86 (2.0H, d, J=8.2 Hz), 7.68 (2.0H, d, J=8.2 Hz), 7.35 (2.0H, d, J=8.2 Hz), 7.32 (1.0H, s), 7.17 (1.0H, d, J=8.6 Hz), 6.69 (2.0H, s), 4.30-4.15 (1.0H, m), 3.95 (4.0H, q, J=7.0 Hz), 3.59-3.36 (2.0H, m), 3.26-3.14 (1.0H, m), 2.89 (2.0H, s), 2.08-1.86 (2.0H, m), 1.83-1.70 (2.0H, m), 1.10 (6.0H, t, J=7.0 Hz).

MS[M+H]+=649.5

EXAMPLE 4

4'-({6-(3-Carbamoylphenyl)-4-oxospiro[chroman-2,4'-piperidin]-1'-yl}carbonyl)-2',6'-diethoxybiphenyl-4-carboxylic acid

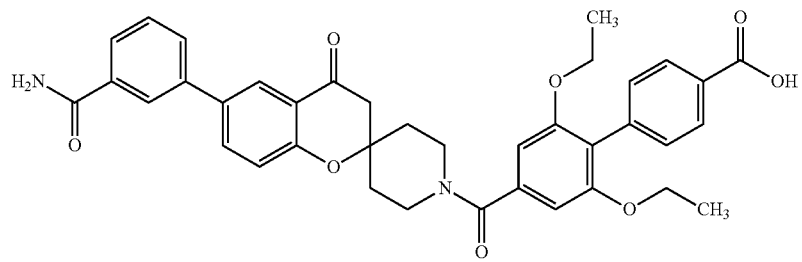 [SMILES: CCOc1cc(C(=O)N2CCC3(CC2)CC(=O)c2cc(-c4cccc(C(N)=O)c4)ccc2O3)cc(OCC)c1-c1ccc(C(=O)O)cc1]

In the same manner as in Example 1, the intended compound was obtained as a colorless solid from 3-(4-oxospiro[chroman-2,4'-piperidin]-6-yl)benzamide hydrochloride and 2,6-diethoxy-4'-(methoxycarbonyl)biphenyl-4-carboxylic acid.

$^1$H-NMR (DMSO-D$_6$) δ: 12.82 (1.0H, s), 8.09 (2.0H, s), 8.01 (1.0H, d, J=2.7 Hz), 7.94 (1.0H, dd, J=8.6, 2.7 Hz), 7.86 (2.0H, d, J=8.6 Hz), 7.79 (1.0H, d, J=7.8 Hz), 7.75 (1.0H, d, J=7.8 Hz), 7.48 (1.0H, dd, J=7.8, 7.8 Hz), 7.39-7.36 (1.0H, m), 7.35 (2.0H, d, J=8.6 Hz), 7.18 (1.0H, d, J=8.6 Hz), 6.68 (2.0H, s), 4.30-4.14 (1.0H, m), 3.95 (4.0H, q, J=7.0 Hz), 3.60-3.38 (2.0H, m), 3.30-3.14 (1.0H, m), 2.89 (2.0H, s), 2.07-1.87 (2.0H, m), 1.82-1.72 (2.0H, m), 1.10 (6.0H, t, J=7.0 Hz).

MS[M+H]+=649.5

EXAMPLE 5

4'-({6-5-Carbamoylpyridin-2-yl)-4-oxospiro[chroman-2,4'-piperidin]-1'-yl}carbonyl)-2',6'-diethoxybiphenyl-4-carboxylic acid

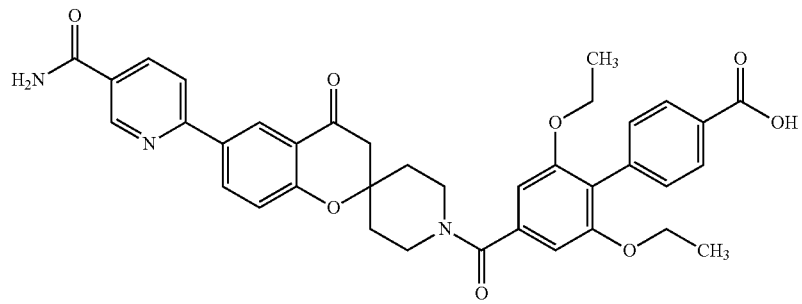 [SMILES: CCOc1cc(C(=O)N2CCC3(CC2)CC(=O)c2cc(-c4ccc(C(N)=O)cn4)ccc2O3)cc(OCC)c1-c1ccc(C(=O)O)cc1]

In the same manner as in Example 1, the intended compound was obtained as a colorless solid from 6-(4-oxospiro[chroman-2,4'-piperidin]-6-yl)nicotinamide hydrochloride and 2,6-diethoxy-4'-(methoxycarbonyl)biphenyl-4-carboxylic acid.

Alternatively, sodium 4'-({6-(5-carbamoylpyridin-2-yl)-4-oxospiro[chroman-2,4'-piperidin]-1'-yl}carbonyl)-2',6'-diethoxybiphenyl-4-carboxylate (500 mg, 0.744 mmol) was suspended in H$_2$O (25 ml) and aqueous 1N HCl (0.744 ml, 0.744 mmol) was added thereto, after stirring for 30 min, MeOH (25 ml) was added thereto and stirred for 30 min. After the precipitate was collected by filtration, the solid was washed by H$_2$O-MeOH, and dried in vacuo. The obtained crude product was suspended in MeOH (20 ml) and stirred at 100° C. for 2 h (still suspension). After cooling at room temperature, the precipitate was collected by filteration, washed with MeOH, and dried in vacuo at 60° C. to afford the intended compound (445 mg, 92% yield) as a cololess crystal.

$^1$H-NMR (DMSO-D$_6$) δ: 12.82 (1.0H, s), 9.03 (1.0H, d, J=2.3 Hz), 8.47 (1.0H, d, J=2.3 Hz), 8.34 (1.0H, dd, J=8.6, 2.3 Hz), 8.22 (1.0H, dd, J=8.6, 2.3 Hz), 8.12 (1.0H, s), 8.02 (1.0H, d, J=8.6 Hz), 7.86 (2.0H, d, J=8.6 Hz), 7.53 (1.0H, s), 7.34 (2.0H, d, J=8.6 Hz), 7.19 (1.0H, d, J=8.6 Hz), 6.69 (2.0H, s), 4.30-4.17 (1.0H, m), 3.95 (4.0H, q, J=7.0 Hz), 3.58-3.36 (2.0H, m), 3.29-3.15 (1.0H, m), 2.90 (2.0H, s), 2.07-1.87 (2.0H, m), 1.82-1.73 (2.0H, m), 1.10 (6.0H, t, J=7.0 Hz).

MS[M+H]+=650.6

EXAMPLE 6

4'-({6-(5-Carbamoylpyridin-3-yl)-4-oxospiro[chroman-2,4'-piperidin]-1'-yl}carbonyl)-2',6'-diethoxybiphenyl-4-carboxylic acid

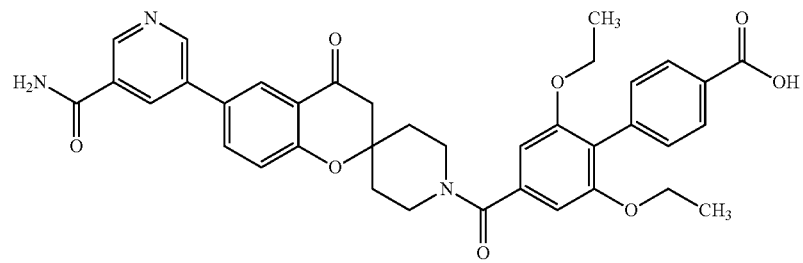 [SMILES: CCOc1cc(C(=O)N2CCC3(CC2)CC(=O)c2cc(-c4cncc(C(N)=O)c4)ccc2O3)cc(OCC)c1-c1ccc(C(=O)O)cc1]

In the same manner as in Example 1, the intended compound was obtained as a colorless solid from 5-(4-oxospiro[chroman-2,4'-piperidin]-6-yl)nicotinamide dihydrochloride and 2,6-diethoky-4'-(methoxycarbonyl)biphenyl-4-carboxylic acid.

$^1$H-NMR (DMSO-D$_6$) δ: 12.82 (1.0H, s), 8.95 (2.0H, br s), 8.42 (1.0H, s), 8.24 (1.0H, s), 8.07 (1.0H, d, J=2.3 Hz), 8.01 (1.0H, dd, J=8.6, 2.3 Hz), 7.86 (2.0H, d, J=8.2 Hz), 7.61 (1.0H, s), 7.35 (2.0H, d, J=8.2 Hz), 7.22 (1.0H, d, J=8.6 Hz), 6.69 (2.0H, s), 4.29-4.16 (1.0H, m), 3.95 (4.0H, q, J=7.0 Hz), 3.60-3.37 (2.0H, m), 3.31-3.14 (1.0H, m), 2.90 (2.0H, s), 2.06-1.87 (2.0H, m), 1.83-1.72 (2.0H, m), 1.10 (6.0H, t, J=7.0 Hz).

MS[M+H]+=650.5

EXAMPLE 7

4-(8-Cyclopropyl-2-{[6-(1-methyl-1H-pyrazol-4-yl)-4-oxospiro[chroman-2,4'-piperidin]-1'-yl]carbonyl}quinolin-4-yl)benzoic acid

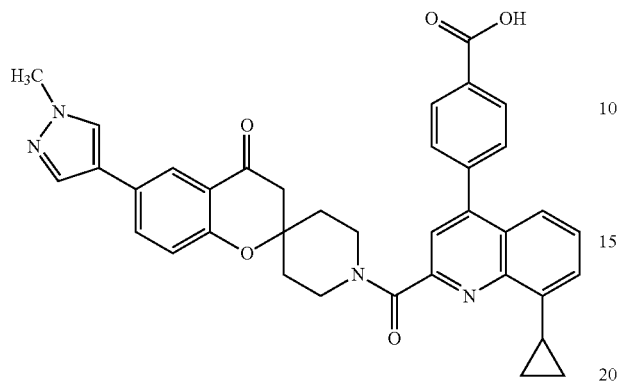

Aqueous 1N NaOH (0.500 ml, 0.500 mmol) was added to a stirred solution of methyl 4-(8-cyclopropyl-2-{[6-(1-methyl-1H-pyrazol-4-yl)-4-oxospiro[chroman-2,4'-piperidin]-1'-yl]carbonyl}quinolin-4-yl)benzoate (160 mg, 0.255 mmol) in THF (1 ml)-MeOH (1 ml) and the mixture was stirred at room temperature overnight. Aqueous 1N HCl (0.5 ml) was added to the mixture and the solvent was evaporated under reduced pressure. The residue was suspended in CHCl$_3$-MeOH (8:2) and the mixture stirred for 1 h. at room temperature. The insoluble material was filtered off and the filtrate was concentrated in vacuo. The residue was purified by preparative TLC (CHCl$_3$/MeOH=92/8) and the product was precipitated with CHCl$_3$/hexane to give intended compound (106 mg, 0.173 mmol, 67.8% yield) as a pale yellow solid.

$^1$H-NMR (DMSO-D$_6$) δ: 13.14 (1.0H, s), 8.12-8.06 (3.0H, m), 7.80-7.78 (2.0H, m), 7.75 (1.0H, dd, J=8.6, 2.3 Hz), 7.64 (2.0H, d, J=8.6 Hz), 7.61 (1.0H, s), 7.57 (1.0H, d, J=8.6 Hz), 7.50 (1.0H, dd, J=7.4, 7.4 Hz), 7.30 (1.0H, d, J=7.4 Hz), 7.09 (1.0H, d, J=8.6 Hz), 4.37-4.29 (1.0H, m), 3.99-3.92 (1.0H, m), 3.80 (3.0H, s), 3.57-3.48 (1.0H, m), 3.29-3.26 (1.0H, m), 3.15-3.08 (1.0H, m), 2.87 (2.0H, s), 2.09-2.02 (1.0H, m), 1.98-1.76 (3.0H, m), 1.10-1.05 (2.0H, m), 0.84-0.77 (2.0H, m).
MS[M+H]+=613.4

EXAMPLE 8

4-(3-Methyl-6-{[6-(1-methyl-1H-pyrazol-4-yl)-4-oxospiro[chroman-2,4'-piperidin]-1'-yl]carbonyl}-1H-indazol-1-yl)benzoic acid

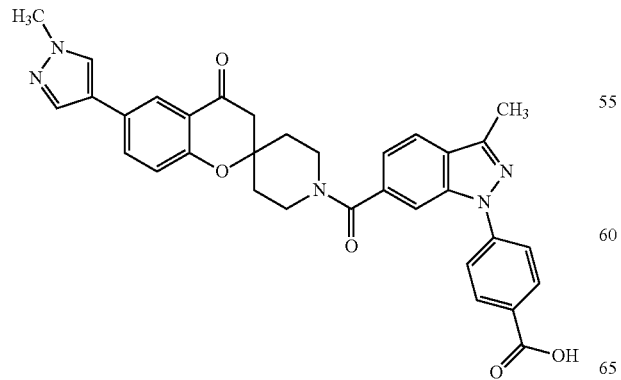

In the same manner as in Example 7, the intended compound was obtained as a colorless solid using methyl 4-(3-methyl-6-{[6-(1-methyl-1H-pyrazol-4-yl)-4-oxospiro[chroman-2,4'-piperidin]-1'-yl]carbonyl}-1H-indazol-1-yl)benzoate.

$^1$H-NMR (DMSO-D6) δ: 12.99 (1.0H, s), 8.10-8.06 (3.0H, m), 7.91-7.88 (2.0H, m), 7.87 (2.0H, d, J=8.6 Hz), 7.79-7.77 (2.0H, m), 7.73 (1.0H, dd, J=8.6, 2.3 Hz), 7.26 (1.0H, d, J=8.6 Hz), 7.05 (1.0H, d, J=8.6 Hz), 4.31-4.20 (1.0H, br m), 3.79 (3.0H, s), 3.46-3.12 (3.0H, m), 2.83 (2.0H, s), 2.57 (3.0H, s), 2.05-1.95 (1.0H, br m), 1.88-1.64 (3.0H, br m).
MS[M+H]+=576.3

EXAMPLE 9

3-(3-Methyl-6-{[6-(1-methyl-1H-pyrazol-4-yl)-4-oxospiro[chroman-2,4'-piperidin]-1'-yl]carbonyl}-1H-indazol-1-yl)benzoic acid

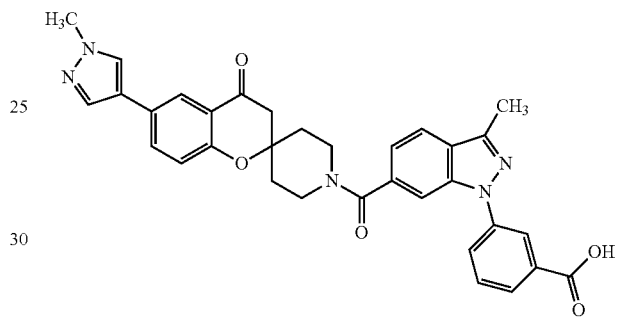

In the same manner as in Example 7, the intended compound was obtained as a colorless solid using methyl 3-(3-methyl-6-{[6-(1-methyl-1H-pyrazol-4-yl)-4-oxospiro[chroman-2,4'-piperidin]-1'-yl]carbonyl}-1H-indazol-1-yl)benzoate.

$^1$H-NMR (DMSO-D$_6$) δ: 13.26 (1.0H, br s), 8.22-8.19 (1.0H, m), 8.08 (1.0H, s), 7.98 (1.0H, dd, J=8.2, 2.3 Hz), 7.91-7.87 (2.0H, m), 7.79-7.76 (3.0H, m), 7.73 (1.0H, dd, J=8.2, 2.3 Hz), 7.66 (1.0H, dd, J=7.8, 7.8 Hz), 7.25 (1.0H, d, J=8.6 Hz), 7.04 (1.0H, d, J=8.6 Hz), 4.31-4.19 (1.0H, br m), 3.79 (3.0H, s), 3.51-3.14 (3.0H, m), 2.82 (2.0H, s), 2.57 (3.0H, s), 2.07-1.92 (1.0H, m), 1.90-1.63 (3.0H, m).
MS[M+H]+=576.3

EXAMPLE 10

4-(1-Cyclopropyl-3-methyl-6-{[6-(1-methyl-1H-pyrazol-4-yl)-4-oxospiro[chroman-2,4'-piperidin]-1'-yl]carbonyl}-1H-indol-4-yl)benzoic acid

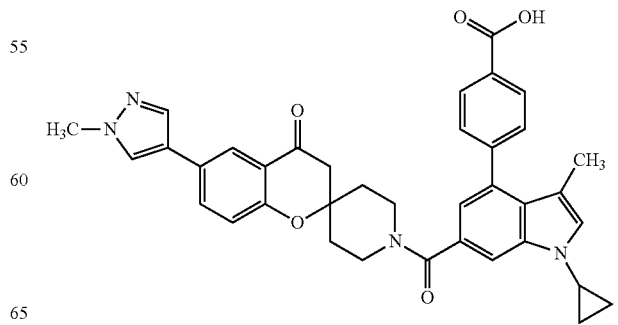

In the same manner as in Example 7, the intended compound was obtained as a colorless solid using methyl 4-(1-cyclopropyl-3-methyl-6-{[6-(1-methyl-1H-pyrazol-4-yl)-4-oxospiro[chroman-2,4'-piperidin]-1'-yl]carbonyl}-1H-indol-4-yl)benzoate.

$^1$H-NMR (DMSO-D6) δ: 12.97 (1.0H, br s), 8.09 (1.0H, s), 7.96 (2.0H, d, J=8.2 Hz), 7.80-7.77 (2.0H, m), 7.74 (1.0H, dd, J=8.6, 2.3 Hz), 7.59 (1.0H, d, J=1.2 Hz), 7.46 (2.0H, d, J=8.2 Hz), 7.22 (1.0H, d, J=1.2 Hz), 7.06 (1.0H, d, J=8.6 Hz), 6.89 (1.0H, d, J=1.2 Hz), 4.33-4.07 (1.0H, br m), 3.85-3.19 (4.0H, m), 3.79 (3.0H, s), 2.76 (2.0H, d, J=64.1 Hz), 1.99-1.98 (2.0H, br m), 1.79-1.68 (2.0H, m), 1.70 (3.0H, s), 1.06-1.00 (2.0H, m), 0.94-0.88 (2.0H, m).

MS[M+H]+=615.4

EXAMPLE 11

1-(1-Cyclopropyl-6-{[6-(1-methyl-1H-pyrazol-4-yl)-4-oxospiro[chroman-2,4'-piperidin]-1'-yl]carbonyl}-1H-indol-4-yl)piperidine-4-carboxylic acid

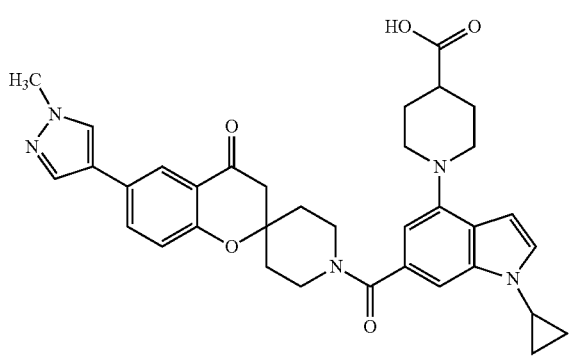 [SMILES: Cn1cc(-c2ccc3c(c2)C(=O)CC2(CCN(C(=O)c4cc(N5CCC(C(=O)O)CC5)c5ccn(C6CC6)c5c4)CC2)O3)cn1]

Aqueous 1N NaOH (0.409 ml, 0.409 mmol) was added to a stirred solution of ethyl 1-(1-cyclopropyl-6-{[6-(1-methyl-1H-pyrazol-4-yl)-4-oxospiro[chroman-2,4'-piperidin]-1'-yl]carbonyl}-1H-indol-4-yl)piperidine-4-carboxylate in THF (1 ml)-MeOH (1 ml) and the mixture was stirred at room temperature overnight. Aqueous 1N HCl (0.409 ml) was added to the mixture and the solvent was evaporated under reduced pressure. The residue was suspended in CHCl$_3$-MeOH (8:2) and the mixture stirred for 1 h. at room temperature. The insoluble material was filtered off and the filtrate was concentrated in vacuo. The crude material was purified by preparative HPLC (ODS, 0.1% HCOOH in H$_2$O/MeCN, gradient) to give intended compound (44.4 mg, 0.073 mmol, 35.7% yield) as a pale orange solid.

$^1$H-NMR (DMSO-D$_6$) δ: 12.18 (1.0H, s), 8.09 (1.0H, s), 7.80-7.77 (2.0H, m), 7.74 (1.0H, dd, J =8.6, 2.3 Hz), 7.28 (1.0H, d, J=3.1 Hz), 7.20 (1.0H, s), 7.07 (1.0H, d, J=8.6 Hz), 6.53-6.47 (1.0H, m), 6.35-6.31 (1.0H, m), 4.30-4.08 (1.0H, m), 3.79 (3.0H, s), 3.72-3.17 (8.0H, m), 2.85 (2.0H, s), 2.79-2.64 (2.0H, br m), 2.42-2.32 (1.0H, br m), 1.97-1.86 (3.0H, m), 1.82-1.67 (3.0H, m), 1.03-0.98 (2.0H, m), 0.90-0.86 (2.0H, m).

MS[M+H]+=608.6

EXAMPLE 12

3-(3-Methyl-5-{[6-(1-methyl-1H-pyrazol-4-yl)-4-oxospiro[chroman-2,4'-piperidin]-1'-yl]carbonyl}-1H-indazol-1-yl)benzoic acid

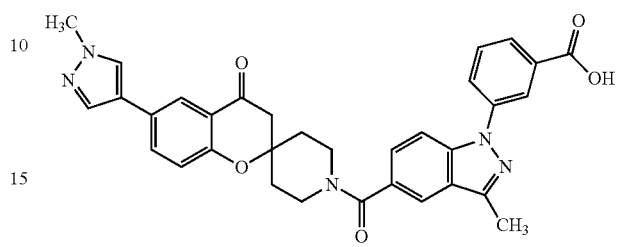

In the same manner as in Example 11, the intended compound was obtained as a colorless solid using methyl 3-(3-methyl-5-{[6-(1-methyl-1H-pyrazol-4-yl)-4-oxospiro[chroman-2,4'-piperidin]-1'-yl]carbonyl}-1H-indazol-1-yl)benzoate.

$^1$H-NMR (DMSO-D6) δ: 13.20 (1.0H, br s), 8.22-8.20 (1.0H, m), 8.09 (1.0H, s), 7.99 (1.0H, d, J =7.4 Hz), 7.92 (1.0H, s), 7.88 (1.0H, d, J=7.4 Hz), 7.83 (1.0H, d, J=8.6 Hz), 7.80-7.77 (2.0H, m), 7.75 (1.0H, dd, J=8.6, 2.3 Hz), 7.66 (1.0H, dd, J=7.8, 7.8 Hz), 7.53 (1.0H, dd, J=8.6, 1.2 Hz), 7.06 (1.0H, d, J=8.6 Hz), 4.39-4.14 (1.0H, br m), 3.79 (3.0H, s), 3.69-3.16 (3.0H, br m), 2.85 (2.0H, s), 2.58 (3.0H, s), 2.06-1.82 (2.0H, m), 1.80-1.70 (2.0H, m).

MS[M+H]+=576.3

EXAMPLE 13

4-(3-Methyl-5-{[6-(1-methyl-1H-pyrazol-4-yl)-4-oxospiro[chroman-2,4'-piperidin]-1'-yl]carbonyl}-1H-indazol-1-yl)benzoic acid

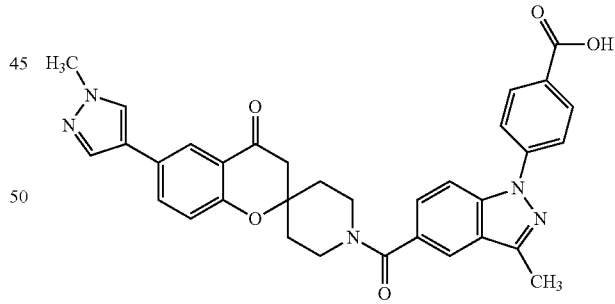

In the same manner as in Example 11, the intended compound was obtained as a colorless solid using methyl 4-(3-methyl-5-{[6-(1-methyl-1H-pyrazol-4-yl)-4-oxospiro[chroman-2,4'-piperidin]-1'-yl]carbonyl}-1H-indazol-1-yl) benzoate.

$^1$H-NMR (DMSO-D$_6$) δ: 13.06 (1.0H, s), 8.11-8.05 (3.0H, m), 7.97-7.92 (2.0H, m), 7.88 (2.0H, d, J=8.6 Hz), 7.81-7.77 (2.0H, m), 7.75 (1.0H, dd, J=8.6, 2.5 Hz), 7.54 (1.0H, dd, J=8.6, 1.6 Hz), 7.06 (1.0H, d, J=8.6 Hz), 4.38-4.13 (1.0H, br m), 3.79 (3.0H, s), 3.58-3.11 (3.0H, br m), 2.85 (2.0H, s), 2.58 (3.0H, s), 2.08-1.66 (4.0H, m).

MS[M+H]+=576.3

EXAMPLE 14

Sodium [(1-cyclopropyl-6-{[6-(1-methyl-1H-pyrazol-4-yl)-4-oxospiro[chroman-2,4'-piperidin]-1'-yl]carbonyl}-1H-indol-4-yl)oxy]acetate

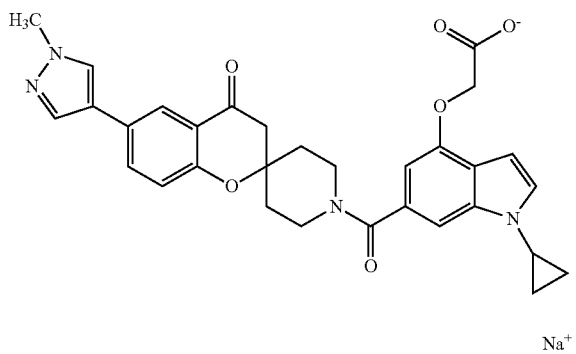 [SMILES: Cn1cc(-c2ccc3c(c2)C(=O)CC2(CCN(C(=O)c4cc(OCC(=O)[O-])c5ccn(C6CC6)c5c4)CC2)O3)cn1 ; [Na+]]

Aqueous 1N NaOH (0.604 ml, 0.604 mmol) was added to a stirred solution of methyl[(1-cyclopropyl-6-{[6-(1-methyl-1H-pyrazol-4-yl)-4-oxospiro[chroman-2,4'-piperidin]-1'-yl]carbonyl}-1H-indol-4-yl)oxy]acetate (229 mg, 0.403 mmol) in THF (1 ml)-MeOH (1 ml) and the mixture was stirred at room temperature for 2 days.
After water was added to the mixture, the organic solvents were evaporated under reduced pressure. The aqueous residue was purified by ODS column chromatography eluting with H$_2$O/MeOH to give the intended compound (156 mg, 0.271 mmol, 67.2% yield) as a pale yellow solid.
$^1$H-NMR (DMSO-D$_6$) δ: 8.09 (1.0H, s), 7.79-7.77 (2.0H, m), 7.74 (1.0H, dd, J=8.6, 2.3 Hz), 7.20 (1.0H, d, J=3.1 Hz), 7.10-7.07 (2.0H, m), 6.35 (1.0H, d, J=3.1 Hz), 6.31 (1.0H, s), 4.21-4.03 (1.0H, br m), 4.14 (2.0H, s), 3.84-3.57 (1.0H, br m), 3.79 (3.0H, s), 3.50-3.06 (3.0H, m), 2.84 (2.0H, s), 2.04-1.63 (4.0H, m), 1.03-0.97 (2.0H, m), 0.90-0.85 (2.0H, m).
MS[M+Na]+=577.3

EXAMPLE 15

2-(1-Cyclopropyl-6-{[6-(1-methyl-1H-pyrazol-4-yl)-4-oxospiro[chroman-2,4'-piperidin]-1'-yl]carbonyl}-1H-indol-4-yl)benzoic acid

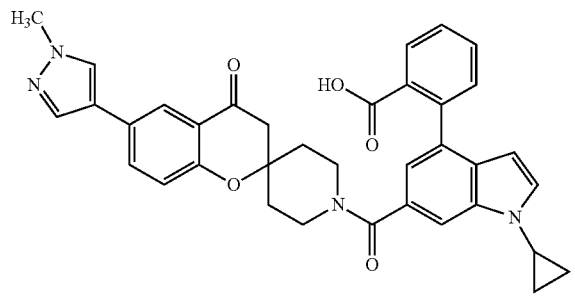 [SMILES: Cn1cc(-c2ccc3c(c2)C(=O)CC2(CCN(C(=O)c4cc(-c5ccccc5C(=O)O)c5ccn(C6CC6)c5c4)CC2)O3)cn1]

In the same manner as in Example 7, the intended compound was obtained as a colorless solid using methyl 2-(1-cyclopropyl-6-{[6-(1-methyl-1H-pyrazol-4-yl)-4-oxospiro[chroman-2,4'-piperidin]-1'-yl]carbonyl}-1H-indol-4-yl)benzoate.
$^1$H-NMR (DMSO-D$_6$) δ: 12.47 (1.0H, s), 8.09 (1.0H, s), 7.81-7.72 (4.0H, m), 7.59 (1.0H, s), 7.58-7.52 (1.0H, m), 7.47-7.38 (3.0H, m), 7.07 (1.0H, d, J=8.6 Hz), 6.90 (1.0H, d, J=1.2 Hz), 6.10 (1.0H, d, J=3.1 Hz), 4.35-4.02 (1.0H, br m), 3.85-3.57 (1.0H, br m), 3.79 (3.0H, s), 3.50-3.18 (3.0H, m), 2.84 (2.0H, s), 2.03-1.64 (4.0H, m), 1.09-1.02 (2.0H, m), 0.98-0.91 (2.0H, m).
MS[M+H]+=601.3

EXAMPLE 16

Sodium 3-(1-Cyclopropyl-6-{[6-(1-methyl-1H-pyrazol-4-yl)-4-oxospiro[chroman-2,4'-piperidin]-1'-yl]carbonyl}-1H-indol-4-yl)benzoate

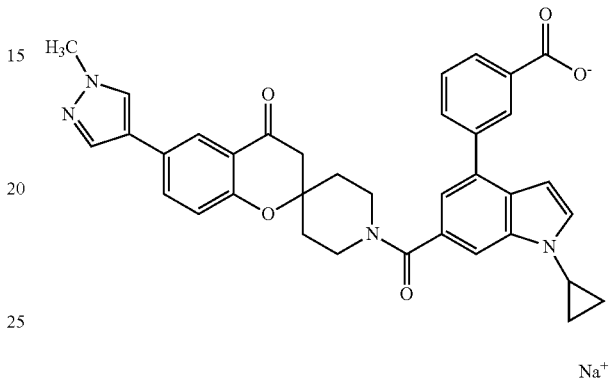

In the same manner as in Example 14, the intended compound was obtained as a colorless solid using methyl 3-(1-cyclopropyl-6-{[6-(1-methyl-1H-pyrazol-4-yl)-4-oxospiro[chroman-2,4'-piperidin]-1'-yl]carbonyl}-1H-indol-4-yl)benzoate.
$^1$H-NMR (DMSO-D$_6$) δ: 8.14 (1.0H, s), 8.09 (1.0H, s), 7.84 (1.0H, d, J=7.4 Hz), 7.80-7.77 (2.0H, in), 7.74 (1.1H, dd, J=8.6, 2.3 Hz), 7.58 (1.0H, s), 7.52 (1.0H, d, J=7.8 Hz), 7.46 (1.0H, d, J=3.1 Hz), 7.35 (1.0H, dd, J=7.8, 7.4 Hz), 7.13 (0.9H, s), 7.08 (1.0H, d, J=8.6 Hz), 6.47 (1.0H, d, J=3.1 Hz), 4.42-4.09 (1.0H, br m), 3.86-3.60 (1.0H, br m), 3.79 (3.0H, s), 3.52-3.21 (3.0H, m), 2.85 (2.0H, s), 2.02-1.66 (4.0H, m), 1.10-1.02 (2.0H, m), 0.98-0.92 (2.0H, m).
MS[M+Na]+=623.3

EXAMPLE 17

Sodium 4-(1-cyclopropyl-6-{[6-(1-methyl-1H-pyrazol-4-yl)-4-oxospiro[chroman-2,4'-piperidin]-1'-yl]carbonyl}-1H-indol-4-yl)benzoate

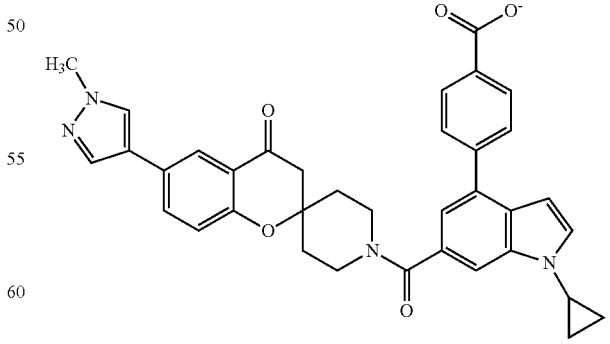

In the same manner as in Example 14, the intended compound was obtained as a colorless solid using methyl 4-(1- cyclopropyl-6-{[6-(1-methyl-1H-pyrazol-4-yl)-4-oxospiro[chroman-2,4'-piperidin]-1'-yl]carbonyl}-1H-indol-4-yl)benzoate.

$^1$H-NMR (DMSO-D$_6$) δ: 8.09 (1.0H, s), 7.94 (2.0H, d, J=7.8 Hz), 7.81-7.72 (3.0H, m), 7.58 (1.0H, s), 7.53-7.44 (3.0H, m), 7.14 (1.0H, s), 7.07 (1.0H, d, J=8.6 Hz), 6.49 (1.0H, d, J=2.3 Hz), 4.41-4.03 (1.0H, br m), 3.89-3.61 (1.0H, br m), 3.79 (3.0H, s), 3.53-3.14 (3.0H, m), 2.85 (2.0H, s), 2.07-1.67 (4.0H, m), 1.10-1.03 (2.0H, m), 0.99-0.91 (2.0H, m).

MS[M+Na]+=623.3

EXAMPLE 18

Sodium 2',6'-diethoxy-4'-{[6-(1-methyl-1H-pyrazol-4-yl)-4-oxospiro[chroman-2,4'piperidin]-1'-yl]carbonyl}biphenyl-4-carboxylate

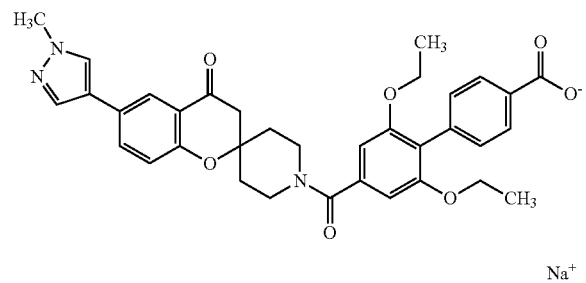 [SMILES: CCOc1cc(C(=O)N2CCC3(CC2)CC(=O)c2cc(-c4cnn(C)c4)ccc2O3)cc(OCC)c1-c1ccc(C(=O)[O-])cc1 ; [Na+]]

In the same manner as in Example 14, the intended compound was obtained as a colorless solid using methyl 2',6'-diethoxy-4'-{[6-(1-methyl-1H-pyrazol-4-yl)-4-oxospiro[chroman-2,4'-piperidin]-1'-yl]carbonyl}biphenyl-4-carboxylate.

$^1$H-NMR (DMSO-D$_6$) δ: 8.10 (1.0H, s), 7.80-7.78 (2.0H, m), 7.77-7.73 (3.0H, m), 7.10 (2.0H, d, J=8.2 Hz), 7.06 (1.0H, d, J=8.6 Hz), 6.65 (2.0H, s), 4.26-4.15 (1.0H, br m), 3.92 (4.0H, q, J=7.0 Hz), 3.80 (3.0H, s), 3.61-3.10 (3.0H, m), 2.84 (2.0H, s), 2.07-1.83 (2.0H, m), 1.80-1.68 (2.0H, m), 1.10 (6.0H, t, J=7.0 Hz).

MS[M+Na]+=632.4

EXAMPLE 19

Sodium 4'-({6-(5-carbamoylpyridin-2-yl)-4-oxospiro[chroman-2,4'-piperidin]-1'-yl}carbonyl)-2',6'-diethoxybiphenyl-3-carboxylate

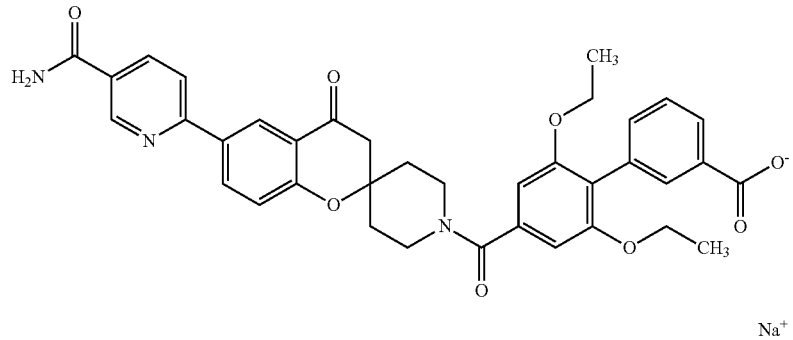 [SMILES: CCOc1cc(C(=O)N2CCC3(CC2)CC(=O)c2cc(-c4ccc(C(N)=O)cn4)ccc2O3)cc(OCC)c1-c1cccc(C(=O)[O-])c1 ; [Na+]]

In the same manner as in Example 14, the intended compound was obtained as a colorless solid using methyl 4'-({6-(5-carbamoylpyridin-2-yl)-4-oxospiro[chroman-2,4'-piperidin]-1'-yl}carbonyl)-2',6'-diethoxybiphenyl-3-carboxylate.

$^1$H-NMR (DMSO-D$_6$) δ: 9.04 (1.0H, d, J=2.3 Hz), 8.48 (1.0H, d, J=2.3 Hz), 8.35 (1.0H, dd, J=8.6, 2.3 Hz), 8.24 (1.0H, dd, J=8.2, 2.3 Hz), 8.16 (1.0H, s), 8.03 (1.0H, d, J=8.2 Hz), 7.73-7.69 (2.0H, m), 7.55 (1.0H, s), 7.21-7.16 (1.0H, m), 7.21 (1.0H, d, J=8.6 Hz), 7.13-7.10 (1.0H, m), 6.67 (2.0H, s), 4.32-4.15 (1.0H, br m), 3.93 (4.0H, q, J=7.0 Hz), 3.65-3.12 (3.0H, br m), 2.92 (2.0H, s), 2.09-1.88 (2.0H, m), 1.85-1.73 (2.0H, m), 1.08 (6.0H, t, J=7.0 Hz).

MS[M+Na]+=672.5

EXAMPLE 20

Sodium 2',6'-diethoxy-4'-{[6-(1-methyl-1H-pyrazol-4-yl)-4-oxospiro[chroman-2,4'-piperidin]-1'-yl]carbonyl}biphenyl-3-carboxylate

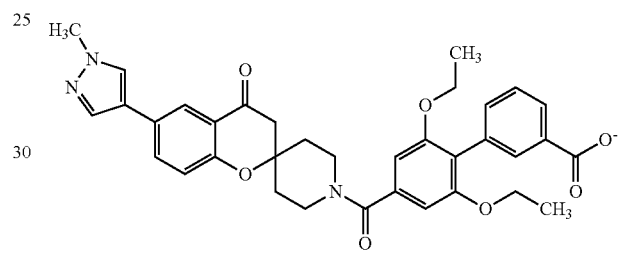

In the same manner as in Example 14, the intended compound was obtained as a colorless solid using methyl 2',6'-diethoxy-4'-{[6-(1-methyl-1H-pyrazol-4-yl)-4-oxospiro[chroman-2,4'-piperidin]-1'-yl]carbonyl}biphenyl-3-carboxylate.

$^1$H-NMR (DMSO-D$_6$) δ: 8.10 (1.0H, s), 7.80-7.78 (2.0H, m), 7.75 (1.0H, dd, J=8.6, 2.3 Hz), 7.73-7.68 (2.0H, m), 7.18 (1.0H, dd, J=7.4, 7.8 Hz), 7.13-7.09 (1.0H, m), 7.06 (1.0H, d, J=8.6 Hz), 6.66 (2.0H, s), 4.31-4.14 (1.0H, br m), 3.92 (4.0H, q, J=7.0 Hz), 3.80 (3.0H, s), 3.60-3.09 (3.0H, m), 2.84 (2.0H, s), 2.06-1.84 (2.0H, m), 1.80-1.68 (2.0H, m), 1.08 (6.0H, t, J=7.0 Hz).

MS[M+H]+=632.4

EXAMPLE 21

5-(2,6-Diethoxy-4-{[6-(1-methyl-1H-pyrazol-4-yl)-4-oxospiro[chroman-2,4'-piperidin]-1'-yl]carbonyl}phenyl)nicotinic acid

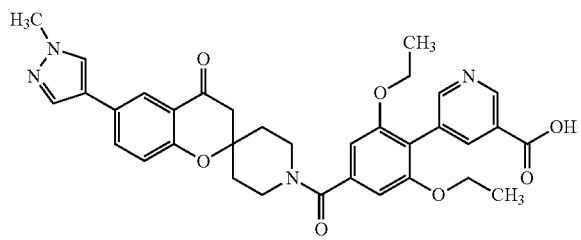 [SMILES: CCOc1cc(C(=O)N2CCC3(CC2)CC(=O)c2cc(-c4cnn(C)c4)ccc2O3)cc(OCC)c1-c1cncc(C(=O)O)c1]

TFA was added to a stirred solution of tert-butyl 5-(2,6-diethoxy-4-4-{[6-(1-methyl-1H-pyrazol-4-yl)-4-oxospiro[chroman-2,4'-piperidin]-1'-yl]carbonyl}phenyl)nicotinate (123 mg, 0.184 mmol) in CHCl$_3$ (1 ml) at room temperature overnight. The solvents were removed in reduced pressure and the residue was diluted with CHCl$_3$—saturated aqueous NaHCO$_3$. The aqueous layer was extracted with CHCl$_3$ and the combined organic layer was washed with brine, dried over MgSO$_4$. After MgSO$_4$ was filtered, the solvent was removed in vacuo and the resulted residue was purified by preparative TLC (CHCl$_3$/MeOH) to give the intended compound (72.1 mg, 0.118 mmol, 64.0% yield) as a colorless foam.

$^1$H-NMR (DMSO-D6) δ: 8.94 (1.0H, s), 8.68 (1.0H, s), 8.17 (1.0H, s), 8.14 (1.0H, s), 7.84 (1.0H, d, J=2.4 Hz), 7.82 (1.0H, d, J=0.7 Hz), 7.79 (1.0H, dd, J=8.5, 2.4 Hz), 7.10 (1.0H, d, J=8.5 Hz), 6.76 (2.0H, s), 4.39-4.19 (1.0H, br m), 4.03 (4.0H, q, J=6.8 Hz), 3.84 (3.0H, s), 3.61-3.13 (3.0H, m), 2.88 (2.0H, s), 2.09-1.88 (2.0H, m), 1.85-1.73 (2.0H, m), 1.16 (6.0H, t, J=6.8 Hz).

MS [M+H]+=611.5

EXAMPLE 22

Sodium 2',6'-diethoxy-3-fluoro-4'-{[6-(1-methyl-1H-pyrazol-4-yl)-4-oxospiro[chroman-2,4'-piperidin]-1'-yl]carbonyl}biphenyl-4-carboxylate

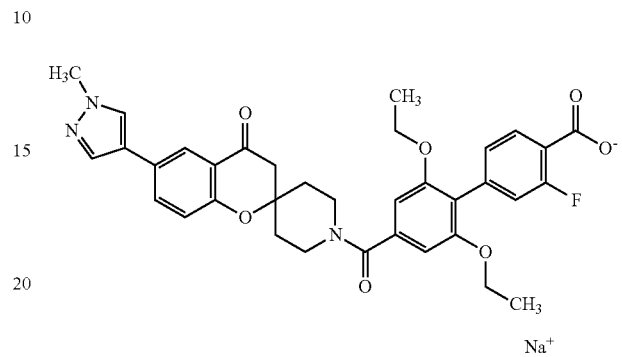

In the same manner as in Example 14, the intended compound was obtained as a colorless solid using methyl 2',6'-diethoxy-3-fluoro-4'-{[6-(1-methyl-1H-pyrazol-4-yl)-4-oxospiro[chroman-2,4'-piperidin]-1'-yl]carbonyl}biphenyl-4-carboxylate.

$^1$H-NMR (DMSO-D$_6$) δ: 8.14 (1.0H, s), 7.87-7.76 (3.0H, m), 7.43 (1.0H, t, J=7.8 Hz), 7.10 (1.0H, d, J=8.5 Hz), 6.93 (1.0H, dd, J=7.8, 1.2 Hz), 6.86 (1.0H, dd, J=11.5, 1.2 Hz), 6.69 (2.0H, s), 4.37-4.10 (1.0H, br m), 3.98 (4.0H, q, J=6.8 Hz), 3.84 (3.0H, s), 3.64-3.10 (3.0H, br m), 2.88 (2.0H, s), 2.10-1.86 (2.0H, br m), 1.84-1.70 (2.0H, br m), 1.16 (6.0H, t, J=6.8 Hz).

MS[M+Na]+=650.2

EXAMPLE 23

Sodium 5-[4-({6-(3-carbamoylphenyl)-4-oxospiro[chroman-2,4'-piperidin]-1'-yl}carbonyl)-2,6-diethoxyphenyl]nicotinate

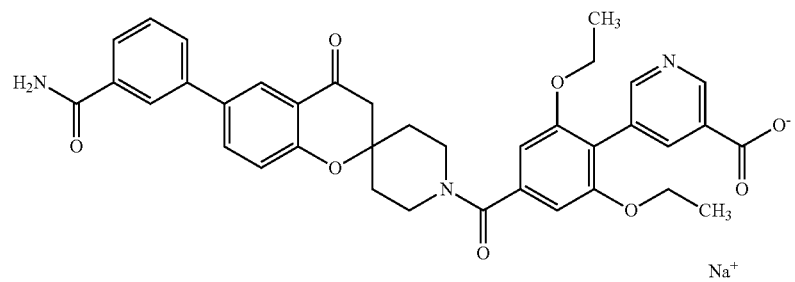 [SMILES: CCOc1cc(C(=O)N2CCC3(CC2)CC(=O)c2cc(-c4cccc(C(N)=O)c4)ccc2O3)cc(OCC)c1-c1cncc(C(=O)[O-])c1 ; [Na+]]

To a stirred solution of methyl 5-[4-({6-(3-carbamoylphenyl)-4-oxospiro[chroman-2,4'-piperidin]-1'-yl}carbonyl)-2,6-diethoxyphenyl]nicotinate (190 mg, 0.269 mmol) in CHCl₃ (2 ml) was added TFA (2 ml) and stirred at room temperature for overnight. The mixture was concentrated in vacuo, the residue was diluted with H₂O and aqueous 1N NaOH and purified by ODS column chromatography (H₂O/MeOH) to give intended compound (115 mg, 63.6% yield) as a pale yellow solid.

¹H-NMR (DMSO-D₆) δ: 8.80 (1H, d, J=2.0 Hz), 8.30 (1H, d, J=2.0 Hz), 8.16-8.08 (2H, m, 8.02-7.92 (3H, m), 7.80 (1H, d, J=7.8 Hz), 7.75 (1H, d, J=7.8 Hz), 7.48 (1H, dd, J=7.8, 7.8 Hz), 7.39 (1H, s), 7.18 (1H, d, J=8.6 Hz), 6.70 (2H, s), 4.31-4.17 (1H, br m), 3.96 (4H, q, J=7.0 Hz), 3.61-3.12 (3H, br m), 2.89 (2H, s), 2.08-1.86 (2H, m), 1.84-1.70 (2H, m), 1.09 (6H, t, J =7.0 Hz).

MS[M+Na]+=672.2

EXAMPLE 24

Sodium 2',6'-diethoxy-4-fluoro-4'-{[6-(1-methyl-1H-pyrazol-4-yl)-4-oxospiro[chroman-2,4'-piperidin]-1'-yl]carbonyl}biphenyl-3-carboxylate

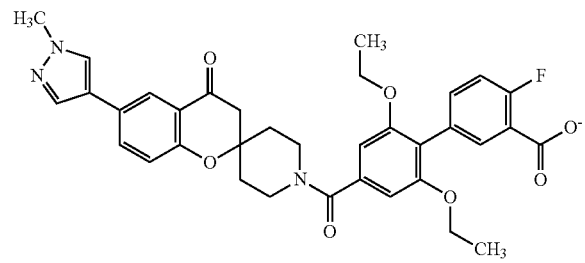

In the same manner as in Example 14, the intended compound was obtained as a colorless solid using methyl 2',6'-diethoxy-4-fluoro-4'-{[6-(1-methyl-1H-pyrazol-4-yl)-4-oxospiro[chroman-2,4'-piperidin]-1'-yl]carbonyl}biphenyl-3-carboxylate.

¹H-NMR (DMSO-D₆) δ: 8.14 (1.0H, s), 7.83 (1.0H, d, J=2.4 Hz), 7.82 (1.0H, s), 7.79 (1.0H, dd, J=8.3, 2.4 Hz), 7.37 (1.0H, dd, J=7.3, 2.4 Hz), 7.10 (1.0H, d, J=8.3 Hz), 7.07-7.01 (1.0H, m), 6.92 (1.0H, dd, J=10.2, 8.3 Hz), 6.68 (2.0H, s), 4.30-4.18 (1.0H, br m), 3.97 (4.0H, q, J=6.8 Hz), 3.84 (3.0H, s), 3.63-3.13 (3.0H, br m), 2.88 (2.0H, s), 2.09-1.85 (2.0H, br m), 1.83-1.72 (2.0H, br m), 1.14 (6.0H, t, J=6.8 Hz).

MS[M+Na]+=650.2

EXAMPLE 25

Methyl 4'-({6-(5-carbamoylpyridin-2-yl)-4-oxospiro[chroman-2,4'-piperidin]-1'-yl}carbonyl)-2',6'-diethoxybiphenyl-4-carboxylate

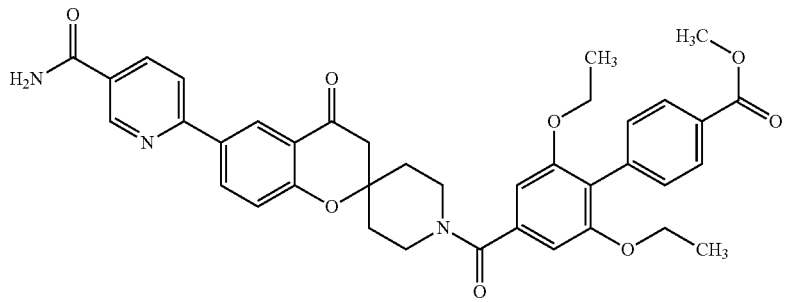 [SMILES: CCOc1cc(C(=O)N2CCC3(CC2)CC(=O)c2cc(-c4ccc(C(N)=O)cn4)ccc2O3)cc(OCC)c1-c1ccc(C(=O)OC)cc1]

TEA (0.657 ml, 4.71 mmol) was added to a stirred mixture of HOBT (313 mg, 2.04 mmol), WSCDI (361 mg, 1.89 mmol), 6-(4-oxospiro[chroman-2,4'-piperidin]-6-yl)nicotinamide dihydrochloride (2.61 g, 6.97 mmol) and 2,6-diethoxy-4'-(methoxycarbonyl)biphenyl-4-carboxylic acid (2.00 g, 5.81 mmol) in DMF (30 ml) and the mixture was stirred at room temperature for 3 days. The reaction mixture was poured into water (600 ml) and stirred for 30 min. The resulted precipitate was filtered, washed with water and the solid was dried in vacuo at 70° C. The crude product was purified by silicagel column chromatography (CHCl₃/Acetone) to give intended compound (3.85 g, quantitative) as a colorless solid.

¹H-NMR (CDCl₃) δ: 9.02 (1H, d, J=2.3 Hz), 8.48 (1H, d, J=2.3 Hz), 8.33 (1H, dd, J=8.6, 2.3 Hz), 8.18 (1H, dd, J=8.2, 2.3 Hz), 8.03-7.99 (2H, m), 7.82 (1H, d, J=8.6 Hz), 7.40-7.37 (2H, m), 7.14 (1H, d, J=8.6 Hz), 6.61 (2H, s), 6.23-5.94 (1H, m), 5.85-5.48 (1H, m), 4.57-4.43 (1H, br m), 3.94 (4H, q, J=7.0 Hz), 3.89 (3H, s), 3.80-3.24 (3H, m), 2.80 (2H, s), 2.29-1.98 (2H, m), 1.85-1.47 (2H, m), 1.20 (6H, t, J=7.0 Hz).

MS[M+H]+=664.5

EXAMPLE 26

Methyl 2',6'-diethoxy-4'-{[6-(1-methyl-1H-pyrazol-4-yl)-4-oxospiro[chroman-2,4'-piperidin]-1'-yl]carbonyl}biphenyl-4-carboxylate

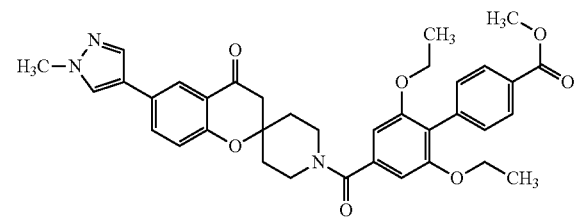 [SMILES: CCOc1cc(C(=O)N2CCC3(CC2)CC(=O)c2cc(-c4cnn(C)c4)ccc2O3)cc(OCC)c1-c1ccc(C(=O)OC)cc1]

In the same manner as in Example 25, the intended compound was obtained as a colorless solid using 6-(1-methyl- 1H-pyrazol-4-yl)spiro[chroman-2,4'-piperidin]-4-one hydrochloride and 2,6-diethoxy-4'-(methoxycarbonyl)biphenyl-4-carboxylic acid.

$^1$H-NMR (CDCl$_3$) δ: 8.00 (2H, d, J=8.2 Hz), 7.91 (1H, d, J=2.3 Hz), 7.69 (1H, s), 7.60 (1H, dd, J=8.6, 2.3 Hz), 7.57 (1H, s), 7.38 (2H, d, J=8.2 Hz), 6.99 (1H, d, J=8.6 Hz), 6.60 (2H, s), 4.60-4.39 (1H, m), 3.94 (4H, t, J=6.8 Hz), 3.91 (3H, s), 3.89 (3H, s), 3.77-3.21 (3H, m), 2.75 (2H, s), 2.26-1.99 (2H, m), 1.81-1.51 (2H, m), 1.20 (6H, t, J=6.8 Hz).

MS[M+H]+=624.5

EXAMPLE 27

Sodium 4'-({6-(5-carbamoylpyridin-2-yl)-4-oxospiro[chroman-2,4'-piperidin]-1'-yl}carbonyl)-2',6'-diethoxybiphenyl-4-carboxylate

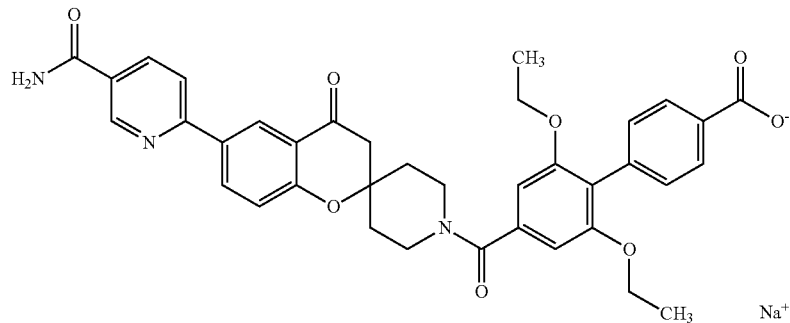 [SMILES: CCOc1cc(C(=O)N2CCC3(CC2)CC(=O)c2cc(-c4ccc(C(N)=O)cn4)ccc2O3)cc(OCC)c1-c1ccc(C(=O)[O-])cc1 ; [Na+]]

Aqueous 1N NaOH (11.6 ml, 11.6 mmol) was added to a stirred solution of methyl 4'-({6-(5-carbamoylpyridin-2-yl)-4-oxospiro[chroman-2,4'-piperidin]-1'-yl}carbonyl)-2',6'-diethoxybiphenyl-4-carboxylate (3.85 g, 5.80 mmol) in THF (40 ml)-MeOH (40 ml) and the mixture was stirred at room temperature for 12 days. After water was added to the mixture, the organic solvents were evaporated under reduced pressure. The aqueous residue was purified by ODS column chromatography eluting with H$_2$O/MeOH and the residue was crystallized from MeOH to give intended compound as a pale red solid. The solid was diluted in H$_2$O and aqueous 1N NaOH, and was purified by ODS column chromatography eluting with H$_2$O/MeOH, and the residue was crystallized from MeOH to give intended compound (2.04 g, 3.04 mmol, 52.4% yield) as a pale red crystal.

$^1$H-NMR (DMSO-D$_6$) δ: 9.04 (1H, d, J=2.3 Hz), 8.48 (1H, d, J=2.3 Hz), 8.35 (1H, dd, J=8.8, 2.3 Hz), 8.24 (1H, dd, J=8.2, 2.3 Hz), 8.17 (1H, s), 8.03 (1H, d, J=8.2 Hz), 7.76 (2H, d, J=8.0 Hz), 7.55 (1H, s), 7.20 (1H, d, J=8.8 Hz), 7.11 (2H, d, J=8.0 Hz), 6.66 (2H, s), 4.31-4.17 (1H, br m), 3.92 (4H, q, J=6.8 Hz), 3.62-3.13 (3H, br m), 2.91 (2H, s), 2.08-1.86 (2H, br m), 1.84-1.71 (2H, br m), 1.10 (6H, t, J=6.8 Hz).

MS[M+Na]+=672.2

EXAMPLE 28-1

Methyl 4-(8-cyclopropyl-2-{[6-(1-methyl-1H-pyrazol-4-yl)-4-oxospiro[chroman-2,4'-piperidin]-1'-yl]carbonyl}quinolin-4-yl)benzoate

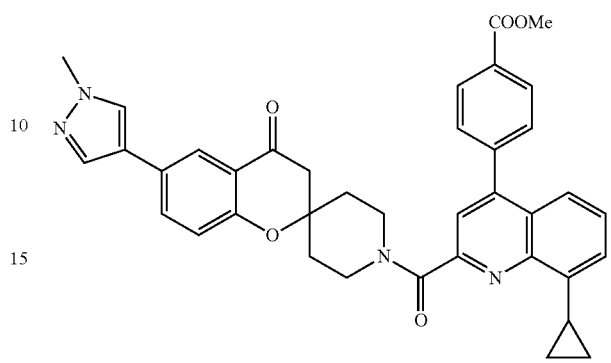

K$_3$PO$_4$ (109 mg, 0.515 mmol) was added to a stirred mixture of TBAB (8.30 mg, 0.0260 mmol), PdCl$_2$(dppf) (18.9 mg, 0.0260 mmol), 8-cyclopropyl-2-{[6-(1-methyl-1H-pyrazol-4-yl)-4-oxospiro[chroman-2,4'-piperidin]-1'-yl]carbonyl}quinolin-4-yl trifluoromethanesulfonate (165 mg, 0.258 mmol) and [4-(methoxycarbonyl)phenyl]boronic acid (55.6 mg, 0.309 mmol) in MeCN (2 ml) and the mixture was stirred at 90° C. overnight. The mixture was filtered, washing with CHCl$_3$ and the solvent was evaporated under reduced pressure. The residue was purified by silicagel column chromatography (hexane/EtOAc) to give intended compound as a yellow solid.

EXAMPLE 28-2

Methyl 4-(3-methyl-6-{[6-(1-methyl-1H-pyrazol-4-yl)-4-oxospiro[chroman-2,4'-piperidin]-1'-yl]carbonyl}-1H-indazol-1-yl)benzoate

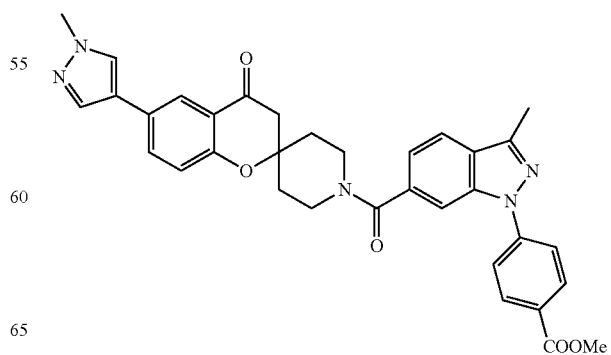

Pyridine (0.080 ml, 0.988 mmol) was added to a stirred mixture of 1'-[(3-methyl-1H-indazol-6-yl)carbonyl]-6-(1-methyl-1H-pyrazol-4-yl)spiro[chroman-2,4'-piperidin]-4-one (150 mg, 0.329 mmol), [4-(methoxycarbonyl)phenyl]boronic acid (119 mg, 0.659 mmol), Cu(OAc)$_2$ (90 mg, 0.494 mmol) in CH$_2$Cl$_2$ (1.5 ml) and the mixture was stirred at room temperature overnight. The mixture was filtered and the solvent was evaporated under reduced pressure. The residue was purified by silicagel column chromatography (hexane/EtOAc) to give intended compound as colorless oil.

EXAMPLE 28-3

Methyl 3-(3-methyl-6-{[6-1-methyl-1H-pyrazol-4-yl)-4-oxospiro[chroman-2,4'-piperidin]-1'-yl]carbonyl}-1H-indazol-1-yl)benzoate

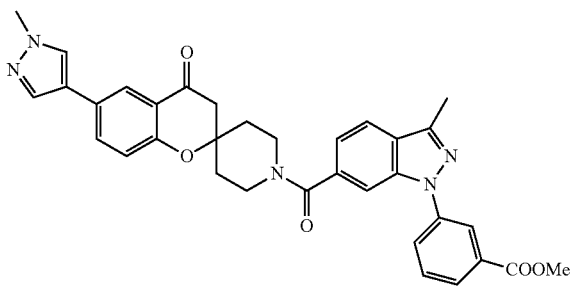 [SMILES: COC(=O)c1cccc(-n2nc(C)c3ccc(C(=O)N4CCC5(CC4)CC(=O)c4cc(-c6cnn(C)c6)ccc4O5)cc32)c1]

The intended compound was produced according to the procedure described in Example 28-2 but using [3-(methoxycarbonyl)phenyl]boronic acid in place of [4-(methoxycarbonyl)phenyl]boronic acid.

EXAMPLE 28-4

Methyl 4-(1-cyclopropyl-3-methyl-6-{[6-(1-methyl-1H-pyrazol-4-yl)-4-oxospiro[chroman-2,4'-piperidin]-1'-yl]carbonyl}-1H-indol-4-yl)benzoate

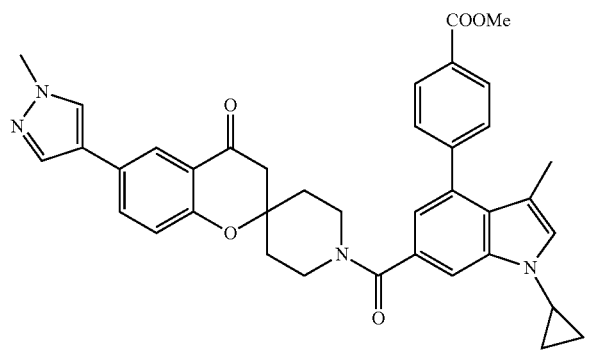 [SMILES: COC(=O)c1ccc(-c2cc(C(=O)N3CCC4(CC3)CC(=O)c3cc(-c5cnn(C)c5)ccc3O4)cc3c2c(C)cn3C2CC2)cc1]

The intended compound was produced according to the procedure described in Reference Example 3-1, 3-2 and Example 28-1 but using 1-cyclopropyl-4-[4-(methoxycarbonyl)phenyl]-3-methyl-1H-indole-6-carboxylic acid in place of 2,6-diethoxy-3'-(methoxycarbonyl)biphenyl-4-carboxylic acid.

EXAMPLE 28-5

Methyl 1-(1-cyclopropyl-6-{[6-(1-methyl-1H-pyrazol-4-yl)-4-oxospiro[chroman-2,4'-piperidin]-1'-yl]carbonyl}-1H-indol-4-yl)piperidine-4-carboxylate

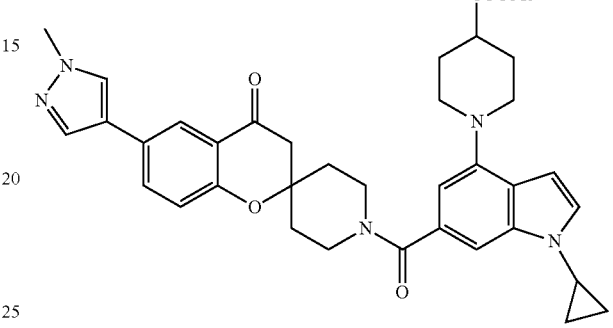

Cs$_2$CO$_3$ (261 mg, 0.800 mmol), Pd(OAc)$_2$ (8.98 mg, 0.040 mmol), 1-cyclopropyl-6-{[6-(1-methyl-1H-pyrazol-4-yl)-4-oxospiro[chroman-2,4'-piperidin]-1'-yl]carbonyl}-1H-indol-4-yl trifluoromethanesulfonate (251 mg, 0.4 mmol), ethyl 4-piperidinecarboxylate (94.0 mg, 0.600 mmol) and biphenyl-2-yl(di-tert-butyl)phosphine (11.9 mg, 0.0400 mmol) were suspended in 1,4-dioxane (3 ml) and the mixture was stirred at 100° C. overnight. The mixture was filtered through celite pad, washing with CHCl$_3$, and the solvent was evaporated under reduced pressure. The residue was purified by silicagel column chromatography (CHCl$_3$/MeOH), then preparative-TLC (CHCl$_3$/MeOH) to give intended compound as brown oil.

EXAMPLE 28-6

Methyl 4-(1-cyclopropyl-6-{[6-(1-methyl-1H-pyrazol-4-yl)-4-oxospiro[chroman-2,4'-piperidin]-1'-yl]carbonyl}-1H-indol-4-yl)benzoate

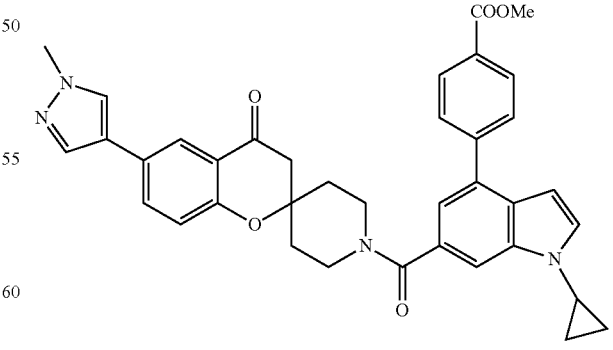

The intended compound was produced according to the procedure described in Example 28-1 but using 1-cyclopropyl-6-{[6-(1-methyl-1H-pyrazol-4-yl)-4-oxospiro[chroman-2,4'-piperidin]-1'-yl]carbonyl}-1H-indol-4-yltrifluoromethanesulfonate in place of 8-cyclopropyl-2-{[6-(1-methyl-1H-pyrazol-4-yl)-4-oxospiro[chroman-2,4'-piperidin]-1'-yl]carbonyl}quinolin-4-yl trifluoromethanesulfonate.

EXAMPLE 28-7

Methyl 3-(1-cyclopropyl-6-{[6-(1-methyl-1H-pyrazol-4-yl)-4-oxospiro[chroman-2,4'-piperidin]-1'-yl]carbonyl}-1H-indol-4-yl)benzoate

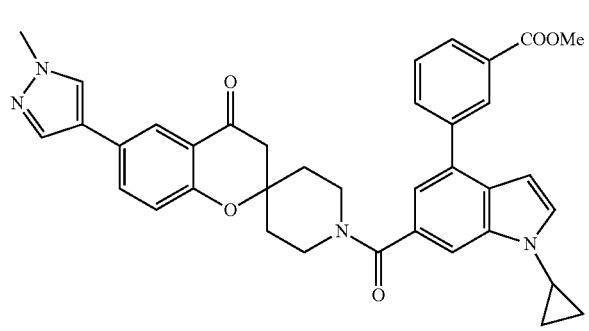 [SMILES: COC(=O)c1cccc(-c2cc(C(=O)N3CCC4(CC3)CC(=O)c3cc(-c5cnn(C)c5)ccc3O4)cc3c2ccn3C2CC2)c1]

The intended compound was produced according to the procedure described in Example 28-1 but using 1-cyclopropyl-6-{[6-(1-methyl-1H-pyrazol-4-yl)-4-oxospiro[chroman-2,4'-piperidin]-1'-yl]carbonyl}-1H-indol-4-yl trifluoromethanesulfonate and [3-(methoxycarbonyl)phenyl]boronic acid in place of 8-cyclopropyl-2-{[6-(1-methyl-1H-pyrazol-4-yl)-4-oxospiro[chroman-2,4'-piperidin]-1'-yl]carbonyl}quinolin-4-yl trifluoromethanesulfonate and [4-(methoxycarbonyl)phenyl]boronic acid.

EXAMPLE 28-8

Methyl 2-(1-cyclopropyl-6-{[6-(1-methyl-1H-pyrazol-4-yl)-4-oxospiro[chroman-2,4'-piperidin]-1'-yl]carbonyl}-1H-indol-4-yl)benzoate

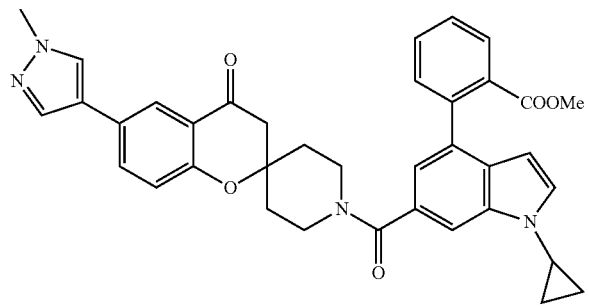 [SMILES: COC(=O)c1ccccc1-c1cc(C(=O)N2CCC3(CC2)CC(=O)c2cc(-c4cnn(C)c4)ccc2O3)cc2c1ccn2C1CC1]

The intended compound was produced according to the procedure described in Example 28-1 but using 1-cyclopropyl-6-{[6-(1-methyl-1H-pyrazol-4-yl)-4-oxospiro[chroman-2,4'-piperidin]-1'-yl]carbonyl}-1H-indol-4-yl trifluoromethanesulfonate and [2-(methoxycarbonyl)phenyl]boronic acid in place of 8-cyclopropyl-2-{[6-(1-methyl-1H-pyrazol-4-yl)-4-oxospiro[chroman-2,4'-piperidin]-1'-yl]carbonyl}quinolin-4-yl trifluoromethanesulfonate and [4-(methoxycarbonyl)phenyl]boronic acid.

EXAMPLE 28-9

Methyl [(1-cyclopropyl-6-{[6-(1-methyl-1H-pyrazol-4-yl)-4-oxospiro[chroman-2,4'-piperidin]-1'-yl]carbonyl}-1H-indol-4-yl)oxy]acetate

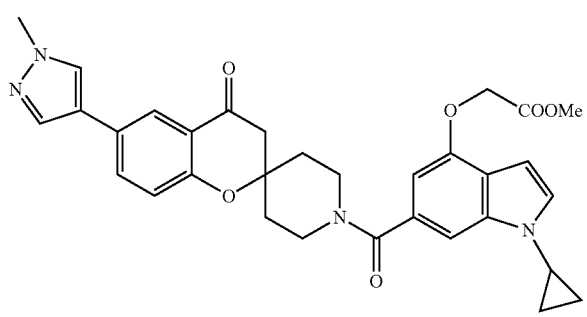 [SMILES: COC(=O)COc1cc(C(=O)N2CCC3(CC2)CC(=O)c2cc(-c4cnn(C)c4)ccc2O3)cc2c1ccn2C1CC1]

Methyl bromoacetate (0.059 ml, 0.604 mmol) was added to a stirred mixture of $K_2CO_3$ (111 mg, 0.806 mmol), 1'-[(1-cyclopropyl-4-hydroxy-1H-indol-6-yl)carbonyl]-6-(1-methyl-1H-pyrazol-4-yl)spiro[chroman-2,4'-piperidin]-4-one (200 mg, 0.403 mmol) in DMF (2 ml) and the mixture was stirred at room temperature overnight. The mixture was diluted with EtOAc, washed with water, brine, and dried over $MgSO_4$. After filteration and evaporation, the residue was purified by silicagel column chromatography ($CHCl_3$/MeOH) to give intended compound as yellow oil.

EXAMPLE 28-10

Methyl 4-(3-methyl-5-{[6-(1-methyl-1H-pyrazol-4-yl)-4-oxospiro[chroman-2,4'-piperidin]-1'-yl]carbonyl}-1H-indazol-1-yl)benzoate

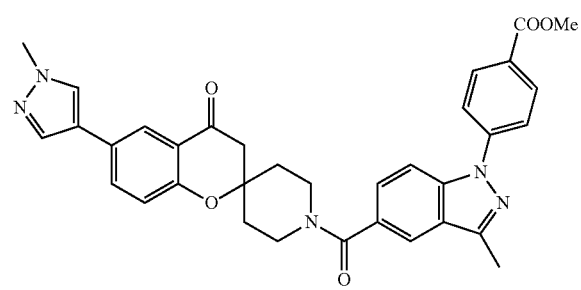 [SMILES: COC(=O)c1ccc(-n2nc(C)c3cc(C(=O)N4CCC5(CC4)CC(=O)c4cc(-c6cnn(C)c6)ccc4O5)ccc32)cc1]

The intended compound was produced according to the procedure described in Example 28-2 but using 1'-[(3-methyl-1H-indazol-5-yl)carbonyl]-6-(1-methyl-1H-pyrazol-4-yl)spiro[chroman-2,4'-piperidin]-4-one in place of 1'-[(3-methyl-1H-indazol-6-yl)carbonyl]-6-(1-methyl-1H-pyrazol-4-yl)spiro[chroman-2,4'-piperidin]-4-one.

EXAMPLE 28-11

Methyl 3-(3-methyl-5-{[6-(1-methyl-1H-pyrazol-4-yl)-4-oxospiro[chroman-2,4'-piperidin]-1'yl]carbonyl}-1H-indazol-1-yl)benzoate

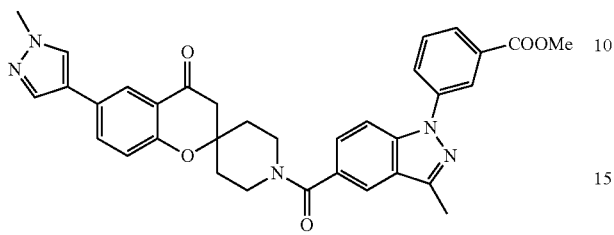

The intended compound was produced according to the procedure described in Example 28-2 but using 1'-[(3-methyl-1H-indazol-5-yl)carbonyl]-6-(1-methyl-1H-pyrazol-4-yl)spiro[chroman-2,4'-piperidin]-4-one and [3-(methoxycarbonyl)phenyl]boronic acid in place of 1'-[(3-methyl-1H-indazol-6-yl)carbonyl]-6-(1-methyl-1H-pyrazol-4-yl)spiro[chroman-2,4'-piperidin]-4-one and [4-(methoxycarbonyl)phenyl]boronic acid.

EXAMPLE 28-12 tert-Butyl 5-(2,6-diethoxy-4-{[6-(1-methyl-1H-pyrazol-4-yl)-4-oxospiro[chroman-2,4'-piperidin]-1'-yl]carbonyl}phenyl)nicotinate

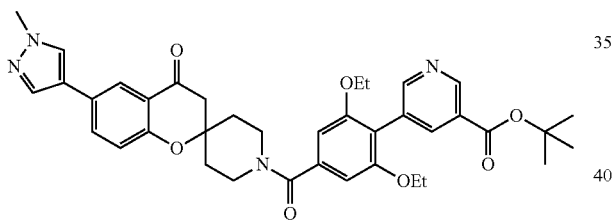

The intended compound was produced according to the procedure described in Reference Example 3-1 but using 4-[5-(tert-butoxycarbonyl)pyridin-3-yl]-3,5-diethoxybenzoic acid in place of 8-cyclopropyl-4-hydroxyquinoline-2-carboxylic acid.

EXAMPLE 28-13

Methyl 2',6'-diethoxy-3-fluoro-4'-{[6-(1-methyl-1H-pyrazol-4-yl)-4-oxospiro[chroman-2,4'-piperidin]-1'-yl]carbonyl}biphenyl-4-carboxylate

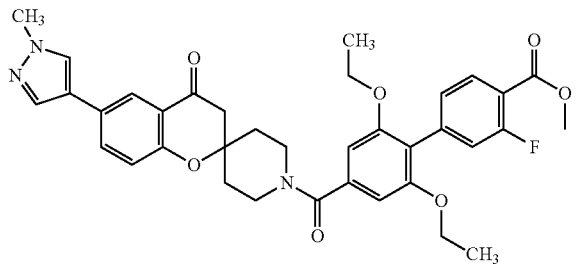 [SMILES: CCOc1cc(C(=O)N2CCC3(CC2)CC(=O)c2cc(-c4cnn(C)c4)ccc2O3)cc(OCC)c1-c1ccc(C(=O)OC)c(F)c1]

In the same manner as in Reference Example 3-1, the intended compound was obtained as a colorless solid using 6-(1-methyl-1H-pyrazol-4-yl)spiro[chroman-2,4'-piperidin]-4-one hydrochloride and 2,6-diethoxy-3'-fluoro-4'-(methoxycarbonyl)biphenyl-4-carboxylic acid.

EXAMPLE 28-14

Methyl 2',6'-diethoxy-4-fluoro-4'-{[6-(1-methyl-1H-pyrazol-4-yl)-4-oxospiro[chroman-2,4'-piperidin]-1'-yl]carbonyl}biphenyl-3-carboxylate

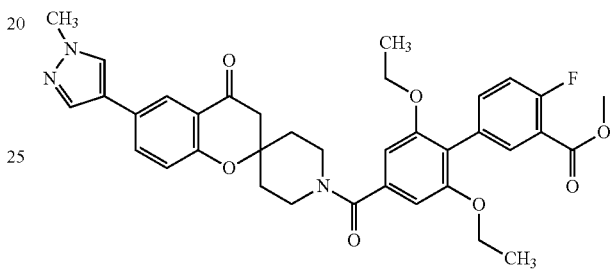

In the same manner as in Reference Example 3-1, the intended compound was obtained as a colorless solid using 6-(1-methyl-1H-pyrazol-4-yl)spiro[chroman-2,4'-piperidin]-4-one hydrochloride and 2,6-diethoxy-4'-fluoro-3'-(methoxycarbonyl)biphenyl-4-carboxylic acid.

REFERENCE EXAMPLE 1-1 tert-Butyl 6-bromo-4-oxospiro[chroman-2,4'-piperidine]-1'-carboxylate

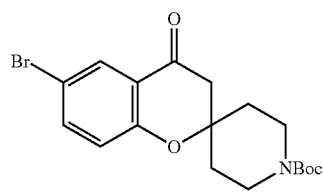 [SMILES: CC(C)(C)OC(=O)N1CCC2(CC1)CC(=O)c1cc(Br)ccc1O2]

A mixture of 5-bromo-2-hydroxyacetophenone (104 g, 485 mmol), N-Boc-piperidin-4-one (98.6 g, 494 mmol), 20 mL of pyrrolidine (17.3 g, 243 mmol) and 261 mL of MeOH was heated under reflux until the reaction was complete. The mixture was cooled, then 87 mL of H₂O were added, and the mixture was filtered and dried to give intended compound as a colorless solid.

REFERENCE EXAMPLE 1-2

1'-tert-Butoxycarbonyl-6-(4,4,5,5-tetramethyl-1,3,2-dioxaborolan-2-yl)spiro[chroman-2,4'-piperidin]-4-one

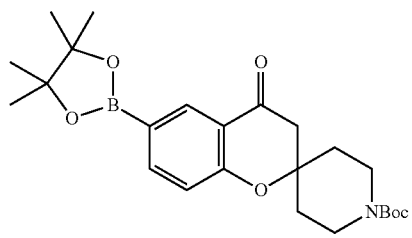 [SMILES: CC(C)(C)OC(=O)N1CCC2(CC1)CC(=O)c1cc(B3OC(C)(C)C(C)(C)O3)ccc1O2]

tert-Butyl 6-bromo-4-oxospiro[chroman-2,4'-piperidine]-1'-carboxylate (99.0 g, 250 mmol), bis(pinacolato)diboran (70.2 g, 275 mmol), Pd(OAc)$_2$ (2.80 g, 12.5 mmol), DPPF (13.9 g, 25.0 mmol), and KOAc (29.1 g, 300 mmol) were suspended in dioxane (500 ml) and heated at 100° C. for 20 h. After cooling down to room temperature, MeOH (500 ml) was added and further stirred for 1 h. The resulted precipitate was filtered and the cake was washed with MeOH to obtain the intended compound as a pale brown solid.

REFERENCE EXAMPLE 1-3

5-{1'-tert-Butoxycarbonyl-4-oxospiro[chroman-2,4'-piperidin]-6-yl}nicotinamide

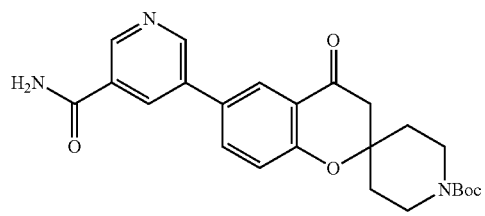 [SMILES: CC(C)(C)OC(=O)N1CCC2(CC1)CC(=O)c1cc(-c3cncc(C(N)=O)c3)ccc1O2]

1'-tert-butoxycarbonyl-6-(4,4,5,5-tetramethyl-1,3,2-dioxaborolan-2-yl)spiro[chroman-2,4'-piperidin]-4-one (1.43 g, 3.23 mmol), 5-bromonicotinamide (778 mg, 3.87 mmol), Pd(PPh$_3$)$_4$ (372 mg, 0.322 mmol), and aqueous 2M Na$_2$CO$_3$ (10 ml) solution were suspended in dioxane (20 ml) and heated at 100° C. for 4 h. The reaction mixture was diluted with CHCl$_3$ and H$_2$O, the aqueous layer was extracted with CHCl$_3$. The combined organic layer was dried over MgSO$_4$. The desiccant was removed through celite filtration and the filtrate was concentrated under reduced pressure. The resulting residue was purified through silica gel column chromatography (EtOAc/Acetone) to obtain the intended compound as a pale yellow foam.

REFERENCE EXAMPLE 1-4

5-{4-Oxospiro[chroman-2,4'-piperidin]-6-yl}nicotinamide dihydrochloride

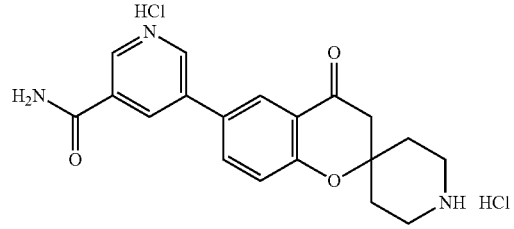 [SMILES: Cl ; NC(=O)c1cncc(-c2ccc3c(c2)C(=O)CC2(CCNCC2)O3)c1 ; Cl]

5-{1'-tert-butoxycarbonyl-4-oxospiro[chroman-2,4'-piperidin]-6-yl}nicotinamide (1.30 g) was suspended in dioxane (10 ml) and 4N HCl in dioxane (20 ml) was added thereto, and stirred at room temperature for 18 h. The resulted precipitate was filtered, washed with dioxane and Et$_2$O to obtain the intended compound as a colorless solid.

REFERENCE EXAMPLE 1-5

6-(4-Oxospiro[chroman-2,4'-piperidin]-6-yl)nicotinamide dihydrochloride

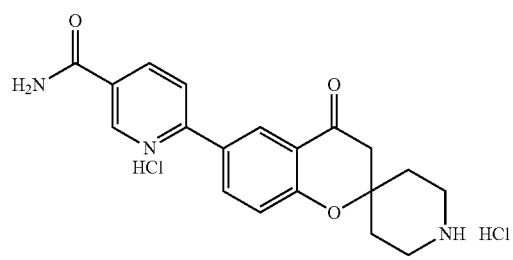 [SMILES: NC(=O)c1ccc(-c2ccc3c(c2)C(=O)CC2(CCNCC2)O3)nc1 ; Cl ; Cl]

The intended compound was produced according to the procedure described in Reference Example 1-3 and 1-4 but using 6-chloronicotinamide in place of 5-bromonicotinamide.

REFERENCE EXAMPLE 1-6 tert-Butyl 6-(1-Methyl-1H-pyrazol-4-yl)-4-oxospiro[chroman-2,4'-piperidine]-1'-carboxylate

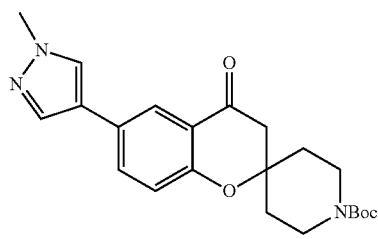 [SMILES: Cn1cc(-c2ccc3c(c2)C(=O)CC2(CCN(C(=O)OC(C)(C)C)CC2)O3)cn1]

tert-Butyl 6-bromo-4-oxospiro[chroman-2,4'-piperidine]-1'-carboxylate (1 g) and 1-methyl-4-(4,4,5,5-tetramethyl-1,3, 2-dioxaborolan-2-yl)-1H-pyrazole (682 mg) were dissolved in dioxane in a nitrogen atmosphere, and aqueous 2M Na$_2$CO$_3$ (10 ml) solution (3.8 mL) and tetrakis(triphenylphosphine)palladium (144 mg) were added thereto, and degassed. The reaction liquid was stirred overnight at 100° C., cooled to room temperature, then water was added thereto, and filtered through Celite. The filtrate was extracted with chloroform, and the organic layer was dried with sodium sulfate. Sodium sulfate was removed through filtration, the filtrate was concentrated under reduced pressure, and the residue was purified through silica gel column chromatography (hexane/EtOAc) to obtain the intended compound as a pale yellow solid.

REFERENCE EXAMPLE 1-7

6-(1-Methyl-1H-pyrazol-4-yl)spiro[chroman-2,4'-piperidin]-4-one hydrochloride

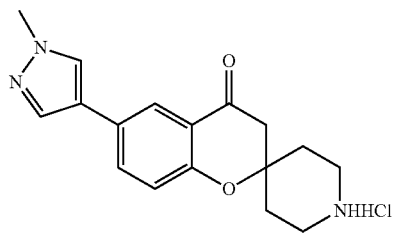

4 N hydrogen chloride/dioxane solution was added to tert-butyl 6-(1-methyl-1H-pyrazol-4-yl)-4-oxospiro[chroman-2,4'-piperidine]-1'-carboxylate (1.00 g), and stirred overnight at room temperature. Ether was added to the reaction liquid, the resulted precipitate was taken out through filtration, washed with ether, and dried under reduced pressure to obtain the intended compound as a colorless solid.

REFERENCE EXAMPLE 1-8

3-(4-Oxospiro[chroman-2,4'-piperidin]-6-yl)benzamide hydrochloride

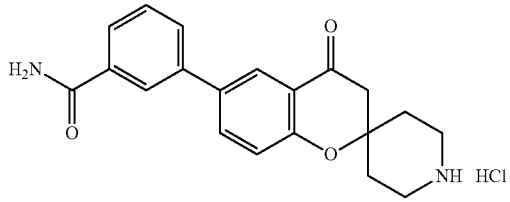 [SMILES: NC(=O)c1cccc(-c2ccc3c(c2)C(=O)CC2(CCNCC2)O3)c1 ; Cl]

The intended compound was produced according to the procedure described in Reference Example 1-6 and 1-7 but using [3-(aminocarbonyl)phenyl]boronic acid in place of 1-methyl-4-(4,4,5,5-tetramethyl-1,3,2-dioxaborolan-2-yl)-1H-pyrazole.

REFERENCE EXAMPLE 1-9

4-(4-Oxospiro[chroman-2,4'-piperidin]-6-yl)benzamide hydrochloride

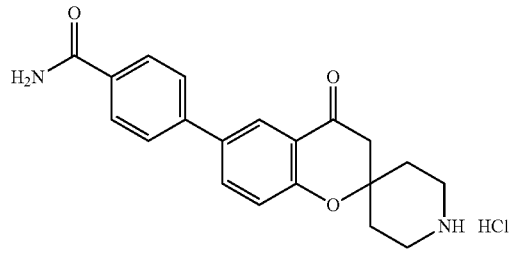 [SMILES: NC(=O)c1ccc(-c2ccc3c(c2)C(=O)CC2(CCNCC2)O3)cc1 ; Cl]

The intended compound was produced according to the procedure described in Reference Example 1-6 and 1-7 but using [4-(aminocarbonyl)phenyl]boronic acid in place of 1-methyl-4-(4,4,5,5-tetramethyl-1,3,2-dioxaborolan-2-yl)-1H-pyrazole.

REFERENCE EXAMPLE 1-10

6-(1H-pyrazol-5-yl)spiro[chroman-2,4'-piperidin]-4-one hydrochloride

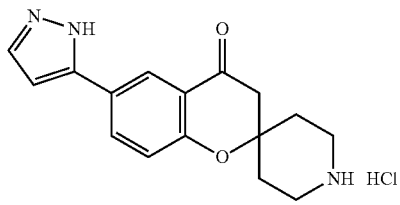 [SMILES: O=C1CC2(CCNCC2)Oc2ccc(-c3ccn[nH]3)cc21 ; Cl]

The intended compound was produced according to the procedure described in Reference Example 1-6 and 1-7 but using 1-[(2-trimethylsilylethoxy)methyl]-1H-pyrazole-5-boronic acid in place of 1-methyl-4-(4,4,5,5-tetramethyl-1,3,2-dioxaborolan-2-yl)-1H-pyrazole.

REFERENCE EXAMPLE 1-11 tert-Butyl 6-(5-carbamoylpyridin-2-yl)-4-oxospiro[chroman-2,4'-piperidine]-1'-carboxylate

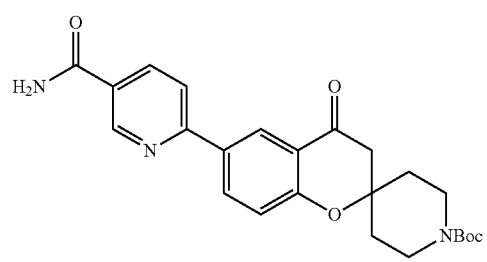 [SMILES: CC(C)(C)OC(=O)N1CCC2(CC1)CC(=O)c1cc(-c3ccc(C(N)=O)cn3)ccc1O2]

1'-tert-butoxycarbonyl-6-(4,4,5,5-tetramethyl-1,3,2-dioxaborolan-2-yl)spiro[chroman-2,4'-piperidin]-4-one (40.0 g, 90.0 mmol), 6-chloronicotinamide (17.0 g, 108 mmol), Pd(PPh₃)₄ (5.21 g, 4.51 mmol), and aqueous 2M Na₂CO₃ (100 ml) solution were suspended in dioxane (300 ml) and heated at 100° C. for 16 h. The reaction mixture was diluted with CHCl₃ and H₂O, the aqueous layer was extracted with CHCl₃. The combined organic layer was washed with brine, dried over MgSO₄ and silicagel. The desiccant was removed through celite filtration and the filtrate was concentrated under reduced pressure. The resulting residue was purified by crystallization (CHCl₃-EtOAc) to obtain the intended compound as a colorless solid.

REFERENCE EXAMPLE 1-12

6-(4-Oxospiro[chroman-2,4'-piperidin]-6-yl)nicotinamide dihydrochloride

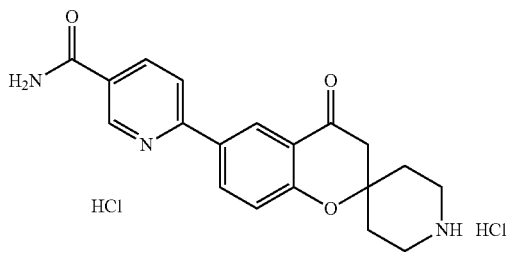 [SMILES: NC(=O)c1ccc(-c2ccc3c(c2)C(=O)CC2(CCNCC2)O3)nc1 ; Cl ; Cl]

To a suspension of tert-butyl 6-(5-carbamoylpyridin-2-yl)-4-oxospiro[chroman-2,4'-piperidine]-1'-carboxylate in dioxane (125 ml) was added 4N HCl in dioxane (125 ml) and the mixture was stirred for 18 h. After Et₂O was added to the mixture, the resulted precipitate was collected by aeration, washed with Et₂O to give intended compound as a colorless solid.

REFERENCE EXAMPLE 2-1

4-Bromo-3,5-diethoxybenzoic acid

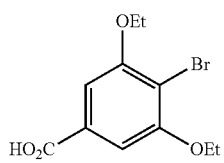

To a stirred solution of methyl 4-bromo-3,5-diethoxybenzoate (3.00 g) in a mixture of THF (25 ml) and MeOH (10 ml) was added aqueous 1N NaOH (20 ml) and the reaction mixture was stirred at room temperature for 6 h. The mixture was concentrated under reduced pressure and the residue was diluted with H₂O and diethylether. The aqueous layer was acidified with aqueous 1N HCl, the mixture was extracted with CHCl₃ and dried over sodium sulfate. After filtration and concentration, the residue was dried in vacuo to give the crude intended compound as a colorless solid. Thus obtained crude product was used in the next step without further purification.

REFERENCE EXAMPLE 2-2 tert-Butyl 4-bromo-3,5-diethoxybenzoate

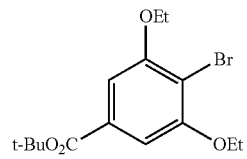

To a mixture of 4-Bromo-3,5-diethoxybenzoic acid (2.8 g) in DMF (25 ml) was added CDI (1.8 g) at room temperature and the mixture was stirred at 40° C. for 2 h. To the reaction mixture, t-BuOH (1.85 ml) and DBU (1.75 ml) were added and further stirred at 40° C. overnight. After cooling to room temperature, the mixture was poured into ice-H₂O and extracted with EtOAc. The organic layer was washed with H₂O, brine and dried over sodium sulfate. After filtration and concentration, the residue was purified by silica gel column chromatography (hexane/EtOAc) to give the intended compound as a colorless solid.

REFERENCE EXAMPLE 2-3

4-tert-Butyl 4'-methyl 2,6-diethoxybiphenyl-4,4'-dicarboxylate

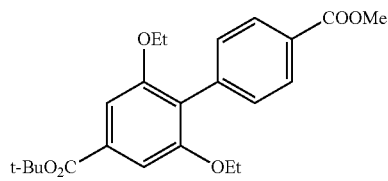

H₂O (261 mg, 14.48 mmol) was added to a stirred mixture of PdCl₂(dppf) (106 mg, 0.145 mmol), [4-(methoxycarbonyl)phenyl]boronic acid (626 mg, 3.48 mmol), tert-butyl 4-bromo-3,5-diethoxybenzoate (1.00 g, 2.90 mmol) and K₃PO₄ (1.23 g, 5.79 mmol) in DME (8 ml) and the mixture was stirred at 100° C. overnight. The reaction mixture was filtered through celite pad, the filtrate was concentrated under reduced pressure. The residue was purified by silicage column chromatography (hexane/EtOAc) to give intended compound as a colorless solid.

REFERENCE EXAMPLE 2-4

2,6-Diethoxy-4'-(methoxycarbonyl)biphenyl-4-carboxylic acid

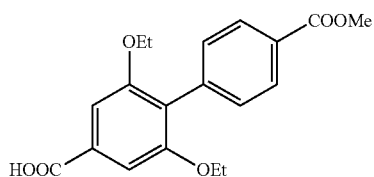 [SMILES: CCOc1cc(C(=O)O)cc(OCC)c1-c1ccc(C(=O)OC)cc1]

TFA (4 ml) was added to a stirred solution of 4-tert-butyl 4'-methyl 2,6-diethoxybiphenyl-4,4'-dicarboxylate (850 mg, 2.12 mmol) in CHCl₃ (2 ml) and the reaction mixture was stirred at room temperature overnight. After the solvents were removed under reduced pressure, CHCl₃ and MeOH were added to the residue. The solvents were removed under reduced pressure again, and the residue was dried in vacuo to give the crude intended compound as a colorless solid. Thus obtained crude product was used in the next step without further purification.

REFERENCE EXAMPLE 2-5

2,6-Diethoxy-3'-(methoxycarbonyl)biphenyl-4-carboxylic acid

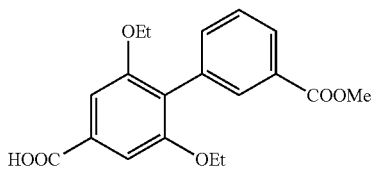 [SMILES: CCOc1cc(C(=O)O)cc(OCC)c1-c1cccc(C(=O)OC)c1]

The intended compound was produced according to the procedure described in Reference Example 2-3 and 2-4 but using [3-(methoxycarbonyl)phenyl]boronic acid in place of [4-(methoxycarbonyl)phenyl]boronic acid.

REFERENCE EXAMPLE 2-6

[5-(tert-Butoxycarbonyl)pyridin-3-yl]boronic acid

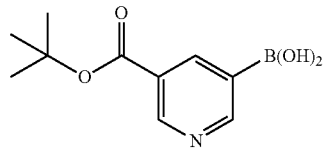 [SMILES: CC(C)(C)OC(=O)c1cncc(B(O)O)c1]

Pd(OAc)₂ (0.112 g, 0.500 mmol), DPPF (0.554 g, 1.000 mmol), KOAc (1.18 g, 12.0 mmol), tert-butyl 5-bromonicotinate (2.58 g, 10.0 mmol) and bis(pinacolato)diboran (2.79 g, 11.0 mmol) were suspended in 1,4-dioxane (25 ml) and the mixture was stirred at 100° C. overnight. The mixture was filtered through celite pad, and the filtrate was evaporated in vacuo. The residue was suspended in acetone (25.0 ml)/H₂O (25.0 ml), and sodium periodate (6.41 g, 30.0 mmol) and ammonium acetate (2.31 g, 30.0 mmol) were added thereto. The mixture was stirred at room temperature for overnight and was diluted with CHCl₃ and H₂O. The organic layer was washed with H₂O, brine, and dried over MgSO₄. After filteration and evaporation, the residue was purified by silicagel colunm chromatography (CHCl₃/MeOH) to give intended compound as a brown solid.

REFERENCE EXAMPLE 2-7 tert-Butyl 5-[2,6-diethoxy-4-(methoxycarbonyl)phenyl]nicotinate

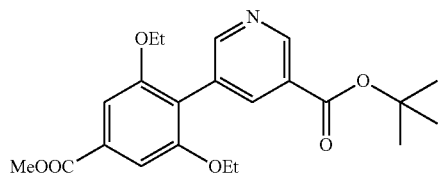 [SMILES: CCOc1cc(C(=O)OC)cc(OCC)c1-c1cncc(C(=O)OC(C)(C)C)c1]

H₂O (59.4 mg, 3.30 mmol) was added to a stirred suspension of PdCl₂(dppf) (12.1 mg, 0.0330 mmol), methyl 4-bromo-3,5-diethoxybenzoate (200 mg, 0.660 mmol), [5-(tert-butoxycarbonyl)pyridin-3-yl]boronic acid (177 mg, 0.792 mmol) and K₃PO₄ (420 mg, 1.98 mmol) in DME (4 ml) and the mixture was stirred at 90° C. overnight. The reaction mixture was filtered through celite pad, the filtrate was concentrated under reduced pressure. The residue was purified by silicagel column chromatography (hexane/EtOAc) to give intended compounds as a colorless solid.

REFERENCE EXAMPLE 2-8

4-[5-(tert-Butoxycarbonyl)pyridin-3-yl]-3,5-diethoxybenzoic acid

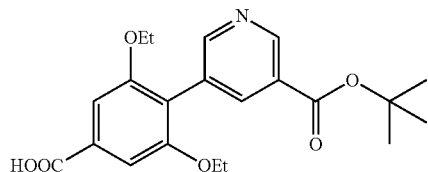 [SMILES: CCOc1cc(C(=O)O)cc(OCC)c1-c1cncc(C(=O)OC(C)(C)C)c1]

The intended compound was produced according to the procedure described in Reference Example 2-1 but using tert-butyl 5-[2,6-diethoxy-4-(methoxycarbonyl)phenyl]nicotinate in place of methyl 4-bromo-3,5-diethoxybenzoate.

REFERENCE EXAMPLE 2-9

1-Acetyl-5-bromo-3-methyl-1H-indazole

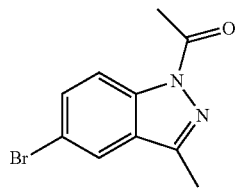

Acetic anhydride (4.73 ml) was added to the mixture of 4-bromo-2-ethylaniline (5.0 g) and KOAc (2.94 g) in CHCl₃ (70 ml) and stirred for 30 minutes at reflux. Then isoamyl nitrite (6.65 ml) and 18-crown-6-ether (660 mg) was added to the reaction mixture and stirred for 12 h. under reflux. The reaction mixture was diluted with CHCl₃, washed with water, and dried over sodium sulfate. After filtration and concentration, the residue was purified by silica gel chromatography (hexane/EtOAc), and crystallized from mixed solvent of hexane and CHCl₃ to give intended compound as a yellow solid.

REFERENCE EXAMPLE 2-10

Methyl 3-methyl-1H-indazole-5-carboxylate

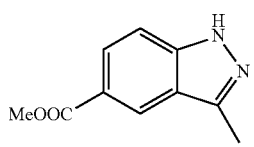

N,N-diisopropylethylamine (4.14 ml, 23.71 mmol) was added to a stirred mixture of 1-acetyl-5-bromo-3-methyl-1H-indazole (2.00 g, 7.90 mmol), DPPF (0.657 g, 1.185 mmol) and Pd(OAc)₂ (0.266 g, 1.185 mmol) in DMF (20 ml)-MeOH (5 ml) at room temperature and the mixture was stirred in CO atmospher (1 atm) at 90° C. overnight. After the mixture was cooled and the CO gas was removed by N₂ gas, the mixture was filtered through celite pad and the filtrate was evaporated under reduced pressure. The residue was purified by silicagel column chromatography (hexane/EtOAc) to give intended compound as a pale brown solid.

REFERENCE EXAMPLE 2-11

3-Methyl-1H-indazole-5-carboxylic acid

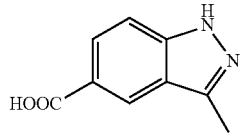

Aqueous 5N NaOH (4 ml, 20.00 mmol) was added to a stirred solution of methyl 3-methyl-1H-indazole-5-carboxylate (1.02 g, 5.36 mmol) in MeOH (10 ml) and the mixture was stirred at 70° C. for 6 h. The mixture was cooled, and the solvent was evaporated under reduced pressure. The mixture was diluted with H₂O, and aqueous 5N HCl (4 ml) was added to the mixture with stirring, the resulted precipitate was filtered and dried over at 50° C. overnight to give intended compound as a brown solid.

REFERENCE EXAMPLE 2-12

Methyl 3-methyl-1H-indazole-6-carboxylate

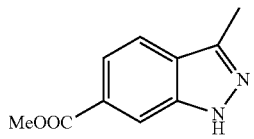

Ac₂O (0.579 ml, 6.14 mmol) was added to a stirred mixture of KOAc (361 mg, 3.68 mmol) and methyl 3-amino-4-ethyl-benzoate (550mg, 3.07 mmol) in CHCl₃ (5 ml) and the mixture was stirred at 90° C. for 2 h. KOAc (361 mg, 3.68 mmol), 18-crown-6 ether (81 mg, 0.307 mmol) and isobutylnitrate (719 mg, 6.14 mmol) were added thereto at room temperature and the mixture was further stirred at 90° C. for 2 h. The reaction mixtuer was diluted with chloroform and H₂O, the organic layer was washed with water, brine, and dried over MgSO₄. After filteration and evaporation, the residue was diluted with THF (5.00 ml) and MeOH (5.00 ml), and K₂CO₃ (848 mg, 6.14 mmol) was added thereto at room temperature. After the mixture was stirred for 2 h. at room temperature, CHCl₃ and H₂O was added thereto. The organic layer was washed with H₂O, brine, and dried over MgSO₄. After filteration and evaporation, the reside was puritied by silicagel column chromatography (hexane/EtOAc) to give intended compound as a pale brown solid.

REFERENCE EXAMPLE 2-13

3-Methyl-1H-indazole-6-carboxylic acid

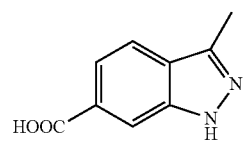

The intended compound was produced according to the procedure described in Reference Example 2-11 but using methyl 3-methyl-1H-indazole-6-carboxylate in place of methyl 3-methyl-1H-indazole-5-carboxylate.

REFERENCE EXAMPLE 2-14

1-Cyclopropyl-1H-pyrrole-2-carbaldehyde

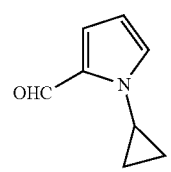

POCl₃ (44.5 ml) was added to a stirred solution of 1-cyclopropyl-1H-pyrrole (46.5 g) in DMF (37 ml) at 0° C., then the mixture was stirred at room temperature overnight. The mixture was poured into aqueous 5N NaOH (336 ml) at 0° C., and the mixture was made basic with an additional aqueous 5N NaOH. The mixture was extracted with CH₂Cl₂ and the organic extract was dried over Na₂SO₄, concentrated, and the residue was purified on silicagel column chromatography (hexane/EtOAc) to give intended compound as colorless oil.

REFERENCE EXAMPLE 2-15

Ethyl 4-acetoxy-1-cyclopropyl-1H-indole-6-carboxylate

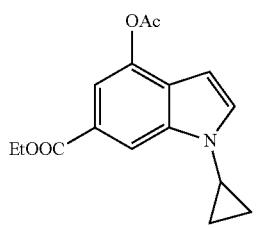 [SMILES: CCOC(=O)c1cc(OC(C)=O)c2ccn(C3CC3)c2c1]

Na (14.6 g) was added portion wise to EtOH (400 ml) with stirring at room temperature. To the mixture was added a solution of 1-cyclopropyl-1H-pyrrole-2-carbaldehyde (38.9 g) and diethyl succinate (48.2 ml) in EtOH (100 ml) at 50° C., then the mixture was refluxed overnight. 140 ml of aqueous 5N HCl was added to the mixture at 0° C. and EtOH was evaporated. The residue was extracted with $CHCl_3$, the organic layer was dried over $Na_2SO_4$ and concentrated to give red oil. The material was dissolved in 400 ml of acetic anhydride and KOAc (47.4 g) was added thereto. The mixture was refluxed for 30 min. and allowed to cool to room temperature. The mixture was filtrated and the filtrate was concentrated. The residue was purified by silicagel column chromatography (hexane/EtOAc) to give intended compound a red oil.

REFERENCE EXAMPLE 2-16

Ethyl 1-cyclopropyl-4-hydroxy-1H-indole-6-carboxylate

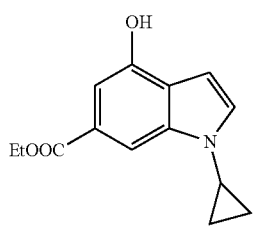 [SMILES: CCOC(=O)c1cc(O)c2ccn(C3CC3)c2c1]

$K_2CO_3$ (69.6 g) was added to a solution of ethyl 4-acetoxy-1-cyclopropyl-1H-indole-6-carboxylate (72.3 g) in EtOH (360 ml) placed in a 2 L flask and the mixture was stirred at room temperature for 4 h. EtOH was evaporated and the redisue was diluted with EtOAc. The mixture was washed with water and brine, dried over $Na_2SO_4$. After filteration and concentration, the residue was triturated with toluene and hexane to give intended compound as a pale tan solid.

REFERENCE EXAMPLE 2-17

1-Cyclopropyl-4-hydroxy-1H-indole-6-carboxylic acid

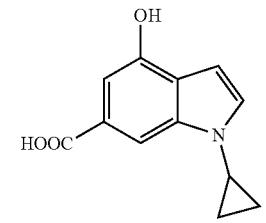

The intended compound was produced according to the procedure described in Reference Example 2-11 but using ethyl 1-cyclopropyl-4-hydroxy-1H-indole-6-carboxylate in place of methyl 3-methyl-1H-indazole-5-carboxylate.

REFERENCE EXAMPLE 2-18

8-Cyclopropyl-4-hydroxyquinoline-2-carboxylic acid

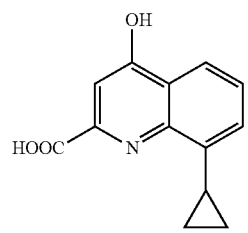 [SMILES: O=C(O)c1cc(O)c2cccc(C3CC3)c2n1]

The intended compound was produced according to the procedure described in Reference Example 2-11 but using methyl 8-cyclopropyl-4-hydroxyquinoline-2-carboxylate in place of methyl 3-methyl-1H-indazole-5-carboxylate.

REFERENCE EXAMPLE 2-19

2,6-Diethoxy-3'-fluoro-4'-(methoxycarbonyl)biphenyl-4-carboxylic acid

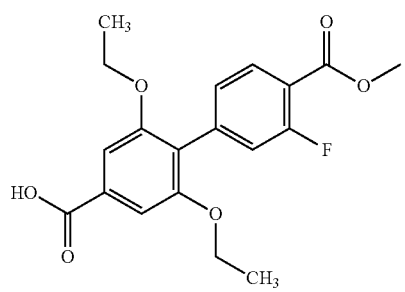 [SMILES: CCOc1cc(C(=O)O)cc(OCC)c1-c1ccc(C(=O)OC)c(F)c1]

The intended compound was produced according to the procedure described in Reference Example 2-3 and 2-4 but using [3-fluoro-4-(methoxycarbonyl)phenyl]boronic acid in place of [4-(methoxycarbonyl)phenyl]boronic acid.

REFERENCE EXAMPLE 2-20

2,6-Diethoxy-4'-fluoro-3'-(methoxycarbonyl)biphenyl-4-carboxylic acid

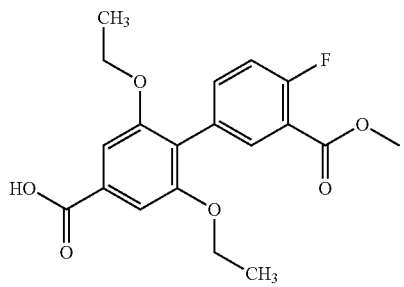 [SMILES: CCOc1cc(C(=O)O)cc(OCC)c1-c1ccc(F)c(C(=O)OC)c1]

The intended compound was produced according to the procedure described in Reference Example 2-3 and 2-4 but using [4-fluoro-3-(methoxycarbonyl)phenyl]boronic acid in place of [4-(methoxycarbonyl)phenyl]boronic acid.

REFERENCE EXAMPLE 3-1

1'-[(8-Cyclopropyl-4-hydroxyquinolin-2-yl)carbonyl]-6-(1-methyl-1H-pyrazol-4-yl)spiro[chroman-2,4'-piperidin]-4-one

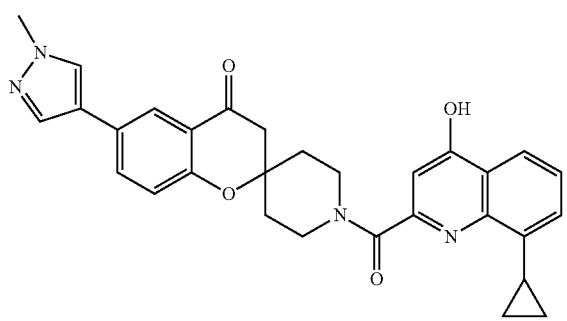 [SMILES: Cn1cc(-c2ccc3c(c2)C(=O)CC2(CCN(C(=O)c4cc(O)c5cccc(C6CC6)c5n4)CC2)O3)cn1]

TEA (0.657 ml, 4.71 mmol) was added to a stirred mixture of HOBT (313 mg, 2.04 mmol), WSCDI (361 mg, 1.89 mmol), 6-(1-methyl-1H-pyrazol-4-yl)spiro[chroman-2,4'-piperidin]-4-one hydrochloride (629 mg, 1.89 mmol) and 8-cyclopropyl-4-hydroxyquinoline-2-carboxylic acid (360 mg, 1.57 mmol) in DMF (3.5 ml) and the mixture was stirred at room temperature overnight. The reaction mixture was poured into water (20 ml) and stirred for 30 min. The resulted precipitate was filtered, washed with water and the solid was dried in vacuo at 70° C. The crude product was purified by silicagel column chromatography (CHCl$_3$/AcOEt) to give intended compound as a pale brown solid.

REFERENCE EXAMPLE 3-2

8-Cyclopropyl-2-{[6-(1-methyl-1H-pyrazol-4-yl)-4-oxospiro[chroman-2,4'-piperidin]-1'-yl]carbonyl}quinolin-4-yl trifluoromethanesulfonate

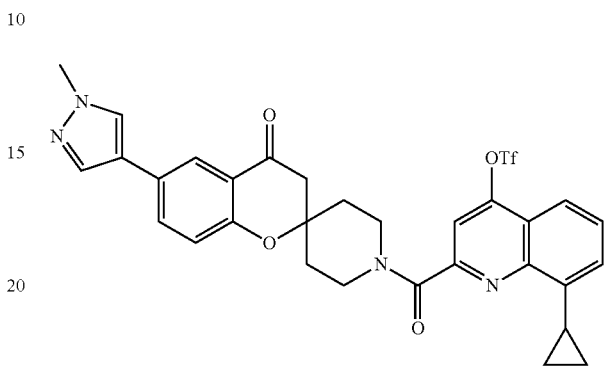

Tf$_2$O (0.224 ml, 1.327 mmol) was added to a stirred solution of pyridine (0.358 ml, 4.42 mmol) and 1'-[(8-cyclopropyl-4-hydroxyquinolin-2-yl)carbonyl]-6-(1-methyl-1H-pyrazol-4-yl)spiro[chroman-2,4'-piperidin]-4-one (450 mg, 0.885 mmol) in CHCl$_3$ (4.5 ml) at −50° C. and the mixture was stirred at room temperature for 3 h. The reaction mixture was diluted with CHCl$_3$ and H$_2$O, the organic layer was washed with brine and dried over MgSO$_4$. After filtration and concentration, the residue was purified by silicagel column chromatography (hexane/EtOAc) to give intended compound as a pale yellow solid.

REFERENCE EXAMPLE 3-3

1'-[(3-Methyl-1H-indazol-6-yl)carbonyl]-6-(1-methyl-1H-pyrazol-4-yl)spiro[chroman-2,4'-piperidin]-4-one

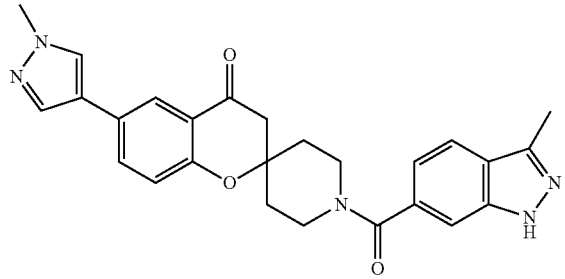 [SMILES: Cc1n[nH]c2cc(C(=O)N3CCC4(CC3)CC(=O)c3cc(-c5cnn(C)c5)ccc3O4)ccc12]

The intended compound was produced according to the procedure described in Reference Example 3-1 but using 3-methyl-1H-indazole-6-carboxylic acid in place of 8-cyclopropyl-4-hydroxyquinoline-2-carboxylic acid.

REFERENCE EXAMPLE 3-4

1'-[(1-Cyclopropyl-4-hydroxy-1H-indol-6-yl)carbonyl]-6-(1-methyl-1H-pyrazol-4-yl)spiro[chroman-2,4'-piperidin]-4-one

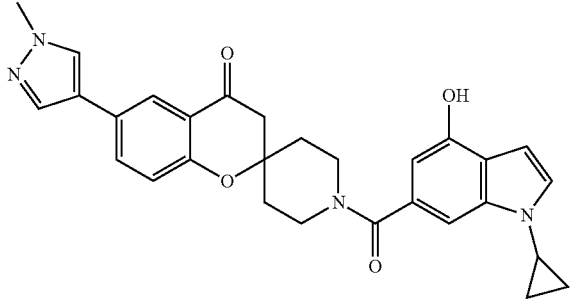

The intended compound was produced according to the procedure described in Reference Example 3-1 but using 1-cyclopropyl-4-hydroxy-1H-indole-6-carboxylic acid in place of 8-cyclopropyl-4-hydroxyquinoline-2-carboxylic acid.

REFERENCE EXAMPLE 3-5

1-Cyclopropyl-6-{[6-(1-methyl-1H-pyrazol-4-yl)-4-oxospiro[chroman-2,4'-piperidin]-1'-yl]carbonyl}-1H-indol-4-yl trifluoromethanesulfonate

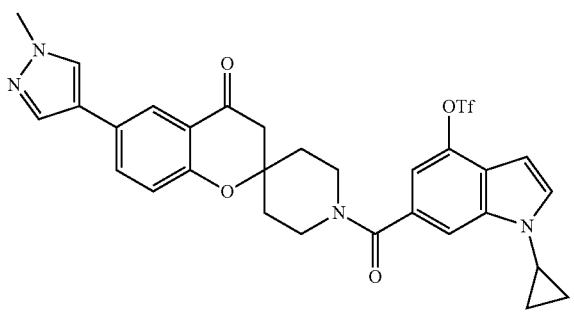 [SMILES: Cn1cc(-c2ccc3c(c2)C(=O)CC2(CCN(C(=O)c4cc(OS(=O)(=O)C(F)(F)F)c5ccn(C6CC6)c5c4)CC2)O3)cn1]

The intended compound was produced according to the procedure described in Reference Example 3-2 but using 1'-[(1-cyclopropyl-4-hydroxy-1H-indol-6-yl)carbonyl]-6-(1-methyl-1H-pyrazol-4-yl)spiro[chroman-2,4'-piperidin]-4-one in place of 1'-[(8-cyclopropyl-4-hydroxyquinolin-2-yl)carbonyl]-6-(1-methyl-1H-pyrazol-4-yl)spiro[chroman-2,4'-piperidin]-4-one.

REFERENCE EXAMPLE 3-6

1'-[(3-Methyl-1H-indazol-5-yl)carbonyl]-6-(1-methyl-1H-pyrazol-4-yl)spiro[chroman-2,4'-piperidin]-4-one

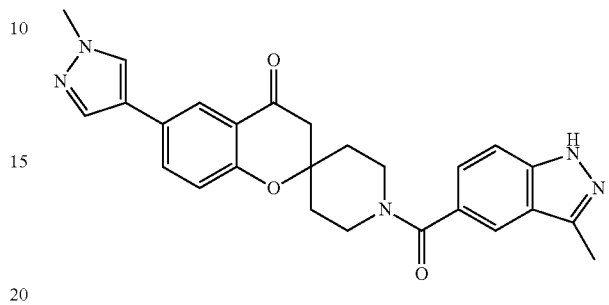

The intended compound was produced according to the procedure described in Reference Example 3-1 but using 3-methyl-1H-indazole-5-carboxylic acid in place of 8-cyclopropyl-4-hydroxyquinoline-2-carboxylic acid.

The usefulness of the compounds of the invention as medicines is demonstrated, for example, by the following pharmacological test example.

BIOLOGICAL ASSAYS

A. Pharmacological Test Example (Acetyl CoA Carboxylase (ACC) Activity Inhibition Test)

A test compound is dissolved in dimethyl sulfoxide (DMSO) to a concentration of 10 mM and then diluted with DMSO to give a 100-fold concentrated solution of the compound compared with target assay concentration. The ACC enzyme activity inhibition test is carried out according to a modification of Thampy & Wakil's method (*J. Biol. Chem.*, Vol. 260, pp. 6318-6323 (1985)). Concretely, 0.8 μl of the diluted test compound is added to each well of 96-well assay plate (Perkin Elmer Opti Plate), then 40 μl of a substrate solution (50 mM Hepes sodium (pH 7.5), 2 mM DTT, 10 mM ATP, 500 μM acetyl CoA, 0.17 mM NaH[$^{14}$C]O$_3$ (58 mCi/mmol by Amersham), 8 mM NaHCO$_3$) is added to each well, and 40 μL of an enzyme solution (1 to 2 nM human ACC1 or human ACC2, 50 mM Hepes sodium (pH 7.5), 2 mM DTT, 40 mM MgCl$_2$, 40 mM tripotassium citrate 1 mg/ml fetal bovine serum albumin) is added thereto. Then, the upper side of the plate is sealed up, and the plate is incubated with gently stirring at 37° C. for 40 minutes. Next, 20 μl of 1 N HCl is added to each well to stop the enzyme reaction, and the assay plate is stirred overnight to remove the unreacted NaH[$^{14}$C]O$_3$. Next, 100 μl of a scintillator (Perkin Elmer's Microscinti 40) is added to each well and the plate is stirred, then the radioactivity of the fixed [$^{14}$C] is counted using a microplate scintillation counter (Perkin Elmer's Topcount), the radioactivity of which represents the enzyme activity in each well. The human ACC1 and human ACC2 enzyme-inhibition activities of the test compounds are calculated, based on the radioactivity of the well added by DMSO without test compound as a control.

The compounds of the invention were tested according to this method and the compounds tested all inhibited both ACC1 and ACC2. The results are shown in the following Table.

| Inhibition (%) by 1 µmol/liter Chemical | | |
|---|---|---|
| Compound | human ACC1 | human ACC2 |
| Example 3 | 100% | 99% |
| Example 5 | 98% | 99% |
| Example 13 | 99% | 99% |
| Example 18 | 99% | 100% |
| Example 20 | 100% | 99% |
| Example 21 | 100% | 100% |

Representative compounds of the present invention, including the compounds of Examples 1-21 were tested in the above assay and found to have a percent inhibition of greater than or equal to 50% for ACC-1 and a percent inhibition of greater than or equal to 50% for ACC-2 in the acetyl CoA carboxylase (ACC) activity inhibition test.

B. Effect of ACC1/2 Inhibitor on in Vivo Body Weight, Fat Mass, Fatty Liver and Plasma Glucose Levels Effect of ACC1/2 inhibitor on body weight, fat mass, fatty liver and plasma glucose level can be determined in either high fat diet induced obese or KKAy diabetic mice.

Male C57black/6J mice at approximately 6 weeks old are individually housed and maintained on chow diet for 2 weeks prior to the study. Then the mice are fed with a 60% fat diet for 5 weeks before dosing. The mice (n=8) on the high fat diet are orally dosed with either vehicle control (0.5% methylcellulose solution) or an ACC1/2 inhibitor (various doses) for 6 weeks. Body weight is determined on a daily basis and fat mass is measured by NMR every other week. Hepatic triglyceride content is determined at week 6. Effective ACC1/2 inhibitors result reduced body weight gain, reduced fat mass gain, and reduced hepatic triglyceride content in ACC1/2 inhibitor treated male C57black/6J mice in contrast to the vehicle control group.

Male KKAy mice at approximately 8 weeks old are individually housed and maintained on for 2 weeks prior to the study. The mice (n=10) are orally dosed with either vehicle control (0.5% methylcellulose solution) or an ACC1/2 inhibitor (various doses) for 2 weeks. At week 2, blood is collected at 23 hours post dose and plasma glucose concentration is determined. Effective ACC1/2 inhibitors result in reduced plasma glucose levels in ACC1/2 inhibitor treated KKAy mice in contrast to the vehicle control group.

C. Human Study for Effect on Food Intake and Glucose/Insulin Levels 800 people with a BMI≧30 who have impaired fasting plasma glucose levels, impaired glucose tolerance, or elevated serum insulin, indicative of a prediabetic insulin resistant state, and who may have elevated serum glucose levels, indicative of type II diabetes, are advised to diet and increase their physical activity. After a two-week placebo run-in period, which includes a standardized program of diet, physical activity, and lifestyle changes, the patients are randomized into 2 treatment groups: placebo; and an effective dose of a compound of formula (I). The compound of formula (I) is given once or more per day, as previously determined to be effective. Patients are treated for 6 months, body weights are measured biweekly, and appetite, hunger, satiety are measured weekly using standard questionnaires. Serum glucose, insulin levels and body weight are determined at day 0, monthly, and after the final dose.

Effective compounds result in body weight loss or an improvement in serum insulin levels, indicative of improved insulin sensitivity or lower fasting blood glucose levels.

FORMULATION PREPARATION EXAMPLE 1

20.0 g of the compound of Example 1, 417 g of lactose, 80 g of crystalline cellulose and 80 g of partially-alphatized starch are mixed in a V-shape mixer, and 3.0 g of magnesium stearate is added to it and mixed. The mixture powder is tabletted according to an ordinary method to obtain 3000 tablets each having a diameter of 7.0 mm and a weight of 150 mg.

| Ingredients of Tablet (150 mg) | |
|---|---|
| Compound of Example 1 | 5.0 mg |
| Lactose | 104.25 mg |
| Crystalline cellulose | 20.0 mg |
| Partially-alphatized starch | 20.0 mg |
| Magnesium stearate | 0.75 mg |

FORMULATION PREPARATION EXAMPLE 2

10.8 g of hydroxypropyl cellulose 2910 and 2.1 g of polyethylene glycol 6000 are dissolved in 172.5 g of pure water, and 2.1 g of titanium oxide is dispersed therein to prepare a coating liquid. Using a high-coater-mini, 2500 tablets of Preparation Example 1 that is prepared separately is sprayed with the coating liquid to obtain film-coated tables each having a weight of 155 mg.

| Ingredients of Tablet (155 mg) | |
|---|---|
| Tablet of Preparation Example 1 | 150 mg |
| Hydroxypropyl cellulose 2910 | 3.6 mg |
| Polyethylene glycol 6000 | 0.7 mg |
| Titanium dioxide | 0.7 mg |

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated obesity, diabetes, obesity-related disorders, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and embodiments of the present invention. It is intended, therefore, that the invention be limited only by the scope of the claims which follow and that such claims be interpreted as broadly as is reasonable.

The invention claimed is:

1. A compound of general formula (I-1):

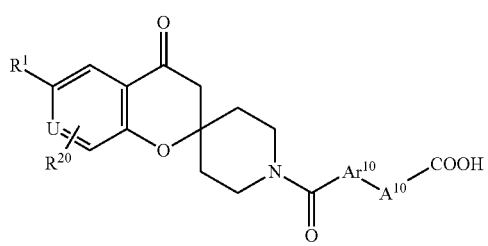

(I-1)

wherein A¹⁰ represents a linking group formed from a carbo- or heterocyclic ring selected from a group consisting of a benzene ring, a pyridine ring, a piperidine ring, in which said linking group optionally has substituent(s) selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a C2-C7 alkanoylamino group, a C1-C6 alkylcarbamoyl group, a cyclo-C3-C6 alkylcarbamoyl group, a (C1-C6 alkoxy-C1-C6 alkyl)carbamoyl group, a C2-C7 alkoxycarbonyl group, a C1-C6 alkylsulfonyl group, a C1-C6 alkylsulfonylamino group and a tetrazolyl group;

Ar¹⁰ represents a group formed from an aromatic ring selected from a group consisting of a benzene ring, optionally having substituent(s) selected from R³;

R²⁰ represents a hydrogen atom, a halogen atom, a C1-C6 alkyl group or a C1-C6 alkoxy group;

U is a methine group;

R¹ is a 3-pyridyl, 2-pyridyl, 5-pyrazoyl, 4-pyrazoyl, or phenyl group optionally having substituent(s) selected from a group consisting of and an amide group; and R3 represents a C1-C6 alkyl group, a cyclo-C3-C6 alkyl group, a phenyl group and a C1-C6 alkoxy group;

or a pharmaceutically acceptable salt thereof.

2. The compound as claimed in claim 1, which is selected from:
(1) 4'-({6-(5-carbamoylpyridin-3-yl)-4-oxospiro[chroman-2,4'-piperidin]-1'-yl}carbonyl)-2',6'-diethoxybiphenyl-3-carboxylic acid;
(2) 2',6'-diethoxy-4'-{[6-(1H-pyrazol-5-yl)-4-oxospiro[chroman-2,4'-piperidin]-1'-yl]carbonyl}biphenyl-4-carboxylic acid;
(3) 4'-({6-(4-carbamoylphenyl)-4-oxospiro [chroman-2,4'-piperidin]-1'-yl }carbonyl)-2',6'-diethoxybiphenyl-4-carboxylic acid;
(4) 4'-({6-(3-carbamoylphenyl)-4-oxospiro [chroman-2,4'-piperidin]-1'-yl}carbonyl)-2',6'-diethoxybiphenyl-4-carboxylic acid;
(5) 4'-({6-(5-carbamoylpyridin-2-yl)-4-oxospiro[chroman-2,4'-piperidin]-1'-yl}carbonyl)-2',6'-diethoxybiphenyl-4-carboxylic acid;
(6) 4'-({6-(5-carbamoylpyridin-3-yl)-4-oxospiro[chroman-2,4'-piperidin]-1'-yl}carbonyl)-2',6'-diethoxybiphenyl-4-carboxylic acid;
(13) 2',6'-diethoxy-4'-{[6-(1-methyl-1H-pyrazol-4-yl)-4-oxospiro[chroman-2,4'-piperidin]-1'-yl]carbonyl}biphenyl-4-carboxylic acid;
(14) 4'-({6-(5-carbamoylpyridin-2-yl)-4-oxospiro[chroman-2,4'-piperidin]-1'-yl}carbonyl)-2',6'-diethoxybiphenyl-3-carboxylic acid;
(15) 2',6'-diethoxy-4'-{[6-(1-methyl-1H-pyrazol-4-yl)-4-oxospiro[chroman-2,4'-piperidin]-1'-yl]carbonyl}biphenyl-3-carboxylic acid;
(16) 5-(2,6-diethoxy-4-{[6-(1-methyl-1H-pyrazol-4-yl)-4-oxospiro[chroman-2,4'-piperidin]-1'-yl]carbonyl}phenyl)nicotinic acid;
(17) 2',6'-diethoxy-3-fluoro-4'-{[6-(1-methyl-1H-pyrazol-4-yl)-4-oxospiro[chroman-2,4'-piperidin]-1'-yl]carbonyl}biphenyl-4-carboxylic acid;
(18) 5-[4-({6-(3-carbamoylphenyl)-4-oxospiro[chroman-2,4'-piperidin]-1'-yl}carbonyl)-2,6-diethoxyphenyl]nicotinic acid; and
(19) 2',6'-diethoxy-4-fluoro-4'-{[6-(1-methyl-1H-pyrazol-4-yl)-4-oxospiro[chroman-2,4'-piperidin]-1'-yl]carbonyl}biphenyl-3-carboxylic acid;

or a pharmaceutically acceptable salt thereof.

3. The compound as claimed in claim 1, which is 4'-({6-(5-carbamoylpyridin-2-yl)-4-oxospiro [chroman-2,4'-piperidin]-1'-yl}carbonyl)-2',6'-diethoxybiphenyl4-carboxylic acid; or a pharmaceutically acceptable salt thereof.

4. The compound as claimed in claim 1, which is 2',6'-diethoxy-4'-{[6-(1-methyl-1H-pyrazol-4-yl)-4-oxospiro [chroman-2,4'-piperidin]-1'-yl]carbonyl}biphenyl-4-carboxylic acid; or a pharmaceutically acceptable salt thereof.

5. The compound as claimed in claim 1, which is 2',6'-diethoxy-3-fluoro-4'-{[6-(1-methyl-1H-pyrazol-4-yl)-4-oxospiro[chroman-2,4'-piperidin]-1'-yl]carbonyl}biphenyl-4-carboxylic acid; or a pharmaceutically acceptable salt thereof.

6. The compound as claimed in claim 1, which is 5-[4-({6-(3-carbamoylphenyl)-4-oxospiro[chroman-2,4'-piperidin]-1'-yl}carbonyl)-2,6-diethoxyphenyl]nicotinic acid; or a pharmaceutically acceptable salt thereof.

7. The compound as claimed in claim 1, which is sodium 4'-({6-(5-carbamoylpyridin-2-yl)-4-oxospiro[chroman-2,4'-piperidin]-1'-yl}carbonyl)-2',6'-diethoxybiphenyl-4-carboxylate.

8. A pharmaceutical composition comprising a therapeutically effective amount of the compound of claim 1 or a pharmaceutically acceptable salt thereof, and a pharmaceutically acceptable additive.

* * * * *

UNITED STATES PATENT AND TRADEMARK OFFICE
CERTIFICATE OF CORRECTION

PATENT NO. : 8,524,730 B2
APPLICATION NO. : 12/997263
DATED : September 3, 2013
INVENTOR(S) : Hideki Jona, Yoshihiro Shibata and Takeru Yamakawa It is certified that error appears in the above-identified patent and that said Letters Patent is hereby corrected as shown below:

On the Title Page, Item (54) and in the Specification, Column 1, Line 1, Title mistakenly appears as follows:

SPIROCHIROMANONE CARBOXYLIC ACID and Title Item (54) should appear as follows:

NOVEL SPIROCHIROMANONE CARBOXYLIC ACID

Signed and Sealed this
Eighth Day of October, 2013

Teresa Stanek Rea
*Deputy Director of the United States Patent and Trademark Office*